US008518884B2

(12) United States Patent
Arora et al.

(10) Patent No.: US 8,518,884 B2
(45) Date of Patent: *Aug. 27, 2013

(54) METHODS FOR TREATING ATRIAL OR VENTRICULAR ARRHYTHMIAS BY ADMINISTERING A G-PROTEIN ALPHA INHIBITOR

(75) Inventors: Rishi Arora, Chicago, IL (US); Gary L. Aistrup, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,412

(22) Filed: May 21, 2012

(65) Prior Publication Data

US 2012/0329718 A1    Dec. 27, 2012

Related U.S. Application Data

(63) Continuation-in-part of application No. 12/430,595, filed on Apr. 27, 2009, now Pat. No. 8,193,151.

(60) Provisional application No. 61/048,033, filed on Apr. 25, 2008.

(51) Int. Cl.
*A61K 38/00* (2006.01)
*A61P 9/12* (2006.01)
*C07K 14/575* (2006.01)
*A61K 48/00* (2006.01)

(52) U.S. Cl.
USPC ........................................ 514/16.1; 514/44 R

(58) Field of Classification Search
None
See application file for complete search history.

(56) References Cited

U.S. PATENT DOCUMENTS

| 5,824,544 | A | 10/1998 | Armentano et al. |
| 5,830,730 | A | 11/1998 | German et al. |
| 5,872,154 | A | 2/1999 | Wilson et al. |
| 5,885,808 | A | 3/1999 | Spooner et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 5,994,132 | A | 11/1999 | Chamberlain et al. |
| 6,001,557 | A | 12/1999 | Wilson et al. |
| 6,019,978 | A | 2/2000 | Ertl et al. |
| 6,033,908 | A | 3/2000 | Bout et al. |
| 6,506,559 | B1 | 1/2003 | Fire et al. |
| 7,328,064 | B2 | 2/2008 | Mathiesen et al. |
| 8,193,151 | B2 | 6/2012 | Arora et al. |
| 2003/0162258 | A1 | 8/2003 | Hamm et al. |
| 2007/0077597 | A1 | 4/2007 | Gilchrist et al. |
| 2007/0231830 | A1 | 10/2007 | Gilchrist et al. |

FOREIGN PATENT DOCUMENTS

| WO | 0009675 | 2/2000 |
| WO | 0012738 | 3/2000 |

OTHER PUBLICATIONS

El-Armouche A, et al., Cardiovascular Research, 60:478-487, 2003.*
Thoren et al., "Uptake of analogs of penetratin, Tat (48-60) and oligoarginine in live cells," Biochem. Biophys. Res. Comm, 2003, 307(1):100-107.
Ulphani et al., "Autonomic Innervation of the Pulmonary Veins," J Am Coll Cardiol, 2005, 45(3):122A.
Ulphani et al., "Parasympathetic Innervations of the Posterior Left Atrium Primarily Originate in the Ligament of Marshall", Circulation, 2005, 112(17):II-189.
Ulphani et al., "The ligament of Marshall as a parasympathetic condiut," Am. J. Physiol. Heart Circ. Physiol, 2007, 293(3):H1629-H1635.
Villuendas et al., "Atrial Autonomic Remodeling in a Canine Model of Congestive Heart Failure," Circulation 116: II_250_II_251), presented at AHA 2007.
Villuendas et al., "Heterogeneous Innervation of the Left Atrium and Pulmonary Veins", J. Am. Coll. Cardiology, 2007, 49(9):20A.
Villuendas et al., "Selective Pharmacologic Blockade of Parasympathetic Innervation in the Posterior Left Atrium Modifies Substrate for Atrial Fibrillation", Heart Rhythm, 2007, 4(5S):S169.
Villuendas, "Heterogeneous distribution of Muscarinic receptors contributes to the substrate for Vagal atrial fibrillation," Circulation 116:II_279, presented at AHA 2007.
Ye et al., "Galpha(i2), Galpha(i3)and Galpha(o) are all required for normal muscarinic inhibition of the cardiac calcium channels in nodal/atrial-like cultured cardiocytes," J Mol Cell Cardiol, 1999, 31: 1771-1781.
Yue et al., "Transient outward and delayed rectifier currents in canine atrium: properties and role of isolation methods," Am J Physiol, 1996, 270: H2157-2168.
Zhang et al., "Gating properties of GIRK channels activated by Galpha(o)- and Galpha(i)-coupled muscarinic m2 receptors in *Xenopus* oocytes: the role of receptor precoupling in RGS modulation," J Physiol, 2002, 545: 355-373.
Zuckermann et al., 1994, "Discovery of nanomolar ligands for 7-transmembrane G-protein-coupled receptors from a diverse N-(substituted)glycine peptoid library," J. Med. Chem. 37(17):2678-2685.
El-Armouche et al., "Inhibitory G-proteins and their role in desensitization of the adenylyl cyclase pathway in heart failure," Cardiovasc Res, 2003, 60: 478-487.
Aistrup et al., "Targeted G-protein inhibition as a novel approach to decrease vagal atrial fibrillation by selective parasympathetic attenuation," Cardiovasc Res, 2009, 83: 481-492.
Aistrup et al., "Targeted nonviral gene-based inhibition of Gα(i/o)-mediated vagal signaling in the posterior left atrium decreases vagal-induced atrial fibrillation," Heart Rhythm, 2011, 8(11):1722-9.

(Continued)

*Primary Examiner* — Robert Landsman
(74) *Attorney, Agent, or Firm* — Casimir Jones, S.C.

(57) ABSTRACT

The present invention provides compositions and methods for treating heart conditions. In particular, the present invention provides compositions and methods that block G protein coupled receptor mediated signaling for treating atrial fibrillation.

20 Claims, 29 Drawing Sheets

(56) References Cited

OTHER PUBLICATIONS

Amit et al., "Selective molecular potassium channel blockade prevents atrial fibrillation," Circulation, 2010, 121: 2263-2270.
Arora et al., "Autonomic Profile of the Pulmonary Veins", Heart Rhythm, 2005, 2(5), Supplement, S180.
Arora et al., "Neural substrate for atrial fibrillation: implications for targeted parasympathetic blockade in the posterior left atrium," Am. J. Physiol. Heart Circ. Physiol., 2008, 294(1):H134-144.
Arora et al., "Targeted G-Protein Inhibition in the Posterior Left Atrium—A Novel Method to Selectively Inhibit Parasympathetic Signaling in the Left Atrium", Heart Rhythm, 2007, 4(5S):S9.
Arora et al., "Unique autonomic profile of the pulmonary veins and posterior left atrium," J. Am. Coll. Cardiol. 2007, 49(12):1340-1348.
Bauer et al., "Inhibitory G protein overexpression provides physiologically relevant heart rate control in persistent atrial fibrillation," Circulation, 2004, 110: 3115-3120.
Belin et al., "Molecular Basis for Sympathetic Remodeling in the Left Atrium in the Ventricular Tachypacing Canine Model of Congestive Heart Failure," presented at AHA 2007.
Benjamin et al., "Independent risk factors for atrial fibrillation in a population-based cohort. The Framingham Heart Study," JAMA, 1994, 271: 840-844.
Boknik et al., "Genetic disruption of G proteins, G(i2)alpha or G(o)alpha, does not abolish inotropic and chronotropic effects of stimulating muscarinic cholinoceptors in atrium," Br J Pharmacol, 2009, 158: 1557-1564.
Boyle et al., "Metabolic stabilization of benzylidene ketal M(2) muscarinic receptor antagonists via halonaphthoic acid substitution," Bioorg Med. Chem. Lett. 2001, 11(17):2311-2314.
Brodde et al., "Signal transduction mechanisms controlling cardiac contractility and their alterations in chronic heart failure," Cardiovasc. Res., 1995, 30(4):570-584.
Brummelkamp et al., "A system for stable expression of short interfering RNAs in mammalian cells," Science, 2002, 296:550-553.
Burashnikov et al., "Reinduction of atrial fibrillation immediately after termination of the arrhythmia is mediated by late phase 3 early afterdepolarization-induced triggered activity," Circulation, 2003, 107: 2355-2360.
Caplen et al., "Specific inhibition of gene expression by small double-stranded RNAs in invertebrate and vertebrate systems," Proc Natl Acad Sci USA, 2001, 98: 9742-9747.
Cokic et al., "A Novel Minigene-based Approach to Achieve Long Term Vagal Inhibition in the Left Atrium," Heart Rhythm, 2010, 7: S94.
Dean et al., "Electroporation as a method for high-level nonviral gene transfer to the lung," Gene Ther, 2003, 10: 1608-1615.
Dean et al., "Nonviral gene transfer to skeletal, smooth, and cardiac muscle in living animals," Am J Physiol Cell Physiol, 2005, 289:C233-245.
Dobrev et al., "Molecular basis of downregulation of G-protein-coupled inward rectifying K(+) current (I(K,ACh) in chronic human atrial fibrillation: decrease in GIRK4 mRNA correlates with reduced I(K,ACh) and muscarinic receptor-mediated shortening of action potentials," Circulation, 2001, 104: 2551-2557.
Dobrev et al., "New antiarrhythmic drugs for treatment of atrial fibrillation," Lancet, 2010, 375: 1212-1223.
Donahue et al., "Focal modification of electrical conduction in the heart by viral gene transfer," Nature Med, 2000, 6: 1395-1398.
Droge et al., "Free radicals in the physiological control of cell function," Physiol Rev, 2002, 82: 47-95.
Ehrlich et al., "Characterization of a hyperpolarization-activated time-dependent potassium current in canine cardiomyocytes from pulmonary vein myocardial sleeves and left atrium," J. Physiol, 2004, 557(Pt 2):583-597.
Elbashir et al., "Duplexes of 21-nucleotide RNAs mediate RNA interference in cultured mammalian cells," Nature, 2001, 411: 494-498.
Elbashir et al., "Functional anatomy of siRNAs for mediating efficient RNAi in *Drosophila melanogaster* embryo lysate," EMBO J, 2001, 20: 6877-6888.
Elbashir et al., "RNA interference is mediated by 21- and 22-nucleotide RNAs," Genes Dev, 2001, 15: 188-200.
Ellis et al., "Thrombin induces proteinase-activated receptor-1 gene expression in endothelial cells via activation of Gi-linked Ras/mitogen-activated protein kinase pathway," J Biol Chem, 1999, 274:13718-13727.
Feldman et al., "Increase of the 40,000-mol wt pertussis toxin substrate (G protein) in the failing human heart," J. Clin. Invest, 1988, 82(1):189-197.
Futaki et al., "Arginine-rich peptides. An abundant source of membrane-permeable peptides having potential as carriers for intracellular protein delivery," J. Biol. Chem, 2001, 276(8):5836-5840.
Genaro, Remington's Pharmaceutical Sciences, 1985, Mack Publishing Co, Easton PA.
Gilchrist et al., "A dominant-negative strategy for studying roles of G proteins in vivo," J. Biol. Chem, 1999, 274 (10):6610-6616.
Gilchrist et al., "Antagonists of the receptor-G protein interface block Gi-coupled signal transduction," J. Biol. Chem., 1998, 273:14912-14919.
Gilchrist et al., "Design and use of C-terminal minigene vectors for studying role of heterotrimeric G proteins," Methods Enzymol., 2002, 344:58-69.
Gilchrist et al., "Gα COOH-Terminal Minigene Vectors Dissect Heterotrimeric G Protein Signaling", Sci. STKE, 2002, 5(118):PL1.
Giordano et al., "Oxygen, oxidative stress, hypoxia, and heart failure," J Clin Invest, 2005, 115: 500-508.
Holen et al., "Positional effects of short interfering RNAs targeting the human coagulation trigger Tissue Factor," Nucleic Acids Res, 2002, 30: 1757-1756.
Kozlowski et al., "Diphenyl sulfoxides as selective antagonists of the muscarinic M2 receptor," Bioorg Med. Chem. Lett. 2000, 10(20): 2255-2257.
Li et al., "Effects of experimental heart failure on atrial cellular and ionic electrophysiology," Circulation, 2000, 101: 2631-2638.
Lyon et al., "Gene therapy: targeting the myocardium," Heart, 2008, 94: 89-99.
Ma et al., "Heterooligomers of the muscarinic receptor and G proteins purified from porcine atria," Biochem Biophys Res Commun, 2008, 374: 128-133.
Ng et al., "Autonomic remodeling in the left atrium and pulmonary veins in heart failure: creation of a dynamic substrate for atrial fibrillation," Circ Arrhythm Electrophysiol, 2011, 4(3):388-96.
Nilius, "Desensitization of the muscarinic receptor in the mammalian atrial myocardium," Biomed Biochim Acta, 1983, 42: 519-526.
Oliveira et al., "Acute vagal modulation of electrophysiology of the atrial and pulmonary veins increases vulnerability to atrial fibrillation," Exp Physiol, 2011, 96: 125-133.
Patterson et al., "Triggered firing in pulmonary veins initiated by in vitro autonomic nerve stimulation," Heart Rhythm, 2005, 2: 624-631.
Rudolph et al., "Adenylyl cyclase inhibition and altered G protein subunit expression and ADP-ribosylation patterns in tissues and cells from Gi2 alpha-/-mice," Proc Natl Acad Sci USA, 1996, 93: 3209-3214.
Sharifov et al., "Roles of adrenergic and cholinergic stimulation in spontaneous atrial fibrillation in dogs," J Am Coll Cardiol, 2004, 43: 483-490.
Song et al., "An increase of late sodium current induces delayed afterdepolarizations and sustained triggered activity in atrial myocytes," Am J Physiol, 2008, 294: H2031-2039.
Sturrock et al., "Transforming growth factor-beta1 induces Nox4 NAD(P)H oxidase and reactive oxygen species-dependent proliferation in human pulmonary artery smooth muscle cells," Am J Physiol Lung Mol Physiol, 2006, 290: L661-L673.

* cited by examiner a) Effect of ISO on Ca$^{2+}$ transients in the absence of cp-Gαi
↓Tyrode's+1μM ISO 2 sec b) Effect of ISO on Ca$^{2+}$ transients after 10min exposure to 100nM cp-Gαi
Tyrode's. ↓+1μM ISO ....2min 1μM ISO 2 sec

A. NERVE BUNDLES

B. NERVE BUNDLE SIZE

METHODS FOR TREATING ATRIAL OR VENTRICULAR ARRHYTHMIAS BY ADMINISTERING A G-PROTEIN ALPHA INHIBITOR

The present application is a continuation-in-part of U.S. application Ser. No. 12/430,595 filed Apr. 27, 2009, now U.S. Pat. No. 8,193,151, which claims priority to U.S. Provisional Patent Application Ser. No. 61/048,033 filed Apr. 25, 2008, both of which are herein incorporated by reference in their entireties.

STATEMENT REGARDING FEDERALLY SPONSORED RESEARCH OR DEVELOPMENT

The present invention was made with government support under grant numbers 5K08 HL074192, R01 HL093490, and R21 HL088304 awarded by the National Institutes of Health. The government has certain rights in the invention.

FIELD OF THE INVENTION

The present invention provides compositions and methods for treating heart conditions. In particular, the present invention provides compositions and methods that block G protein coupled receptor mediated signaling for treating atrial fibrillation.

BACKGROUND

Atrial fibrillation is a disorder found in about 2.2 million Americans. During atrial fibrillation, the heart's two small upper chambers (the atria) quiver instead of beating effectively. Blood is not pumped completely out of them, so it may pool and clot. If a piece of a blood clot in the atria leaves the heart and becomes lodged in an artery in the brain, a stroke results. About 15 percent of strokes occur in people with atrial fibrillation. The likelihood of developing atrial fibrillation increases with age. Three to five percent of people over 65 have atrial fibrillation.

Several approaches are used to treat and prevent abnormal beating. Medications are used to slow down rapid heart rate associated with AF. These treatments may include drugs such as digoxin, beta blockers (e.g. atenolol, metoprolol, propranolol), amiodarone, disopyramide, calcium antagonists (e.g. verapamil, diltiazam), sotalol, flecamide, procainamide, quinidine, propafenone, etc. Electrical cardioversion may be used to restore normal heart rhythm with an electric shock, when medication does not improve symptoms. Drugs (such as ibutilide) can sometimes restore the heart's normal rhythm. These drugs are given under medical supervision, and are delivered through an IV tube into a vein, usually in the patient's arm. Radiofrequency ablation may be effective in some patients when medications don't work. In this procedure, thin and flexible tubes are introduced through a blood vessel and directed to the heart muscle. Then a burst of radiofrequency energy is delivered to destroy tissue that triggers abnormal electrical signals or to block abnormal electrical pathways. Surgery can be used to disrupt electrical pathways that generate AF. Atrial pacemakers can be implanted under the skin to regulate the heart rhythm.

In recent years, the pulmonary veins (PVs) and posterior left atrium (PLA) have been shown to play a role in the genesis as well as maintenance of AF. Despite an improved understanding of the underlying mechanisms of AF, current pharmacologic as well as ablative approaches to cure this arrhythmia are inadequate.

SUMMARY

In some embodiments, the present invention provides a method for treating a subject having atrial or ventricular arrhythmias, comprising exposing the subject to a G-protein inhibitor. In some embodiments, the arrhythmia comprises atrial fibrillation. In some embodiments, exposing the subject to a G-protein inhibitor disrupts one or more autonomic pathways. In some embodiments, the autonomic pathways comprise sympathetic or parasympathetic pathways. In some embodiments, exposing the subject to a G-protein inhibitor comprises local administration. In some embodiments, the present invention further comprises electroporation of the site of local administration. In some embodiments, the G-protein inhibitor comprises a G-protein inhibitory peptide. In some embodiments, the G-protein inhibitory peptide is an inhibitor to $G\alpha I$, $G\alpha s$, and/or $G\alpha$ (e.g. $G\alpha q$, $G\alpha 11$, $G\alpha 12$, $G\alpha 13$, $G\alpha 14$, $G\alpha 15$, $G\alpha 16$, $G\alpha o1$, etc.). In some embodiments, the G-protein inhibitory peptide is configured to block receptor/G protein interaction. In some embodiments, the G-protein inhibitor comprises a nucleic acid molecule encoding a G-protein inhibitory peptide. In some embodiments, exposing the subject to a G-protein inhibitor comprises topical administration. In some embodiments, the subject is undergoing open-heart surgery. In some embodiments, the subject is undergoing percutaneous catheter based delivery. In some embodiments, the subject has a clinical history with a role of vagal or adrenergic system associated with the atrial fibrillation. In some embodiments, the subject has a paroxysmal or chronic history of atrial fibrillation. In some embodiments, exposing the subject to a G-protein inhibitor comprises treatment of autonomic pathways: a) within the left or right atrium of the heart; b) adjacent to the atria, or c) at one or more sites distant from the atria but that innervate the atria. In some embodiments, exposing the subject to a G-protein inhibitor comprises treatment of autonomic pathways in ventricular arrhythmias.

In some embodiments, the present invention provides a method for treating a subject having atrial fibrillation comprising locally administering a G-protein inhibitor to the heart of the subject, and electroporating the site of administration. In some embodiments, the G-protein inhibitor is applied topically using a catheter or injection apparatus. In some embodiments, the G-protein inhibitor comprises an inhibitory peptide, nucleic acid, or small molecule. In some embodiments, the G-protein inhibitor comprises an inhibitor to $G\alpha I$, $G\alpha s$, $G\alpha o1$, and/or $G\alpha$.

In certain embodiments, the present invention provides methods for treating a subject having atrial or ventricular arrhythmias, comprising administering the subject an effective amount of a G-protein inhibitor, wherein said G-protein inhibitor comprises a $G\alpha o1$ inhibitor, and wherein the administering is under conditions such that symptoms of the atrial or ventricular arrhythmias are reduced or eliminated.

In certain embodiments, the present invention provides systems, kits, and compositions comprising: a) a G-protein inhibitor, wherein the G-protein inhibitor comprises a $G\alpha o$ inhibitor (e.g., $G\alpha o1$ inhibitor); and b) a pharmaceutical solution containing the G-protein inhibitor, wherein the pharmaceutical solution is suitable for contact with the heart (e.g., human heart).

BRIEF DESCRIPTION OF THE DRAWINGS

The foregoing summary and detailed description is better understood when read in conjunction with the accompanying drawings which are included by way of example and not by way of limitation.

DETAILED DESCRIPTION OF THE INVENTION

Figure 1:
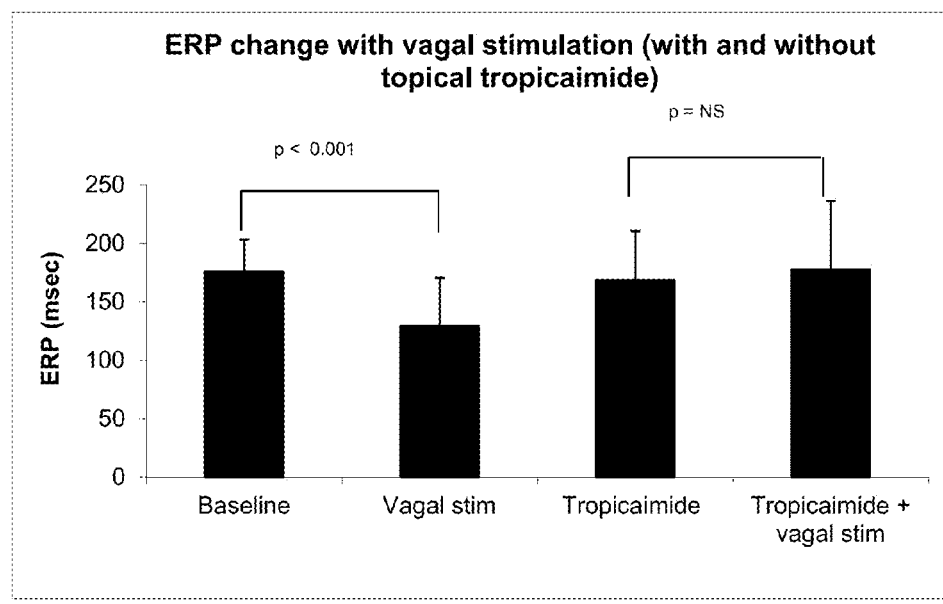
FIG. 1 shows a graph of the ERP change with vagal stimulation, with and without topical tropicaimide.
Figure 2:
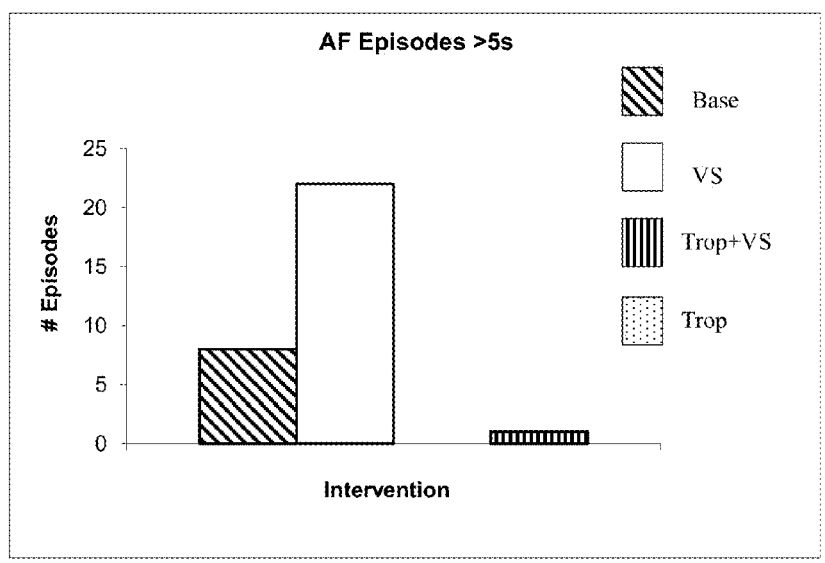
FIG. 2 shows the significant decrease in inducibility of atrial fibrillation in the presence of topical tropicaimide.
Figure 3:
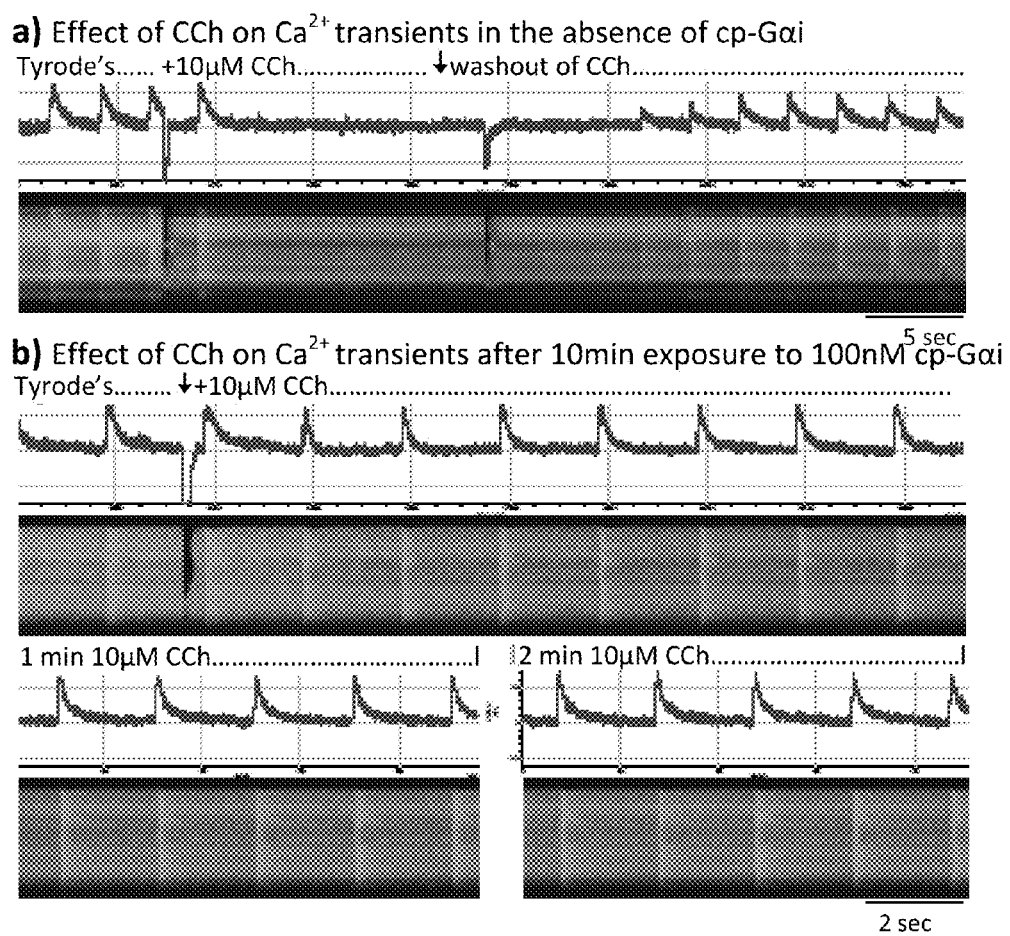
FIGS. 3A and 3B show flou-4 fluorescence confocal line-scans and the resultant mean fluorescence integral $F/F_0$ signals (line tracings above each line-scan image) of $Ca^{2+}$ transients from electrically field-stimulated (0.5 Hz) control and cp-Gαi2/3-exposed or cp-Gαs-exposed individual isolated cardiac myocytes before and after they were superfused with CCh or ISO.

The present invention provides compositions and methods for treating heart conditions (e.g. rhythm disturbances (e.g. atrial fibrillation)). In particular, the present invention provides compositions and methods for treating atrial fibrillation that block G protein coupled receptor mediated signaling.

In some embodiments, the present invention provides compositions and methods to treat or prevent conditions and/or diseases of the heart (e.g. rhythm disturbances (e.g. atrial fibrillation)). In some embodiments, the present invention provides treatment or prevention of a heart disease or condition selected from the list of aortic dissection, cardiac arrhythmia (e.g. atrial cardiac arrhythmia (e.g. premature atrial contractions, wandering atrial pacemaker, multifocal atrial tachycardia, atrial flutter, atrial fibrillation, etc.), junctional arrhythmias (e.g. supraventricular tachycardia, AV nodal reentrant tachycardia, paroxysmal supra-ventricular tachycardia, junctional rhythm, junctional tachycardia, premature junctional complex, etc.), atrio-ventricular arrhythmias, ventricular arrhythmias (e.g. premature ventricular contractions, accelerated idioventricular rhythm, monomorphic ventricular tachycardia, polymorphic ventricular tachycardia, ventricular fibrillation, etc.), etc.), congenital heart disease, myocardial infarction, dilated cardiomyopathy, hypertrophic cardiomyopathy, aortic regurgitation, aortic stenosis, mitral regurgitation, mitral stenosis, Ellis-van Creveld syndrome, familial hypertrophic cardiomyopathy, Holt-Orams Syndrome, Marfan Syndrome, Ward-Romano Syndrome, and/or similar diseases and conditions.

In some embodiments, the present invention provides compositions and methods to treat atrial fibrillation. Atrial fibrillation is the commonest rhythm disturbance of the heart. The posterior left atrium and pulmonary veins have been shown to play an important role in the genesis of atrial fibrillation. More recent studies demonstrate a role for the autonomic nervous system, especially the parasympathetic nervous system, in the genesis of atrial fibrillation from the posterior left atrium. Current therapies to manage atrial fibrillation remain ineffective, while novel links, including autonomic activity described here, provide for beneficial treatment options. Work conducted during the development of embodiments of the present invention shows that selective disruption of autonomic pathways in the posterior left atrium can significantly modify the ability to the heart to sustain atrial fibrillation. In particular, embodiments of the present invention treat atrial fibrillation by administration of G-protein inhibitors (e.g., Gαo and Gαi inhibitors). An understanding of the mechanism of action is not necessary to practice the present invention and the present invention is not limited to any particular mechanism of action. However, it is contemplated that selectively disrupting parasympathetic or sympathetic pathways in the left atrium by means of G-protein inhibitors treats atrial fibrillation. The present invention also provides compositions and methods for researching atrial fibrillation, including screening for compounds useful in treating, prevent, or reducing signs or symptoms associate with atrial fibrillation.

In some embodiments, agents that disrupt autonomic pathways involved in AF are provided. In some embodiments, the present invention provides compositions and methods which disrupt (e.g. block, inhibit, etc.) autonomic pathways. In some embodiments, the present invention provides G-protein inhibitors which disrupt autonomic pathways. In some embodiments, delivery of G-protein inhibitors that selectively block sympathetic or parasympathetic pathways are provided.

In some embodiments, the present invention provides compositions and methods that employ G-protein inhibitors that disrupt autonomic pathways in the heart as a treatment for atrial fibrillation. In some embodiments, the present invention provides G-protein inhibitors to treat a condition or disorder of the heart (e.g. atrial fibrillation). In some embodiments, the present invention provides an inhibitor of G-protein function. In some embodiments, the present invention inhibits the function of G-Proteins (a.k.a. seven transmembrane domain receptors, 7TM receptors, heptahelical receptors, serpentine receptor, G protein-linked receptors, etc.)

In some embodiments, G-protein inhibitors comprise any suitable bioactive molecules (e.g. a molecule capable of inhibiting the function of G-proteins). In some embodiments, a G-protein inhibitor comprises a macromolecule, polymer, a molecular complex, protein, peptide, polypeptide, nucleic acid, carbohydrate, small molecule, etc.

In some embodiments, a G-protein inhibitor is a G-protein inhibitory peptide. In some embodiments, the present invention provides peptides of any suitable amino acid sequence capable of inhibiting one or more G-proteins. In some embodiments, peptides provided by or encoded by the compositions of embodiments of the present invention may comprise any arrangement of any standard amino acids (e.g. alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine) or non-standard amino acids (e.g. D-amino acids, chemically or biologically produced derivatives of common amino acids, selenocysteine, pyrrolysine, lanthionine, 2-aminoisobutyric acid, dehydroalanine, etc.). In some embodiments, G-protein inhibitory peptides are inhibitors to Gα(e.g. GαI, Gαs, Gαq, Gα11, Gα12, Gα13, Gα14, G15, Gαo1, Gα16, etc.), GαI, and/or Gαs. In some embodiments, these peptide sequences mimic the C-terminus of Gα (e.g., Gαo1), GαI, and/or Gαs so as to block receptor/G protein interactions (e.g. 5 C-terminal amino acids, 6 C-terminal amino acids, 7 C-terminal amino acids, 8 C-terminal amino acids, 9 C-terminal amino acids, 10 C-terminal amino acids, 11 C-terminal amino acids, 12 C-terminal amino acids, 13 C-terminal amino acids, 14 C-terminal amino acids, 15 C-terminal amino acids, 16 C-terminal amino acids, 17 C-terminal amino acids, 18 C-terminal amino acids, 19 C-terminal amino acids, 20 C-terminal amino acids, 30 C-terminal amino acids, 40 C-terminal amino acids, 50 C-terminal amino acids, full C-terminal region, etc.). In some embodiments, for example, a G-protein inhibitory peptide of the present invention comprises the C-terminus of Gαi (NCBI Accession Number ACN58588.1; GI:224586986). In some embodiments, for example, a G-protein inhibitory peptide of the present invention comprises the 11 C-terminal amino acids of Gαi (e.g. amino acid sequence IKNNLKDCGLF (SEQ ID NO:7)). In certain embodiments, a G-protein inhibitory peptide of the present invention comprises the C-terminus of Gαo1 (see, full sequences at NCBI Accession Number AAH30027; nucleic acid sequence NM_020988).

In some embodiments, peptides mimic the C-terminus of Gα (e.g. GαI, Gαs, Gαq, Gα11, Gα12, Gα13, Gα14, Gα15, Gαo1, Gα16, etc.), GαI, and/or Gαs to competitively inhibit G-protein interactions. In some embodiments, G-protein inhibitory peptides are fragments of a G-protein. In some embodiments, G-protein inhibitory peptides mimic the C-terminus of a G-protein (e.g. GαI, Gαs, Gα, Gαo1, etc.), but vary from the wild-type sequence (e.g. different length, variant amino acids, etc.). In some embodiments, peptides are variant forms of G-proteins or fragments thereof. In some embodiments, peptides provided are variant sequences of the C-terminus of GαI, Gαs, and/or Gα (e.g. GαI, Gαs, Gαq, Gα11, Gα12, Gα13, Gα14, Gα15, Gαo1, Gα16, etc.). In some embodiments, G-protein inhibitory peptides are provided to a subject as isolated or purified peptides. In some embodiments, G-protein inhibitory peptides are provided to a subject as nucleic acid molecules that encode such peptides. In some embodiments, peptides are optimized to enhance cell penetration (e.g. sequence optimization, sequence tag, tagged with a small molecule, etc.).

Exemplary inhibitors of the present invention include those described in U.S. Pat. Publ. 20030162258, 20070231830, and 20070077597, each of which is herein incorporated by reference in its entirety. These references further describe methods for identifying and selecting additional inhibitors.

In some embodiments, a G-protein inhibitor is provided from an isolated nucleic acid comprising a minigene, wherein said minigene encodes a modified carboxy terminal Gα peptide, wherein the peptide blocks the site of interaction between a G protein and a G protein coupled receptor in a cell, such as a human cell. In addition, the minigene can further comprise one or more of a promoter, a ribosomal binding site, a translation initiation codon, and a translation termination codon. In some embodiments, the minigene encodes a modified carboxy terminal Gα peptide (e.g., Gαo1 peptide) having one of the following general formulas: MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide which comprises an amino acid sequence of the carboxy terminus of a Gα subunit, and has the property of binding a G protein coupled receptor. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit.

In some embodiments, the inhibitor is provided as an isolated or purified polypeptide. In some embodiments, the peptide has a general formula selected from the group consisting of MGX, MX, and MZX, wherein M is a methionine amino acid residue, wherein G is a glycine amino acid residue, wherein Z is an amino acid residue other than a glycine amino acid residue, and wherein X is a carboxy terminal Gα peptide (e.g., Gαo1 peptide) which comprises an amino acid sequence of the carboxy terminus of a Gα subunit, and has the property of binding a G protein coupled receptor. In this embodiment, X can comprise from at least about three contiguous amino acids to at least about 54 contiguous amino acids, from at least about three contiguous amino acids to at least about eleven contiguous amino acids, and at least about eleven contiguous amino acids. In one embodiment, X comprises the seven contiguous terminal amino acid residues of the carboxy terminus of a Gα subunit.

In some embodiments, the present invention provides methods of inhibiting a G protein-mediated signaling event in a cell or tissue. These methods comprise administering to a cell or tissue, preferably a human cell or tissue, one of a modified carboxy terminal Gα peptide (e.g., Gαo peptide), and an isolated nucleic acid comprising a minigene which encodes a modified carboxy terminal Gα peptide, whereby following the administration, the carboxy terminal Gα peptide inhibits the G protein mediated signaling event in the cell or tissue.

In some embodiments, a G-protein inhibitor comprises a small molecule. In some embodiments, the present invention provides a small molecule inhibitor of a G protein (e.g., Gαo or Gαi protein). In some embodiments, the present invention provides a small molecule drug or pharmaceutical compound configured to or capable of inhibiting G-protein activity, function expression, or the like.

In some embodiments, the present invention provides RNAi molecules (e.g., that alter G-protein expression) as a G-protein inhibitor. In some embodiments, the present invention targets the expression of G-protein genes (e.g., Gαo1) using nucleic acid based therapies. For example, in some embodiments, the present invention employs compositions comprising oligomeric antisense or RNAi compounds, particularly oligonucleotides, for use in modulating the function of nucleic acid molecules encoding G-protein genes, ultimately modulating the amount of G-protein expressed. In some embodiments, RNAi is utilized to inhibit G-protein gene function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

In some embodiments, shRNA techniques (See e.g., 20080025958, herein incorporated by reference in its entirety) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

In some embodiments, G-protein expression (e.g., Gαo1 protein expression) is modulated using antisense compounds that specifically hybridize with one or more nucleic acids encoding G-protein. The specific hybridization of an oligomeric compound with its target nucleic acid interferes with the normal function of the nucleic acid. This modulation of function of a target nucleic acid by compounds that specifically hybridize to it is generally referred to as "antisense."

In some embodiments, the present invention contemplates the use of any genetic manipulation for use in modulating the expression of G-protein genes. Examples of genetic manipulation include, but are not limited to, gene knockout (e.g., removing the G-protein gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter.

In some embodiments, the present invention provides antibodies that target G-proteins. Any suitable antibody (e.g., monoclonal, polyclonal, or synthetic) may be utilized in the therapeutic methods disclosed herein. In preferred embodiments, the antibodies are humanized antibodies. Methods for humanizing antibodies are well known in the art (See e.g., U.S. Pat. Nos. 6,180,370, 5,585,089, 6,054,297, and 5,565, 332; each of which is herein incorporated by reference).

In some embodiments, the present invention provides methods of enhancing entry of a G-protein inhibitor into cells or tissue. In some embodiments, the present invention provides administering a G-protein inhibitor in conjunction with electroporation, electropermeabilization, or sonoporation. In some embodiments, the present invention provides administering a G-protein inhibitor in conjunction with electroporation. In some embodiments, the present invention provides co-injection/electroporation of the tissue of a subject. In some embodiments, the present invention provides administering a G-protein inhibitor prior to, simultaneously with, and/or following electroporation. In some embodiments, electroporation provides a method of delivering pharmaceuticals or nucleic acids (e.g. DNA) into cells. In some embodiments, tissue electrically stimulated at the same time or shortly after pharmaceutical or DNA is applied (e.g. G-protein inhibitor). In some embodiments, electroporation increases cell permeability. The permeability or the pores are large enough to allow the pharmaceuticals and/or DNA to gain access to the cells. In some embodiments, the pores in the cell membrane close and the cell once again becomes impermeable or less permeable. Devices for co-injection/electroporation are known in the art (U.S. Pat. No. 7,328,064, herein incorporated by reference in its entirety).

In some embodiments, compositions and methods provided by the present invention are configured to inhibit the activity, expression, or function of all G-proteins. In some embodiments, the present invention provides selective inhibition. In some embodiments, a selective inhibitor provides selective inhibition of G-proteins over one or more other classes of proteins (e.g. 1.1-fold selectivity . . . 1.2-fold selectivity . . . 1.3-fold selectivity . . . 1.4-fold selectivity . . . 1.5-fold selectivity . . . 2.0-fold selectivity . . . 2.5-fold selectivity . . . 3-fold selectivity . . . 4.0-fold selectivity . . . 5.0-fold selectivity . . . 10-fold selectivity . . . 20-fold selectivity . . . 50-fold selectivity . . . 100-fold . . . 1000-fold selectivity . . . etc.). In some embodiments, the present invention provides selective inhibition of one or more specific G-proteins. In some embodiments, a selective inhibitor provides selective inhibition of a class or subgroup G-proteins over one or more other classes of G-proteins (e.g. 1.1-fold selectivity . . . 1.2-fold selectivity . . . 1.3-fold selectivity . . . 1.4-fold selectivity . . . 1.5-fold selectivity . . . 2.0-fold selectivity . . . 2.5-fold selectivity . . . 3-fold selectivity . . . 4.0-fold selectivity . . . 5.0-fold selectivity . . . 10-fold selectivity . . . 20-fold selectivity . . . 50-fold selectivity . . . 100-fold . . . 1000-fold selectivity . . . etc.). In some embodiments, the present invention provides selective inhibition of a subset of G-proteins. In some embodiments, the present invention provides selective inhibition of G-proteins which bind a specific ligand (e.g. adenosine, bombesin, bradykinin, endothelin, γ-aminobutyric acid, hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine, norepinephrine, histamine, glutamate (metabotropic effect), glucagon, acetylcholine (muscarinic effect), and serotonin); chemokines; lipid mediators of inflammation (e.g., prostaglandins, prostanoids, platelet-activating factor, and leukotrienes); and peptide hormones (e.g., calcitonin, C5a anaphylatoxin, follicle-stimulating hormone (FSH), gonadotropic-releasing hormone (GnRH), neurokinin, thyrotropin-releasing hormone (TRH), oxytocin, and/or an orphan receptor). In some embodiments, the present invention provides inhibition of one or more classes of G-protein (e.g. Class A (or 1) (Rhodopsin-like), Class B (or 2) (Secretin receptor family), Class C (or 3) (Metabotropic glutamate/pheromone), Class D (or 4) (Fungal mating pheromone receptors), Class E (or 5) (Cyclic AMP receptors), Class F (or 6) (Frizzled/Smoothened), etc.). In some embodiments, present invention provides selective inhibition of one or more muscarinic acetylcholine receptors (a.k.a. muscarinic receptors, mAChRs). In some embodiments, the present invention selectively inhibits one or more subtypes or isoforms of G-proteins (e.g. a subtype of muscarinic G-protein-coupled receptors) selected from the list of $M_1$, $M_2$, $M_3$, $M_4$, and $M_5$. In some embodiments, the present invention provides $M_2$ selective inhibition. In some embodiments, the present invention provides a peptide, nucleic acid, small molecule, or other method of selectively inhibiting $M_2$-type muscarinic G-protein-coupled receptors. In some embodiments, $M_2$-type muscarinic G-protein-coupled receptor expression from the CHRMs gene is selectively inhibited. In some embodiments, the activity or function of $M_2$-type muscarinic G-protein-coupled receptors are selectively inhibited. In some embodiments, selective inhibition of $M_2$-type muscarinic G-protein-coupled receptors involves an agonist (e.g. acetylcholine, methacholine, carbachol, oxotremorine, etc.) or antagonist (e.g. atropine, dicycloverine, tolterodine, oxybutynin, ipratropium, methoctramine, tripitamine, gallamine, etc.) of $M_2$-type muscarinic G-protein-coupled receptors. $M_2$ selective antagonists are further described in Kozlowski et al. Bioorg Med Chem. Lett. 2000; 10(20):2255-7., Boyle et al. Bioorg Med Chem Lett. 2001; 11(17):2311-4., and McNamara et al. Eur J. Pharmacol. 2009; 605(1-3):145-52., herein incorporated by reference in their entireties.

The compositions and methods of the invention find use in a variety of medical and research applications. For example, in some embodiments, local application of nucleic acids or peptides is applied in the setting of open-heart surgery. Atrial fibrillation is seen in up to 30% of patients after open-heart surgery and has been demonstrated to be at least partially autonomically mediated. Post-operative AF is a cause of significant postoperative morbidity and increases health care costs by several millions of dollars on account of increased hospital lengths of stay. Any drug/agent that reduces the incidence/severity of post-op AF would have a tremendous impact in reducing morbidity and as well as costs in this area of cardiovascular medicine/surgery.

In some embodiments, application of nucleic acids or peptides is applied for vagal and/or adrenergic AF therapy. In selected patients where the role of vagal or adrenergic system is clear from the clinical history (e.g., vagal or adrenergic AF), G$\alpha$i, G$\alpha$o, or G$\alpha$s peptides are tailored to the individual patient. Since the vagus has been shown to have a more dominant role (with the S nervous system playing more of a modulatory role) in the creation of AF substrate, it is contemplated that in most patients with lone AF, either G$\alpha$i peptides alone or a combination of G$\alpha$i and G$\alpha$s peptides provide therapeutic value.

In some embodiments, application of nucleic acids or peptides is applied for paroxysmal and/or chronic atrial fibrillation. Targeted delivery of G-protein inhibitors (peptide/naked DNA/adenovirus) to the left atrium may be applied by catheter based or open-surgical techniques. In addition, one may use ultrasound or electroporation catheters coated with one or more G-protein inhibitors. In recent years, ultrasound has been demonstrated to aid transfer of therapeutic agents (pharmacologic and genetic) across biological cell membranes. In some embodiments, a focused ultrasound beam is used the transfer of G-protein inhibitor (e.g., in liposomal form) across epi or endocardial cell-membranes in the posterior left atrium.

In some embodiments, the present invention provides any suitable gene transfer system as a means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo.

Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

In some embodiments, the invention provides a pharmaceutical composition comprising a pharmaceutically acceptable carrier and one or more of a modified carboxy terminal G$\alpha$ peptide (e.g., G$\alpha$o peptide), a minigene encoding a modified carboxy terminal G$\alpha$ peptide, a small molecule G-protein inhibitor, and/or other G-protein inhibitory molecules.

The G-protein inhibitors of the present invention can be applied alone, or in combination with other therapies. For example, the G-protein inhibitors may be used in combination with medications, electrical cardioversion, radiofrequency ablation, surgery, atrial pacemakers, or other approaches.

In some embodiments, the present invention provides drug screening assays (e.g., to screen for G-protein inhibitor compounds or compounds which treat a heart condition (e.g. atrial fibrillation). The screening methods of the present invention utilize the methods of the present invention. For example, in some embodiments, the present invention provides methods of screening for compounds that inhibit the activity of one or more G-proteins. Compounds or agents may interfere with transcription, by interacting, for example, with the promoter region. Compounds or agents may interfere with mRNA (e.g., by RNA interference, antisense technologies, etc.). Compounds or agents may interfere with pathways that are upstream or downstream of the biological activity of G-proteins. In some embodiments, candidate compounds are antisense or interfering RNA agents (e.g., oligonucleotides). In other embodiments, candidate compounds are antibodies or small molecules that specifically bind to a G-protein, G-protein regulator, or G-protein-related protein and inhibit its biological function.

In one screening method, candidate compounds are evaluated for their ability to alter the G-protein activity by contacting a compound with a cell expressing a G-protein and then assaying for the effect of the candidate compounds on activity. In some embodiments, compounds are screened for specificity to G-proteins over other proteins and protein classes. In some embodiments, compounds are screened for specificity or selectivity of one or more class or subgroup of G-proteins (e.g. M2 selective inhibitors). In some embodiments, compounds are screened for a certain degree of selectivity over other targets (e.g. 1.1-fold selectivity . . . 1.2-fold selectivity . . . 1.3-fold selectivity . . . 1.4-fold selectivity . . . 1.5-fold selectivity . . . 2.0-fold selectivity . . . 2.5-fold selectivity . . . 3-fold selectivity . . . 4.0-fold selectivity . . . 5.0-fold selectivity . . . 10-fold selectivity . . . 20-fold selectivity . . . 50-fold selectivity . . . 100-fold . . . etc.)

In some embodiments, the present invention provides screening methods for identifying modulators, i.e., candidate or test compounds or agents (e.g., proteins, peptides, peptidomimetics, peptoids, small molecules or other drugs) which bind to G-proteins, have an inhibitory effect on one or more G-proteins, or have an inhibitory effect on G-protein expression. Compounds thus identified can be used to modulate the activity of G-proteins either directly or indirectly in a therapeutic protocol. Compounds that inhibit the activity or expression of G-protein are useful in the treatment of atrial fibrillation or other heart disorders.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection.

In one embodiment, an assay is a cell-based assay in which a cell that expresses a G-protein mRNA, or protein, or biologically active portion thereof is contacted with a test compound, and the ability of the test compound to the modulate G-protein activity is determined. In another embodiment, a cell-free assay is provided in which a G-protein or biologically active portion thereof is contacted with a test compound and the ability of the test compound to bind G-protein or biologically active portion thereof is evaluated.

This invention further pertains to novel agents identified by the above-described screening assays. Accordingly, it is within the scope of this invention to further use an agent identified as described herein (e.g., a G-protein inhibitory agent) in an appropriate animal model to determine the efficacy, toxicity, side effects, or mechanism of action, of treatment with such an agent. Furthermore, novel agents identified by the above-described screening assays can be, used for treatments as described herein.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

The composition may be in the form of a solid, semi-solid or liquid dosage form: such as tablet, capsule, pill, powder, suppository, solution, elixir, syrup, suspension, cream, lozenge, paste and spray. In some embodiments, the therapeutic materials are applied topically to the tissue to be treated. As those skilled in the art would recognize, depending on the chosen route of administration, the composition form of said G-protein inhibitor is determined. In general, it is preferred to use a unit dosage form of the inventive inhibitor in order to achieve an easy and accurate administration of the active pharmaceutical compound. In general, the therapeutically effective pharmaceutical compound is present in such a dosage form at a concentration level ranging from about 0.5% to about 99% by weight of the total composition: i.e., in an amount sufficient to provide the desired unit dose.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, dogs, and birds.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. In some embodiments, the present invention provides doses of pharmaceutical compounds in the range of 0.01 mg to 1000 mg (e.g. 0.01 mg . . . 0.02 mg . . . 0.05 mg . . . 0.1 mg . . . 0.2 mg . . . 0.5 mg . . . 1.0 mg . . . 2.0 mg . . . 5.0 mg . . . 10 mg . . . 20 mg . . . 50 mg . . . 100 mg . . . 200 mg . . . 500 mg . . . 1000 mg, or any values therein). In some embodiments, a G-protein inhibitor of the present invention is provided in a pharmaceutical composition at a concentration in the range of 0.1 mg/ml to 100 mg/ml (e.g. 0.1 mg/ml . . . 0.2 mg/ml . . . 0.5 mg/ml . . . 1.0 mg/ml . . . 2.0 mg/ml . . . 5.0 mg/ml . . . 10 mg/ml . . . 20 mg/ml . . . 50 mg/ml . . . 100 mg/ml, or any values therein).

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions. Additionally, it is also possible to administer the aforesaid pharmaceutical compounds topically and this may be preferably done by way of aqueous solution, liposomal delivery, cream, salve, jelly, paste, ointment and the like, in accordance with the standard pharmaceutical practice.

In some embodiments, G-protein inhibitors of the present invention are delivered to the site of application (e.g. heart) via any acceptable route (e.g. catheter, needle, laparoscopically, surgically, systemically, injection apparatus, etc.). In some embodiments, G-protein inhibitors are delivered via a catheter). In some embodiments, G-protein inhibitors are delivered via an injection apparatus. In some embodiments, G-protein inhibitors are delivered via direct injection. In some embodiments, G-protein inhibitors are applied directly to the site of action. In some embodiments, G-protein inhibitors access the site of action through diffusion, or moving through the vasculature. In some embodiments, G-protein inhibitors are topically applied (e.g. to the heart).

Definitions

To facilitate understanding of the invention, a number of terms are defined below.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins.

As used herein, the term "purified" or "to purify" refers to the removal of contaminants from a sample. For example, recombinant polypeptides are expressed in host cells and the polypeptides are purified by the removal of host cell proteins; the percent of recombinant polypeptides is thereby increased in the sample.

As used herein, the term "vector" is used in reference to nucleic acid molecules that transfer DNA segment(s) from one cell to another. The term "vehicle" is sometimes used interchangeably with "vector." The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. The term "stable transfection" or "stably transfected" refers to the introduction and integration of foreign DNA into the genome of the transfected cell. The term "stable transfectant" refers to a cell that has stably integrated foreign DNA into the genomic DNA. The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of encanine subjectenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "membrane receptor protein" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases is the tyrosine kinases (TKs), which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity. Tyrosine kinases can also be cytoplasmic, non-receptor-type enzymes and act as a downstream component of a signal transduction pathway.

As used herein, the term "signal transduction protein" refers to proteins that are activated or otherwise affected by ligand binding to a membrane or cytostolic receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249-257 (1995)). Typically, GPCRs contain seven transmembrane domains. Putative GPCRs can be identified on the basis of sequence homology to known GPCRs.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

As used herein, the term "subject" refers to any animal (e.g., a mammal), including, but not limited to, humans, non-human primates, canines, rodents, and the like, which is to be the recipient of a particular treatment. Typically, the terms "subject" and "patient" are used interchangeably herein in reference to a human subject, unless indicated otherwise.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxymethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

As used herein, the term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Environmental samples include environmental material such as surface matter, soil, water, and industrial samples. Such examples are not however to be construed as limiting the sample types applicable to the present invention.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

EXAMPLES

The following examples are provided in order to demonstrate and further illustrate certain preferred embodiments and aspects of the present invention and are not to be construed as limiting the scope thereof.

Example 1

Canine Model of Atrial Fibrillation

Sections 1.1 and 1.2 show data from in vivo canine studies that highlight the autonomic profile of the canine PLA—the anatomic region of interest for the proposed studies. These studies demonstrate the heterogeneity of autonomic innervation in the left atrium, with the PVs and PLA showing a characteristic P and S profile. Autonomic nerve bundles (containing both P and S fibers) are preferentially distributed in the PLA. Detailed studies of nerve structure and function in a pacing-induced heart failure model of AF to provide insight into the nature of autonomic remodeling in the setting of structural heart disease that creates conditions for sustained AF. Studies outlined in 1.3 demonstrate evidence of pronounced P as well as S upregulation in the left atrium in the setting of CHF. Studies also demonstrated that autonomic remodeling in the atrium was heterogeneous, with P and S upregulation being more pronounced in the PLA than in the PVs and LAA.

1.1. Autonomic Innervation of the PVs and PLA (Arora et al. Am J Physiol Heart Circ Physiol. 2008; 294(1):H134-144., Arora et al. Heart Rhythm. 2005; 2(1S):S181., Ulphani et al. Journal of the American College of Cardiology. 2005; 45(3):122A., Villuendas et al. J Am Coll Cardiology 2007; 49(9):20A., Villuendas et al. Heart Rhythm. 2007; 4(5S):S169., Ulphani et al. Circulation. 2005; 112(17):II-189., Ulphani et al. Am J Physiol Heart Circ Physiol. 2007; 293(3):H1629-1635., Villuendas. Heterogeneous distribution of Muscarinic receptors contributes to the substrate for Vagal atrial fibrillation: Presented at AHA 2007., herein incorporated by reference in their entirety).

P nerve fibers, and related muscarinic receptors, are preferentially located in the PLA and selective cholinergic blockade in the PLA can be successfully performed to alter vagal AF substrate. PLA, PVs and left atrial appendage (LAA) in canine subjects were immunostained for S nerves (dopamine beta-hydroxylase), P nerves (acetylcholine esterase), and M2 receptors. Epicardial electrophysiologic mapping was performed in 7 additional canine subjects. The PLA was the most richly innervated with nerve bundles containing P and S fibers (PV=0.9±1, PLA=3.2±2.5, LAA=0.17±0.3/cm$^2$; p<0.001); nerve bundles were located in fibrofatty tissue as well as in surrounding myocardium. P predominated over S fibers within bundles (P/S: PV=4.4, PLA=7.2, LAA=5.8). M2 distribution was also most pronounced in the PLA (M2 stained cells/cm$^2$: PLA=17.8±8.3, PV=14.3±7.3, LAA=14.5±8, p=0.012). A particularly high concentration of P fibers was found in the ligament of Marshall (in the PLA). The ligament of Marshall could be traced back to a major branch of the left cervical vagus nerve. The nerve in turn innervates the PVs and the rest of the PLA. The PLA surface is stained for acetylcholinesterase. The cholinergic nerve branches of the vagus nerve are observed to enter the LOM along the left superior PV. A small nerve branch (N) originating in the LOM is seen to innervate the LSPV. White cholinergic nerves originating in the vagus nerve along the LOM are seen to innervate the LSPV and the left inferior PV (LIPV). Cholinergic nerves from the PLA fat pad (PFP) can be seen to innervate the LIPV. A small number of cholinergic nerves from the PLA fat pad can be seen to innervate the right inferior PV (RIPV). Left cervical vagal stimulation (VS) caused significant ERP shortening in all regions, with easily inducible AF. 1% tropicaimide was then applied topically to the PLA. Following tropicaimide application, VS-induced ERP shortening was significantly attenuated not just in the PLA, but also remotely from the site of application at the PV and LAA; AF inducibility decreased by 92% (p<0.001).

Experiments performed during development of embodiments of the present invention demonstrated that autonomic nerves bundles are predominantly located on the epicardial aspect of the left atrium, these bundles show co-localization of P and S elements with the P component predominating in these bundles, P fibers and M2 receptors are preferentially located in the PLA, suggesting an important role for this region in creation of vagal AF substrate, the ligament of Marshall may be an important contributor to the P innervation of the PLA and targeted P blockade in the PLA is feasible and results in an attenuation of vagal responses in the entire left atrium, with a consequent change in AF substrate.

1.2. Autonomic Profile of the Normal PVs and PLA (Arora et al. Journal of the American College of Cardiology. 2007; 49(12):1340-1348., herein incorporated by reference in its entirety)

Experiments performed during development of embodiments of the present invention demonstrated that: the PVs and PLA demonstrate unique activation and repolarization characteristics in response to autonomic manipulation, the heterogeneity of vagal responses correlates with the pattern of $I_{K-ACh}$ distribution in the left atrium, the peculiar autonomic characteristics of the PVs and PLA may create substrate for reentry and AF.

1.3. Autonomic Remodeling in a Canine Model of Atrial Fibrillation (Belin et al. Molecular Basis for Sympathetic Remodeling in the Left Atrium in the Ventricular Tachypacing Canine Model of Congestive Heart Failure: presented at AHA 2007., Villuendas et al. Atrial Autonomic Remodeling in a Canine Model of Congestive Heart Failure: presented at AHA 2007., herein incorporated by reference in their entireties.)

Chronic atrial stretch resulting from pacing-induced CHF results in S and P upregulation in the left atrium, with a resulting increase in AF substrate, and autonomic remodeling in the atria is heterogenous, with S and P remodeling being more pronounced in the PLA than in the rest of the left atrium.

Rapid RV pacing was performed for 3-4 weeks. Progressive atrial and ventricular dilatation was noted on weekly echocardiography. At the end of this period, the animals were euthanized and the PVs and left atrium removed and frozen for further analysis. Tissue from the PLA, PVs and LAA was subjected to immunostaining and western blotting to assess for nerve growth and expression of Gαi2/3, Gαs and Kir3.1 (IKAch). cAMP activity was also assessed in each region. Control tissue was obtained from the same regions from normal control animals. In a group of CHF animals, high-density electrophysiologic mapping was performed in the left atrium prior to euthanasia.

Figure 4:
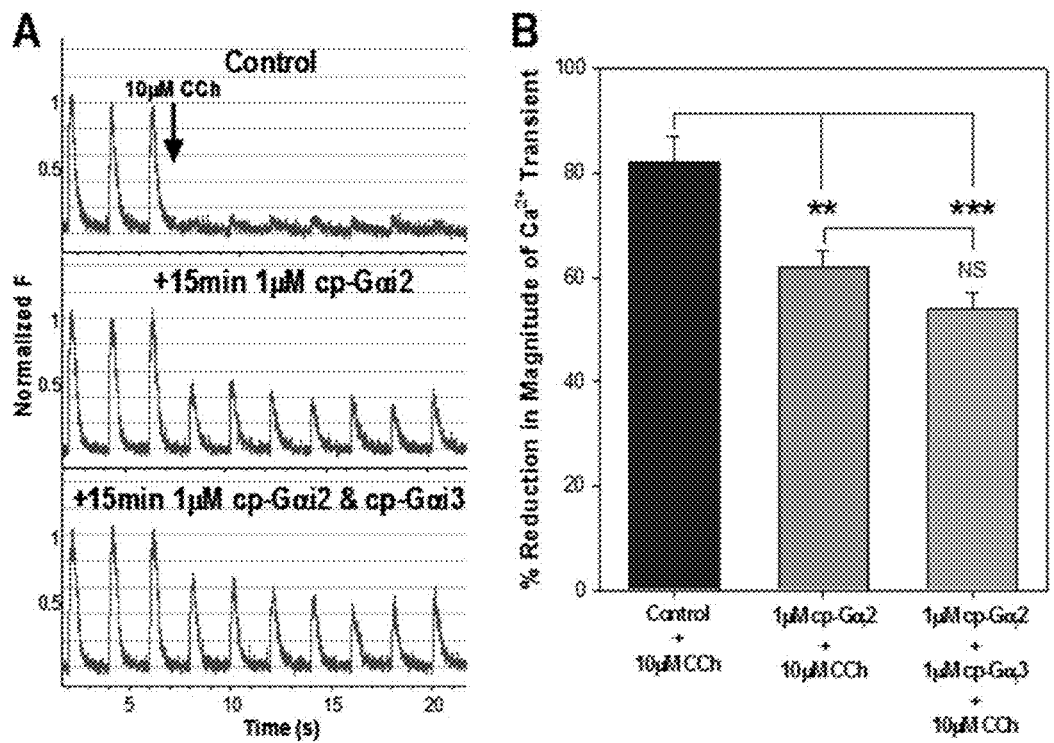
FIG. 4 shows flou-4 fluorescence confocal line-scans and the resultant mean fluorescence integral $F/F_0$ signals (red line tracings above each line-scan image) of $Ca^{2+}$ transients from electrically field-stimulated (0.5 Hz) control and cp-Gαi2/3-exposed or cp-Gαs-exposed individual isolated cardiac myocytes before and after they were superfused with CCh or ISO.
Figure 5:
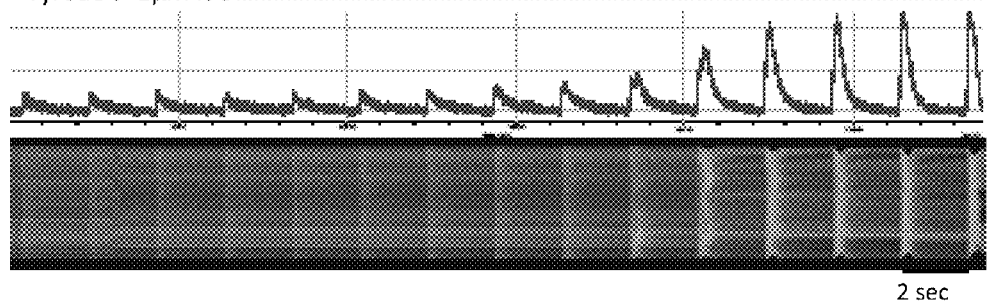
FIGS. 5A and 5B show flou-4 fluorescence confocal line-scans and the resultant mean fluorescence integral $F/F_0$ signals (line tracings above each line-scan image) of $Ca^{2+}$ transients from electrically field-stimulated (0.5 Hz) control and cp-Gαi2/3-exposed or cp-Gas-exposed individual isolated cardiac myocytes before and after they were superfused with CCh or ISO.
Figure 5:
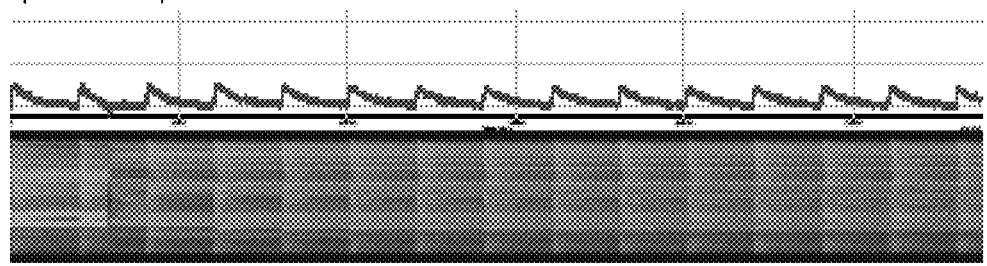
Figure 5:
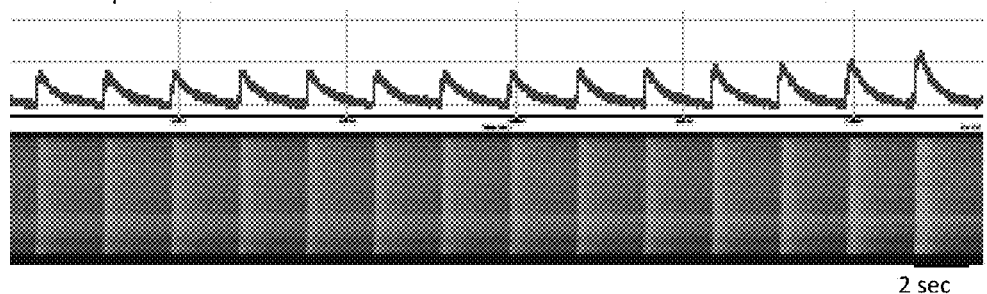
Figure 6:
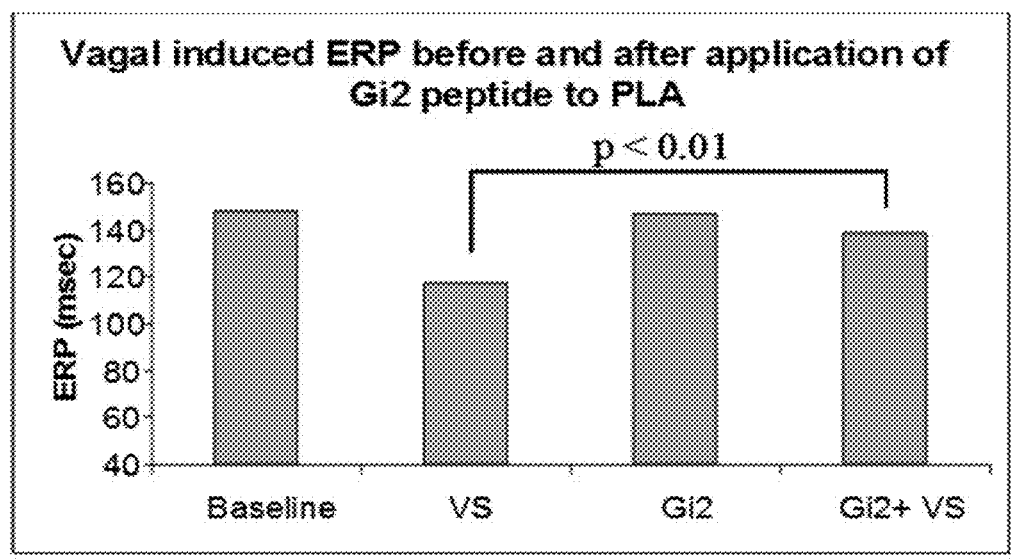
FIG. 6 shows a bar graph of vagal induced ERP before and after the application of G12 peptide to PLA.
Figure 7:
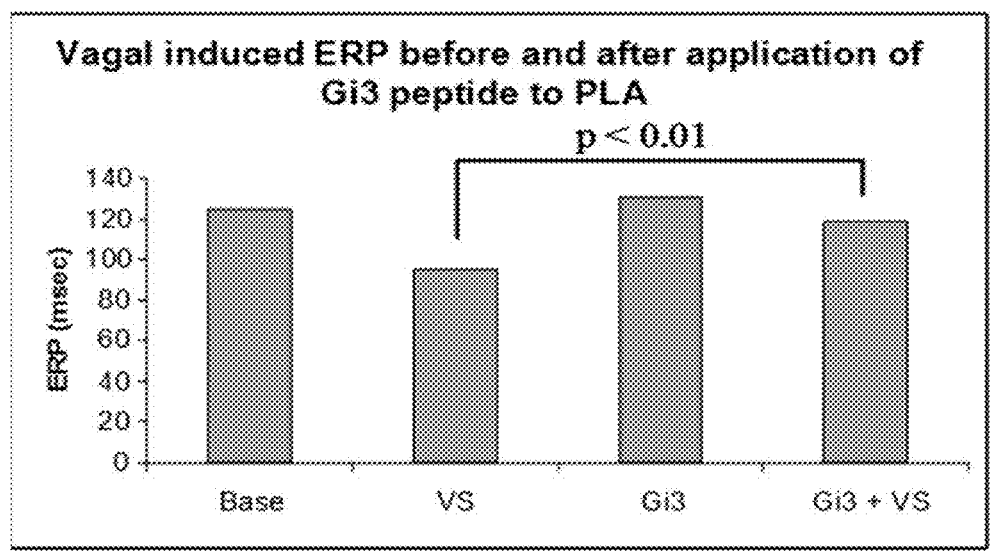
FIG. 7 shows Vagal induced ERP before and after application of Gi3 peptide to PLA
Figure 8:
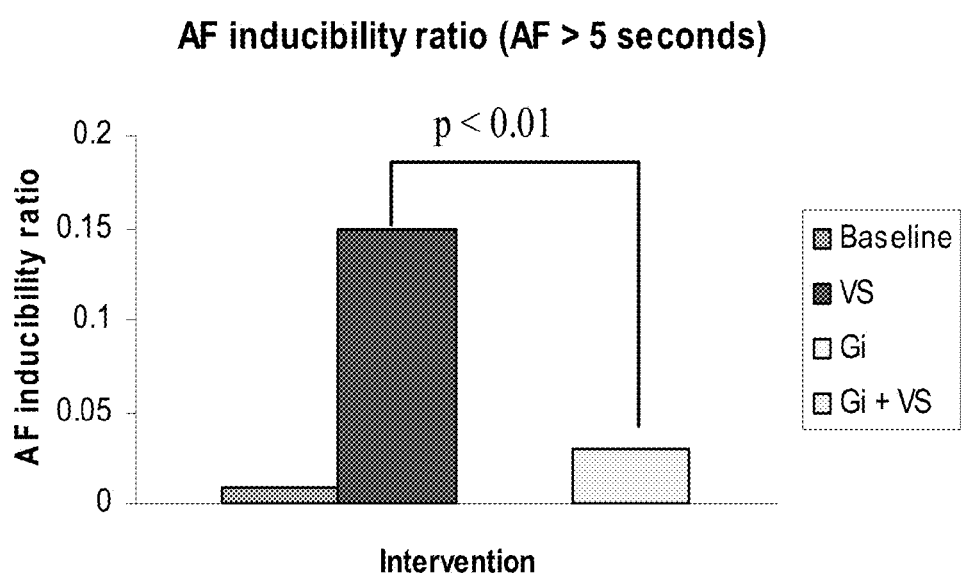
FIG. 8 shows a bar graph of the inducibility.

Significant hyperinnervation was found in the PLA in the setting of CHF, with both ganglion cells and nerve trunks being found in abundance in the PLA from CHF canine subjects (number of nerve trunks in PLA>>PVs and LAA, $p<0.05$). Nerve trunks were significantly larger in CHF canine subjects ($0.12\pm0.15$ cm$^2$ in the controls vs $0.37\pm0.17$ cm$^2$ in the CHF group, $p=0.02$) and consisted of both P and S nerves, with P fibers predominating (P>S, $p<0.05$). Although there was an increase in both S and P nerves, the relative proportion of S fibers appeared to be increased in the setting of CHF (S/PCHF=0.34 vs S/PNORMAL=0.14 in CHF, $p<0.05$). The hyperinnervation in the PLA was accompanied by a significant increase in downstream G-protein expression, with both Gαi (Gαi2, Gαi3) and Gαs being significantly increased in CHF canine subjects as compared to normal canine subjects (SEE FIGS. 1-4). The relative increase in expression of Gαi2, Gαi3 and Gαs was significantly more pronounced in the PLA than in the PVs and LAA; each of these figures shows examples of representative western blots from CHF and normal canine subjects. cAMP activity was also increased in CHF (cAMP$_{CHF}$>cAMP$_{NORMAL}$, $p<0.05$). In CHF canine subjects, cAMP activity was greatest in the PLA (PLA>PV>LAA, $p<0.05$). The expression of the IKAch subunit Kir3.1 in these atria was also assessed, because P effects on atrial refractoriness are primarily driven by IKAch. Kir3.1 expression paralleled the increase in P nerves and Gαi2/Gαi3, being more pronounced in the PLA and PVs than in the LAA (SEE FIG. 4). The increase in Kir3.1 is consistent with the increase in constitutively active IKAch that has been recently described in the setting of chronic AF (Dobrev et al. Circulation. Dec. 13, 2005; 112(24):3697-3706., Ehrlich et al. The Journal of physiology. 2004; 557(Pt 2):583-597., herein incorporated by reference in their entireties). High-density electrophysiologic mapping in CHF canine subjects showed evidence of enhanced vagal responsiveness in these animals. Vagal-induced ERP shortening was more pronounced in CHF canine subjects than in normal canine subjects (SEE FIG. 8). Moreover, ERP shortening in response to VS was more pronounced in the PLA and PVs than in the LAA (SEE FIG. 8).

There is pronounced autonomic remodeling in CHF-induced AF, with evidence of P as well S upregulation in the PVs and left atrium. Both P and S upregulation are more pronounced in the PLA (and to a lesser extent in the PVs) than in the rest of the left atrium. The upregulation of P nerves (and related downstream signaling proteins/ion channels) corresponds with changes in autonomic physiology in the intact left atrium, with total vagal responsiveness being more pronounced in the PLA and PVs than in the rest of the left atrium. The P upregulation noted in the left atrium in CHF is a compensatory response to S upregulation that occurs in response to CHF. Recent studies in the ventricle have in fact demonstrated an increase in Gαi in CHF (Feldman et al. The Journal of clinical investigation. 1988; 82(1):189-197., Brodde et al. Cardiovascular research. 1995; 30(4):570-584., herein incorporated by reference in their entireties)—also thought to be a compensatory response to worsening CHF. However, since normal atria are more densely innervated with vagal fibers (than the ventricle) and also contain a significant amount of IKAch, the compensatory response is likely to be more vigorous in the atrium. The compensatory increase in vagal innervation (and resulting increase in IKAch) that we have described appears to contribute significantly to increased AF substrate.

Figure 9:
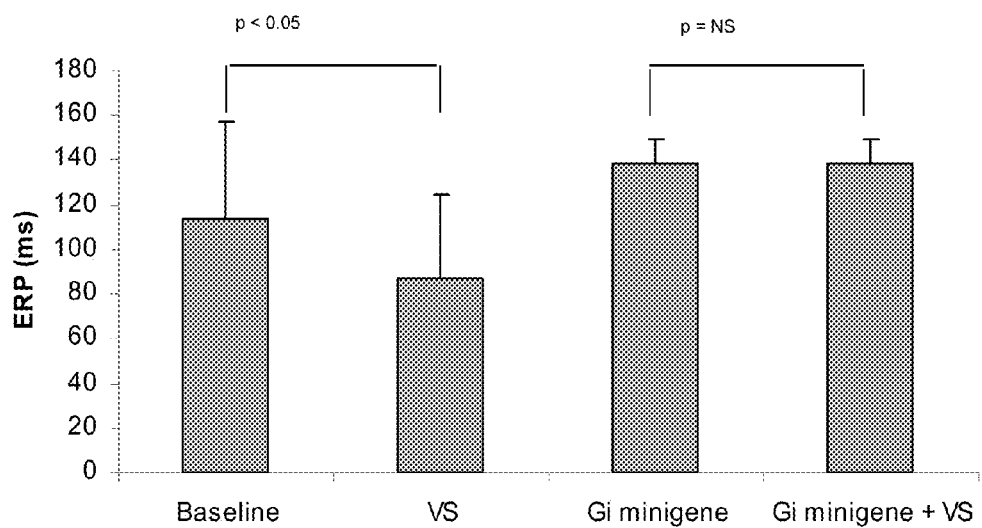
FIG. 9 shows a bar graph of VS-induced ERP shortening at baseline and following VS Gi minigene, or VS and Gi minigene treatment.
Figure 10:
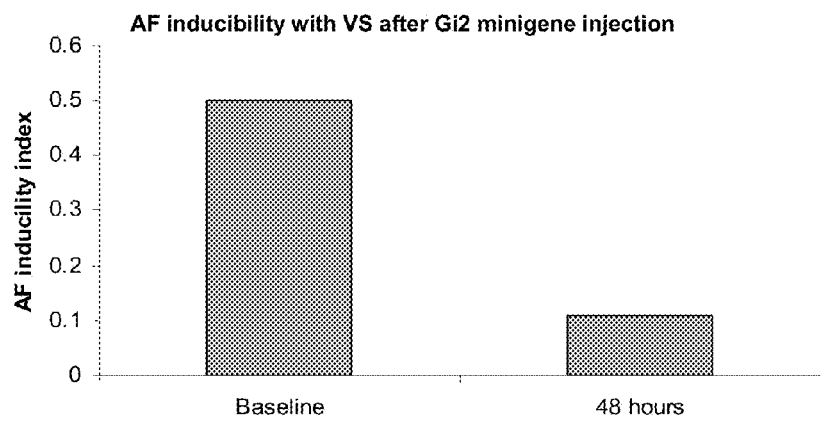
FIG. 10 shows a bar graph of AF inducibility with VS after Gi2 minigene injection.

1.4 Topical Denervation of the PLA—Effects on the Autonomic Physiology of the Left Atrium Using the canine model outlined below, 1% tropicaimide (a cholinergic blocker) was applied topically to the epicardial aspect of the PLA in canine subjects. Effective refractory periods were measured at multiple sites in the PLA a) at baseline, b) after left vagal stimulation, c) after tropicaimide application to the PLA and d) in the presence of vagal stimulation after tropicaimide application. Vagal stimulation led to significant ERP shortening as compared to baseline (SEE FIG. 9). The shortening in response to vagal stimulation was either entirely eliminated or at least significantly attenuated after the application of tropicaimide. AF was initially easily inducible in the presence of vagal stimulation with extra-stimulus testing from the PLA; after tropicaimide application, AF could not induced with extrastimulus testing, in the presence or absence of vagal stimulation (SEE FIG. 10). These results demonstrate the feasibility of a topical approach in causing selective parasympathetic (or sympathetic) denervation in the PLA, and a role for the parasympathetic nerves of the PLA in creating substrate for AF. The robust autonomic profile of the PLA and its role in AF (both in normal as well as diseased hearts), thereby making it an attractive target for autonomic manipulation by regional delivery of Gα C-terminal peptides.

Example 2

G-Protein Inhibitors

Peptides corresponding to the C-terminus of Gα subunits can be used as competitive and specific inhibitors of receptor-G-protein interactions (Gilchrist et al. J Biol. Chem. 1998; 273:14912-14919., Ellis et al. J Biol Chem. 1999; 274:13719-13727., Gilchrist et al. J Biol Chem. 1999; 274:6610-6616., Gilchrist et al. Methods Enzymol. 2002; 344:58-69., Gilchrist et al. Sci STKE. 2002; 5:PL1., herein incorporated by reference in their entireties). Section 2.1 provides in vitro studies that demonstrate the use of Gα C-terminal peptides to block Gαi with resulting inhibition of downstream effects. Gα C-terminal peptides (Gαs and Gαi2/3) that have been tagged with a cell-penetrating poly-arginine sequence have the ability to cross canine cardiomyocyte cell membranes. These peptides have been shown to penetrate cells and to successfully cross cardiomyocyte cell membranes. Experiments were performed to examine the effects of GαC-terminal peptides on the electrophysiology of isolated atrial cardiomyocytes. Section 2.2 provides data demonstrating that CP-Gαi peptide can attenuate cholinergic as well as adrenergic influences on the Ca$^{2+}$ dynamics of left atrial cardiomyocytes. Experiments were performed during development of embodiments of the present invention to further characterize the therapeutic role of regional P or S denervation on AF substrate. Section 2.3 demonstrates successful intracellular delivery of CP Gαi peptide in the PLA in intact canine subjects. Section 2.4, demonstrates successful vagal denervation in the left atrium following application to the PLA of CP-Gαi peptide and Gαi peptide-expressing minigene (plasmid).

2.1. Use of GαC-Terminal Peptides to Dissect Signaling Pathways

The C-terminal region of Gα subunits represents an important site of interaction between heterotrimeric G-proteins and their cognate receptors. Studies in HEK 293 cells as well as other studies (Gilchrist et al. Sci STKE. 2002; 5:PL1., Ellis et al. The Journal of biological chemistry. 1999; 274(19): 13718-13727., Gilchrist et al. The Journal of biological chemistry. 1999; 274(10):6610-6616., Gilchrist et al. Sci STKE. 2002; 2002(118):PL1., Gilchrist et al. Methods in enzymology. 2002; 344:58-69., herein incorporated by reference in their entireties) indicate that the Gαi carboxyl terminus minigene constructs encoding the carboxyl terminal 11 amino acid residues from Gα subunits can completely block M2 mAChR-mediated K+ channel activation. The inhibition is specific, as constructs producing Gαs, Gαq, or a scrambled Gαi carboxyl terminal peptide had no effect. The results indicate that peptides expressed by minigene vectors are selective in their ability to inhibit the correct G-protein signaling pathway. Poly-arginine tails were used to provide cell-penetrating properties (Futaki et al. The Journal of biological chemistry. 2001; 276(8):5836-5840., Mitchell et al. J Pept Res. 2000; 56(5):318-325., Thoren et al. Biochemical and biophysical research communications. 2003; 307(1):100-107., herein incorporated by reference in their entireties). A chimeric peptide was synthesized that possesses an N-terminal sequence with membrane-penetrating activity and a C-terminal sequence corresponding to the last 11 residues of Gα$_s$ or Gα$_i$. Cell penetration of these peptides into canine subject atrial myocytes was verified by anti-FLAG Western blot assay of cell lysates prepared from canine subject atrial cardiomyocytes incubated with FLAG-tagged versions of cp-Gs or cp-Gi peptides (0.04-5 μM for 60 min). Toxicity of these peptides as assayed by rapid automated tetrazolium dye based assay (MTT) indicated that 5 μM Gs peptide caused ~4% decrement in cell viability, whereas 5 μM Gi peptide resulted in ~8% enhancement of cell viability.

2.2. Effect of cp-Gα Peptides on Cholinergic and β-Adrenergic Modulation Intracellular Calcium Dynamics in Isolated Canine Atrial Myocytes. (Arora et al. *Heart Rhythm.* 2007; 4(5S):S9., herein incorporated by reference in its entirety)

Figure 11:
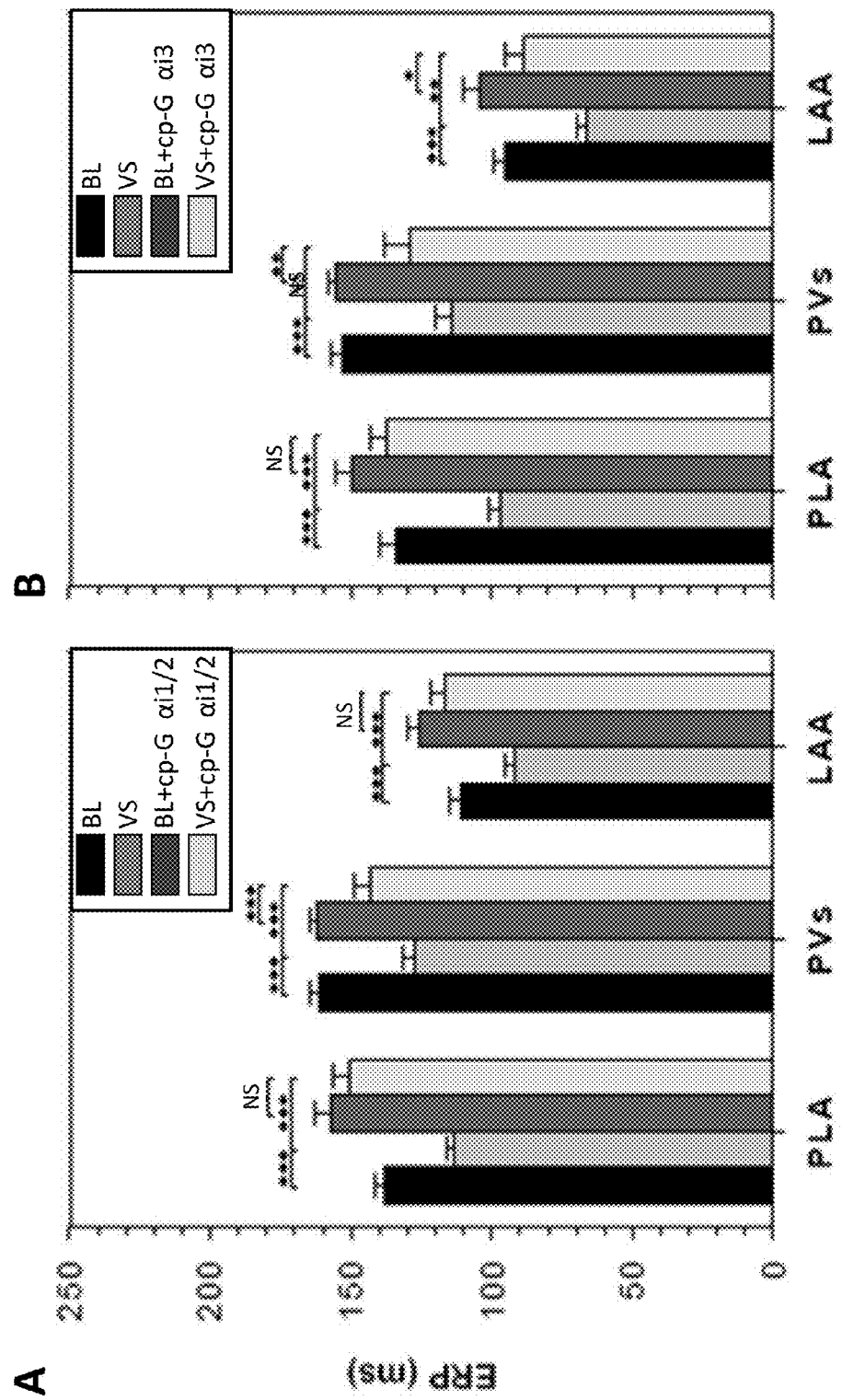
FIG. 11 shows bar graphs of ERP shortening in the PLA, PVs, and LAA.
Figure 11:
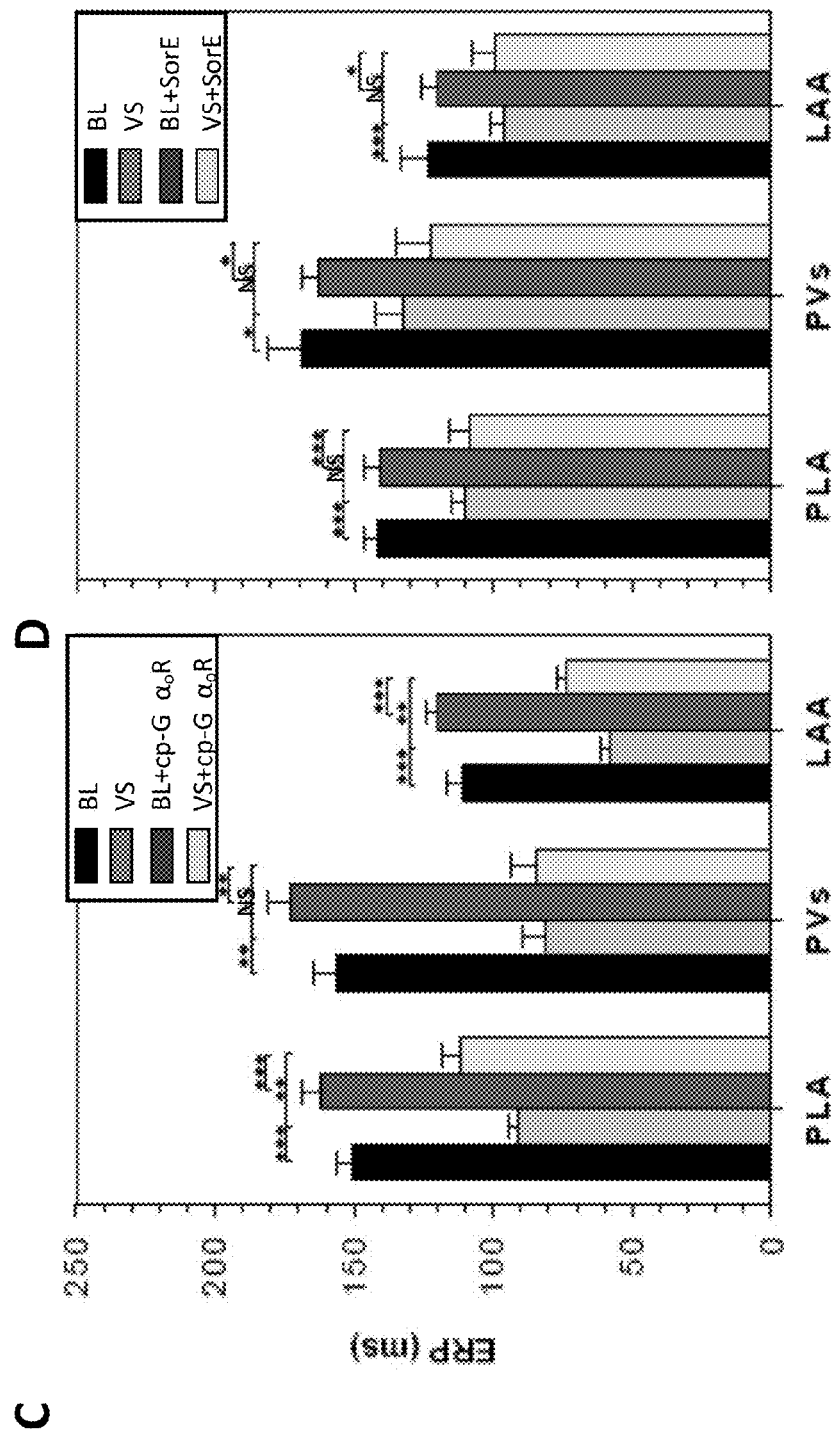
Figure 12:
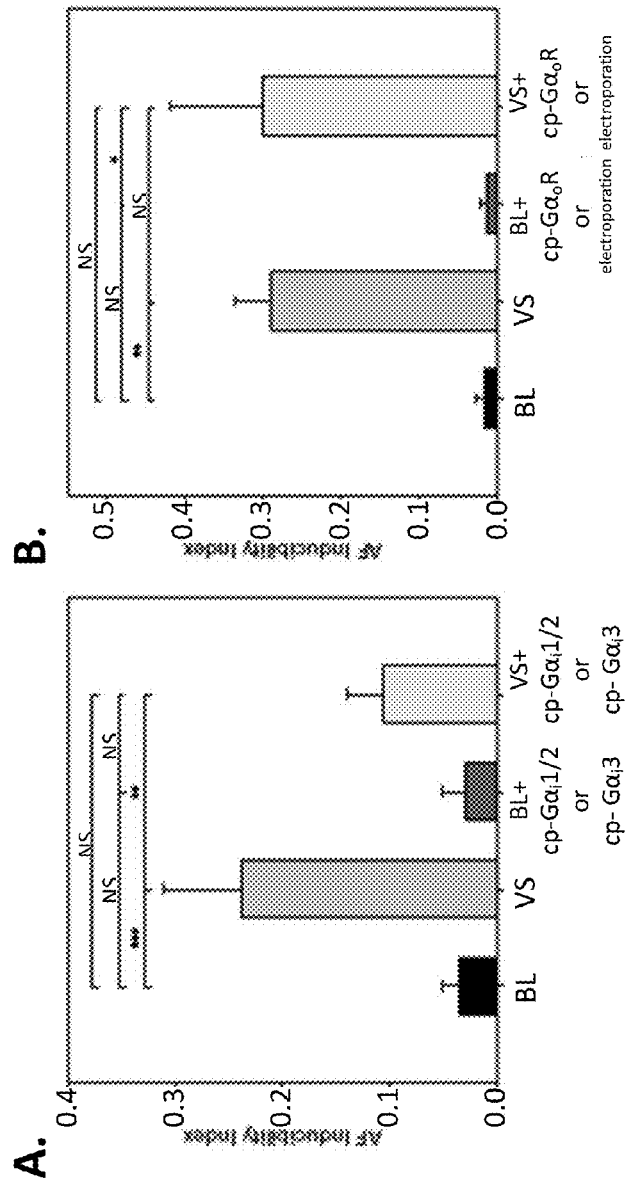
FIG. 12 shows a statistical summary of AF inducibility
Figure 13:
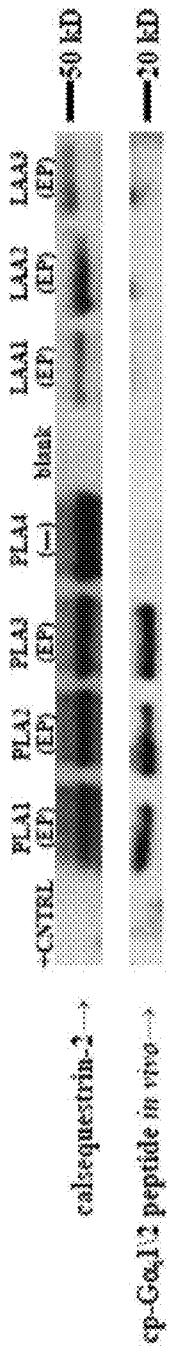
FIG. 13 shows an Anti-FLAG Western blot assay.
Figure 15:
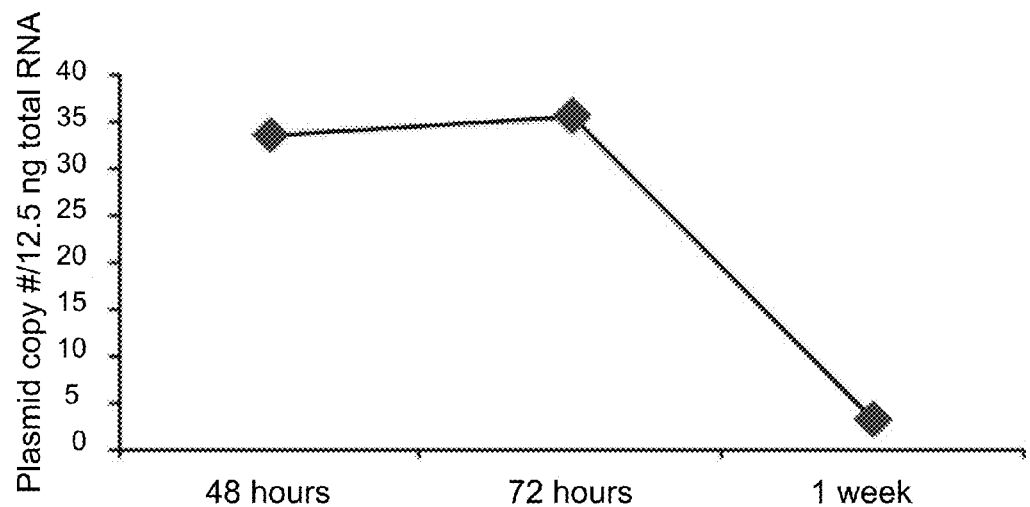
FIG. 15 shows relative expression of Gαi1/2 minigene at 48 hours, 72 hours and 1 week.

Cardiac myocytes were isolated from the canine left atrium, loaded with fluo-4 (fluorescent Ca$^{2+}$ indicator), and electrically field-stimulated. Fluorescence confocal microscopy was used to record cellular Ca$^{2+}$ transients from control cells and cells exposed to either cp-Gαi2, or cp-Gαs peptide (10-20 min constant focal superfusion of 0.1-3 μM peptide) before and after focal superfusion of the M2 receptor (M2R) agonist, carbachol (CCh), or the β-adrenergic receptor (βAR) agonist, isoproterenol (ISO). Cellular Ca$^{2+}$ transients were nearly eliminated within a few seconds of 10 μM CCh (M2R saturating concentration) administration—consistent with M2R-stimulated Gi activation and its membrane-delimited (fast) activation of I$_{K-ACh}$ effecting negative inotropy (SEE FIG. 11A). However, this shows that cp-Gαi2 peptide can significantly attenuate such CCh effect on Ca$^{2+}$ transients (SEE FIG. 11B). Co-administration of equal doses of cp-Gαi2 and cp-Gαi3 have a synergistic effect on CCh modulation of Ca$^{2+}$ cycling in PLA myocytes (SEE FIG. 15). CCh results in near-elimination of the Ca$^{2+}$ transients (SEE FIG. 12A, top panel). The addition of cp-Gαi2 (middle panel) attenuates CCh effect on the Ca$^{2+}$ transients. A combination of cp-Gαi2 and cp-Gαi3 (SEE FIG. 12A, lowest panel) causes more attenuation of the Ca$^{2+}$ transient than cp-Gαi2 alone (albeit less than a doubling of effect). The effects can be summarized quantitatively (SEE FIG. 12B). Ca$^{2+}$ transients were appreciably augmented within 20-30 seconds of 1 μM ISO (βAR saturating concentration) administration—consistent with βAR-stimulated Gs activation and subsequent (slower) initiation of the cAMP-PKA signaling cascade effecting positive inotropy (SEE FIG. 13A). However, cp-Gαs peptide can significantly attenuate such ISO effect on Ca$^{2+}$ transients (SEE FIG. 13B). These results demonstrate that G-protein inhibition can successfully modify cholinergic as well as adrenergic influences on the E-C coupling characteristics of atrial cardiomyocytes.

2.3. Demonstration of Intracellular Peptide Delivery after the Application of Gαi Peptide to the PLA.

Peptides were FLAG-tagged prior to in vivo use. The peptide (200 nM-1 μM) was then applied topically to the surface of the PLA, followed by electroporation. After the animal was sacrificed, the PLA was sectioned and immunohistochemical staining was performed for FLAG FLAG/Gαi2 peptide appears stained in epicardial myocytes of the PLA. FLAG/peptide appears within the cells on the epicardial aspect of the PLA. FLAG/Gαi3 peptide appears stained in epicardial myocytes of the PLA.

2.4. Topical Denervation of the PLA with Cp-Gαi Peptide: Effects on the Autonomic Physiology of the Left Atrium and AF Substrate (Arora et al. Heart Rhythm. 2007; 4(5S): S9., herein incorporated by reference in its entirety).

Figure 14:
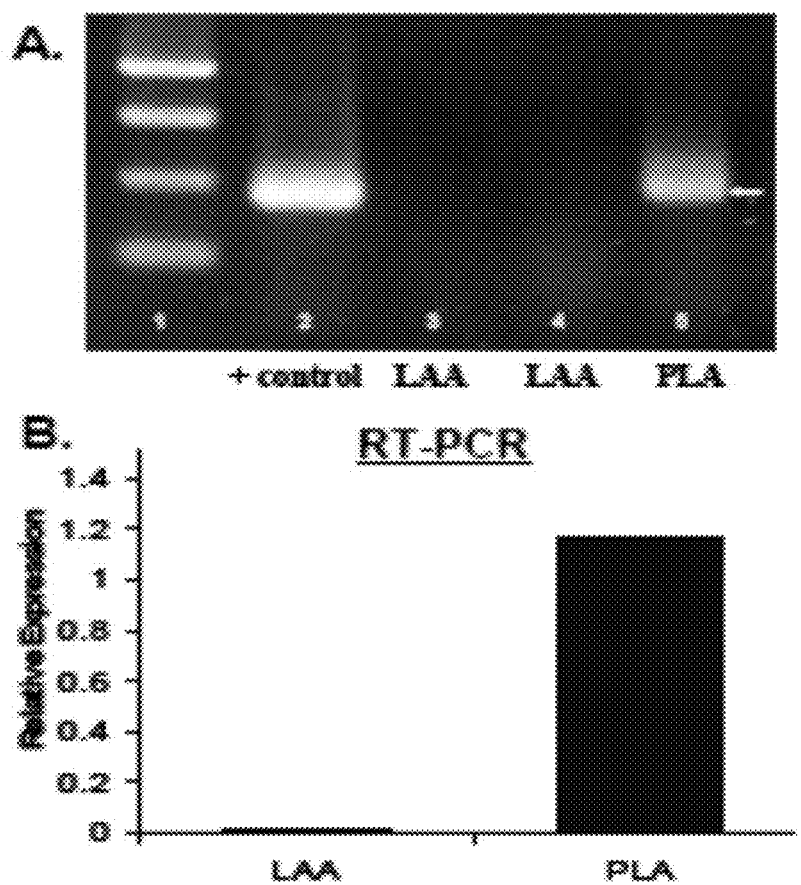
FIG. 14 shows the results of PCR on PLA tissue that had been injected with the minigene plasmid; Lane 1: marker (1 kb ladder), Lane 2: positive control (Gαi1/2 plasmid), Lanes 3 and 4: tissue taken from right atrial appendage (remote from minigene plasmid injection site, control), Lanes 5: presence of minigene mRNA in PLA tissue (434 bp and denoted by yellow arrow.
Figure 16:
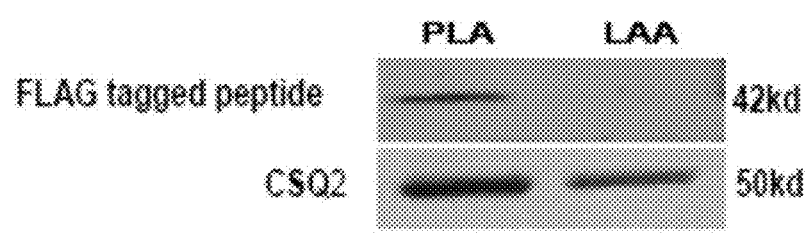
FIG. 16 shows a representative western blot for FLAG-tagged Gαi peptide (48 hours after gene injection).
Figure 18:
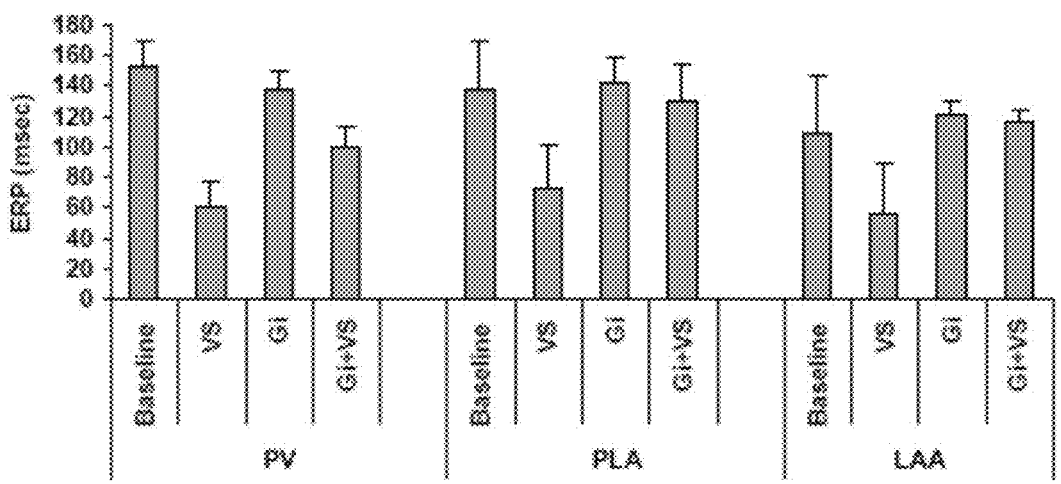
FIG. 18 shows bar graph of the effect of Gαi1/2 minigene on vagal-induced ERP shortening at the injection site (PLA) and remote sites (PPVs and LAA).
Figure 19:
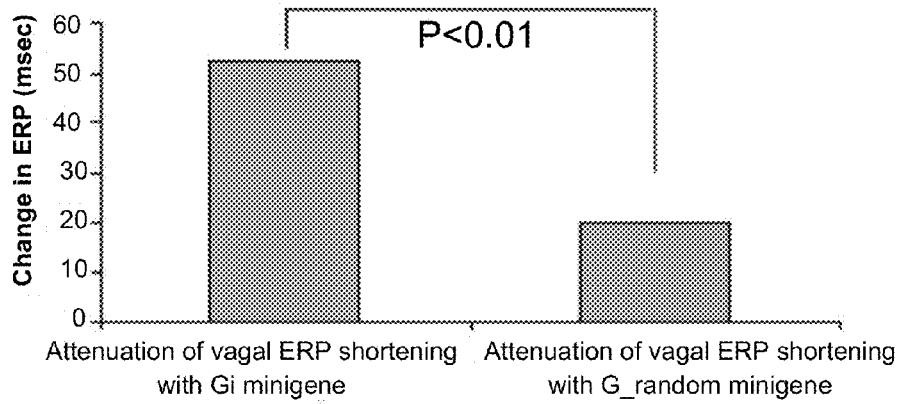
FIG. 19 shows a graph of the change in ERP shortening in response to Gi minigene or random minigene.

High-density epicardial mapping was performed in the PVs (2×2 electrodes), the PLA (7×3 electrodes) and the left atrial appendage (LAA) (7×3 electrodes) of canine subjects. Effective refractory periods (ERPs) were obtained at baseline and in response left cervical vagal stimulation (VS) (20 Hz). Cp-Gαi2 peptide (200-330 nM) was then applied topically to the epicardial aspect of the PLA in a canine subgroup. Cp-Gαi3 peptide (200-330 nM) was then applied topically to the epicardial aspect of the PLA of a second subgroup. Electroporation was performed after the application of peptide to enhance intracellular delivery of the peptide. ERPs were then re-measured in the presence and absence of VS. VS led to significant ERP shortening in the PV, PLA and LAA as compared to baseline (baseline vs. VS for each region, p<0.05; SEE FIGS. 18 and 19). VS induced ERP shortening was significantly attenuated not just in the PLA but also in the PV and LAA after the application of either cp-Gαi2 or cp-Gαi3 peptide to the PLA (Gi+VS>>VS, p<0.05; SEE FIGS. 14 and 15). AF was initially easily inducible in the presence of VS with extrastimulus testing; after the application of cp-Gαi peptide, AF induciblity was significantly decreased (SEE FIG. 16). These results demonstrate the use of a topical, G-protein based approach achieving selective P denervation in the PLA, with a resulting change in vagal responsiveness in the entire left atrium.

2.5. Topical Denervation of the PLA with Gαi Peptide-Expressing Minigene Plasmid: Effects on the Autonomic Physiology of the Left Atrium.

Figure 17:
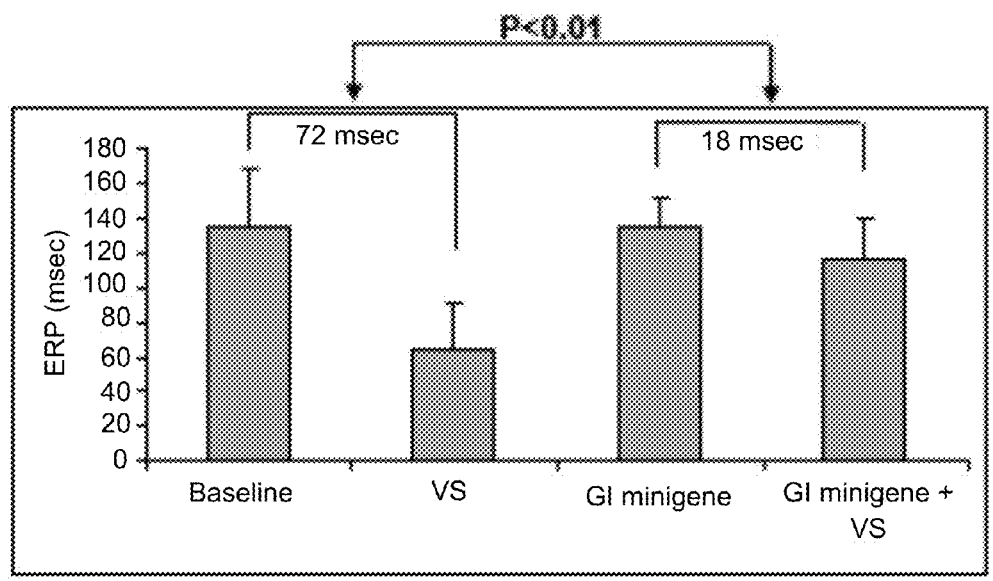
FIG. 17 shows bar graph of the effects of Gαi1/2 minigene on vagal-induced ERP shortening.

In canine subjects, high-density epicardial mapping was performed. After baseline mapping, 500 mcg Gαi minigene was injected in the PLA. The PLA was then subjected to electroporation. Epicardial mapping was performed again within 48 hours after injection of the minigene. The animal was then euthanized and atrial tissue was frozen. RNA was isolated from frozen heart tissue; 500 ng RNA was used for reverse transcription. One-fifth of the cDNA was subjected to PCR. PCR products were resolved on a 1% agarose gel. In 1 animal, GFP-expressing minigene plasmid was injected in the PLA and electroporation performed. Atrial tissue was frozen and subjected to fluorescence microscopy to assess for GFP expression. Significant VS-induced ERP shortening was noted at baseline in each canine subject (SEE FIG. 17). However, VS-induced ERP shortening was significantly attenuated after Gαi minigene injection. Vagal-induced AF inducibility was also significantly diminished after Gα minigene injection (SEE FIG. 18). PCR amplification was performed on nucleic acid recovered from PLA tissue that had been injected with the minigene plasmid SEE FIG. 19). In the animal receiving GFP-minigene, atrial tissue was examined for GFP expression 48 hours after minigene injection. GFP expression was noted in a large number of cardiomyocytes throughout the posterior right atrium. These results demonstrate the use of a topical, minigene-based approach in achieving Gαi inhibition in the PLA, with a resulting change in vagal responsiveness in the entire left atrium.

Experiments performed during development of embodiments of the present invention demonstrate the robust autonomic profile of the PLA in normal hearts and its potential role in AF, thereby making it a target for autonomic manipulation by regional delivery of Gα C-terminal peptides. The importance of the PLA is further heightened by the observation that targeted P blockade in the PLA with a cholinergic blocker results in an attenuation of vagal responses not just in the PLA but in the entire left atrium, with a consequent change in AF substrate. Pronounced autonomic remodeling is noted in the setting of heart failure-induced AF, with evidence of significant S as well as P nerve growth. This nerve growth is preferentially localized to the PLA and is accompanied by a significant increase in expression of the signaling molecules that mediate S and P effects in the atria. The preferential increase in expression of Gαi as well as Gαs in the PLA makes this region a suitable target for S and/or P denervation using regionally—directed G-protein inhibition. C-terminal peptides from Gα can be used to selectively block G-protein signaling that is specific to autonomic pathways. Membrane transfer of cp-Gαi or Gαs peptide can be successfully achieved in cardiomyocytes, with resulting downstream electrophysiologic effects. Topical application of cp-Gαi peptide to the PLA can successfully modify substrate for vagal AF. Topical injection of Gαi minigene in the PLA results in Gαi peptide production, with successful modification of vagal AF substrate.

Example 3

Sections 3.1 and 3.2 provide in vivo canine studies that demonstrate the autonomic profile of the canine PLA. Experiments performed during development of embodiments of the present invention highlight the heterogeneity of autonomic innervation in the left atrium, with the PVs and PLA showing a characteristic P and S profile. Autonomic nerve bundles, containing both P and S fibers, are preferentially distributed in the PLA.

Peptides corresponding to the C-terminus of Gα subunits were used as competitive and specific inhibitors of receptor-G-protein interactions. In experiments performed during development of embodiments of the present invention, in-vitro and in-vivo experiments, with cell-penetrating (CP)—Gαi peptides. Gα C-terminal peptides (Gαs and Gαi2/3) synthesized with a poly-arginine sequence have the ability to cross canine cardiomyocyte cell membranes to examine the potential for Gαi peptides to inhibit parasympathetic signaling in the atria. CP-Gαi and CP-Gαs peptides can attenuate cholinergic as well as adrenergic influences on the Ca2+ dynamics of left atrial cardiomyocytes. In vivo experiments were performed explore therapeutic role of regional parasympathetic (P) or sympathetic (S) denervation on AF substrate. Section 3.3 demonstrates successful intracellular delivery of CP Gαi peptide in the PLA in intact canine subjects, with resulting attenuation of vagal responsiveness in the entire left atrium. The success of acutely delivered Gαi peptides in inhibiting parasympathetic signaling in the left atrium demonstrated the utility of using minigenes expressing Gα peptides. Experiments in intact animals (Section 3.4), demonstrate that injection of minigenes expressing Gαi peptides into the PLA results in: successful transcription of the minigene with production of Gαi peptide and inhibition of vagal responsiveness in the entire left atrium. Experiments were performed with a minigene under the control expressing a CMV promoter, which allowed robust gene expression for up to 72 hours following gene injection. For long-term expression, experiments were performed with a minigene under the control of a long-acting, human polyubiquitin C (UbC) promoter. Section 3.5 demonstrates transcription of minigene at 2 and 3 weeks following gene injection in the PLA. Detailed studies of nerve structure and function in a pacing-induced heart failure model of AF were performed. These studies (Section 3.6) demonstrate evidence of pronounced P as well as S upregulation in the left atrium in the setting of CHF. The autonomic remodeling in the atrium was heterogeneous, with P and S upregulation being more pronounced in the PLA than in the PVs and LAA. The relative importance of the PLA in autonomic remodeling makes it suitable to targeted G-protein inhibition as a way to selectively inhibit P and/or S signaling in the latrium.

3.1. Autonomic Innervation of the Normal PVs and PLA

P nerve fibers, and related muscarinic receptors, are preferentially located in the PLA and that scholinergic blockade in the PLA can be successfully performed to alter vagaAF substrate. PLA, PVs and left atrial appendage (LAA) from canine subjects were immunostained for S nerves (dopamine beta-hydroxylase), nerves (acetylcholine esterase), and M2 receptors. Epicardial electrophysiologic mapping was performed in an additional group of canine subjects.

The PLA was the most richly innervated with nerve bundles containing P and S fibers (PV=0.9±1, PLA=3.2±2.5, LAA=0.17±0.3/cm$^2$; p<0.001); nerve bundles were located in fibrofatty tissue as well as in surrounding myocardium. P predominated over S fibers within bundles (P/S: PV=4.4, PLA=7.2, LAA=5.8). M2 distribution was also most pronounced in the PLA (M2 stained cells/cm$^2$: PLA=17.8±8.3, PV=14.3±7.3, LAA=14.5±8, p=0.012). A particularly high concentration of P fibers was found in the ligament of Marshall (in the PLA). The ligament of Marshall could be traced back to a major branch of the left cervical vagus nerve. This nerve innervates the PVs and the rest of the PLA. The PLA surface is stained for acetylcholinesterase. The cholinergic nerve branches of the vagus nerve enter the LOM along the left superior PV. A small nerve branch (N) originating in the LOM is seen to innervate the LSPV. White cholinergic nerves originating in the vagus nerve along the LOM are seen to innervate the LSPV and the left inferior PV (LIPV). Cholinergic nerves from the PLA fat pad (PFP) can be seen to innervate the LIPV. A small number of cholinergic nerves from the PLA fat pad can be seen to innervate the right inferior PV (RIPV). Left cervical vagal stimulation (VS) caused significant ERP shortening in all regions, with easily inducible AF. 1% tropicaimide was then applied topically to the PLA. Following tropicaimide application, VS-induced ERP shortening was significantly attenuated not just in the PLA, but also remotely from the site of application at the PV and LAA; AF induciblity decreased by 92% (p<0.001). Autonomic nerves bundles are predominantly located on the epicardial aspect of the left atrium. These bundles show co-localization of P and S elements, with the P component predominating in these bundles. P fibers and M2 receptors are preferentially located in the PLA, suggesting an important role for this region in creation of vagal AF substrate. The ligament of Marshall may be an important contributor to the P innervation of the PLA. Targeted P blockade in the PLA is feasible and results in an attenuation of vagal responses in the entire left atrium, with a consequent change in AF substrate.

3.2. Unique Autonomic Profile of the Normal PVs and PLA6

Experiments performed during development of embodiments of the present invention demonstrate that the PVs and PLA demonstrate unique activation and repolarization characteristics in response to autonomic manipulation. The heterogeneity of vagal responses correlates with the pattern of $I_{K-ACh}$ distribution in the left atrium. The peculiar autonomic characteristics of the PVs and PLA may create substrate for reentry and AF.

3.3. Topical Denervation of the PLA with Cp-Gαi Peptide: Effects on the Autonomic Physiology of the Left Atrium and AF Substrate.

Parasympathetic signaling is primarily mediated by an inhibitory heterotrimeric G-protein, Gαiβγ. Targeted inhibition of $G\alpha_i$ interactions in the posterior left atrium (PLA) can modify substrate for vagal AF.

3.3.A. Use of GαC-terminal Peptides to Dissect Signaling Pathways

The C-terminal region of Gα subunits represents an important site of interaction between heterotrimeric G-proteins and their cognate receptors. In HEK 293 cells, the Gαi carboxyl terminus minigene constructs encoding the carboxyl terminal 11 amino acid residues from Gα subunits can completely block M2 mAChR-mediated K+ channel activation. The inhibition appears specific as constructs producing Gαs, Gαq, or a scrambled Gαi carboxyl terminal peptide had no effect. The results indicate the peptides expressed by minigene vectors are selective in their ability to inhibit the correct G-protein signaling pathway. A chimeric peptide that possesses a polyarginine tail leads to cell-penetrating properties and an N-terminal sequence with membrane-penetrating activity and a C-terminal sequence corresponding to the last 11 residues of $G\alpha_s$ or $G\alpha_i$. Cell penetration of these peptides into canine subject atrial myocytes was verified by anti-FLAG Western blot assay of cell lysates prepared from canine subject atrial cardiomyocytes incubated with FLAG-tagged versions of cp-Gs or cp-Gi peptides (0.04-5 µM for 60 min). Toxicity of these peptides as assayed by rapid automated tetrazolium dye based assay (MTT) indicated that 5 µM Gs peptide caused ~4% decrement in cell viability, whereas 5 µM Gi peptide resulted in ~8% enhancement of cell viability.

3.3.B. Effects cp-Gαi Peptide on the Autonomic Physiology of the Left Atrium and AF Substrate.77

In canine subjects, high-density epicardial mapping was performed in the PVs (2×2 electrodes), the PLA (7×3 electrodes) and the left atrial appendage (LAA) (7×3 electrodes). Effective refractory periods (ERPs) were obtained at baseline and in response left cervical vagal stimulation (VS) (20 Hz). FLAG-tcp-Gα peptides (200 nM-3 µM of cp-Gα$_i$1/2 (N=8 canine subjects), cp-Gα$_i$3 (N=4 canine subjects), or random-sequence cp-Gα$_o$R peptide (N=3 canine subjects) were injected into the PLA epicardium of the canine subjects followed by either sonoporation or electroporation. In a subgroup of the canine subjects, sonoporation or electroporation alone was performed without introduction of cp-Gα$_i$ peptide. ERPs were then re-measured in the presence and absence of VS. In a separate set of control animals, ERPs were measured before and after the administration of systemic autonomic blockade with propranolol (0.2 mg/kg)+atropine (0.04 mg/kg).

Figure 20:
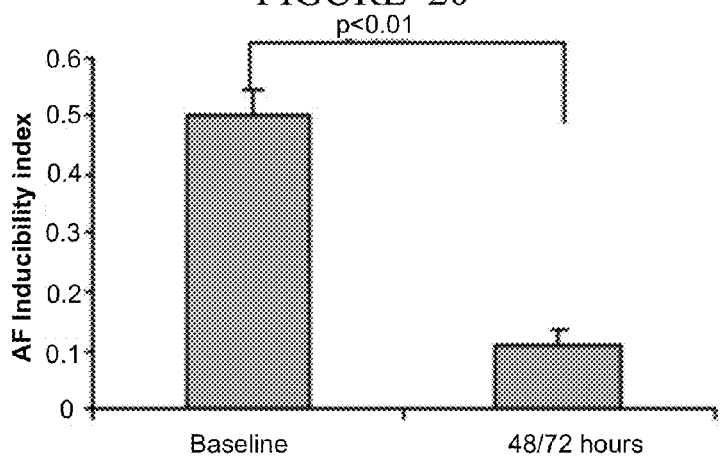
FIG. 20 shows a graph of vagal-induced AF inducibility upon Gα1/2 minigene injection.

At baseline, VS caused significant ERP shortening in each region i.e. PLA, PV and LAA (SEE FIG. 20). Sonoporation or electroporation of target PLA sites without concomitant peptide injection caused no overt permanent changes to electrogram characteristics, and had no significant effect on PLA, PV and LAA ERPs at baseline (BL) or during VS (SEE FIG. 20). Furthermore, histological analysis of left atrial tissue samples, including the PLA, taken after in vivo electrophysiology experiments showed no evidence of myocyte necrosis. There was no change in ERP heterogeneity, as assessed by coefficient of variation of all ERPs in PLA, after cp-Gαi application. No atrial or ventricular arrhythmias were induced by the peptide injection with or without sono\electroporation manoeuvre in-and-of itself. All animals remained hemodynamically stable throughout experiments. Because peptide delivery was localized to sites in the PLA, effects of the peptide on atrial refractoriness were expected to be most prominent in the PLA. Indeed, the pronounced VS-induced ERP shortening was eliminated in the PLA after peptide delivery. However, changes in atrial refractoriness after peptide delivery were not confined to the PLA. Elimination of VS-induce ERP shortening and prolongation of BL ERPs also occurred in the LAA after peptide delivery. Moreover, ERPs during VS were prolonged in all left atrial regions after peptide delivery.

Effects of injecting FLAG-tagged cp-Gα$_i$3 peptide into the PLA followed by electroporation were quite similar to that of cp-Gα$_i$1\2 (SEE FIG. 20). In the PLA, the pronounced VS-induced ERP shortening was eliminated and ERPs at BL were prolonged after cp-Gα$_i$3 peptide delivery. Likewise, effects were not confined to the PLA, as VS-induced ERP shortening was reduced also in the LAA after peptide delivery. Gα$_i$ inhibitory peptides have an essential Cys in their sequence that, via possible disulfide bond formations with other PLA constituent proteins having accessible Cys of their own, could indirectly cause some effect on autonomic signaling. Cys-containing Gα$_o$ random-sequence peptide, Gα$_o$R, was delivered into the PLA canine subjects followed by electroporation, and ERPs were subsequently measured in the PLA, PVs and LAA to measure this effect. After Gα$_o$R peptide delivery into the PLA, a small but statistically significant prolongation of ERPs during VS was evident in the PLA and LAA, although there was still greatly significant VS-induced ERP shortening (SEE FIG. 20C) unlike that induced by either cp-Gα$_i$1\2 or cp-Gα$_i$3 peptides. This small effect of cp-Gα$_o$R represents the non-specific action of the Gα$_i$ peptides on left atrial ERPs. This effect is insignificant when compared with the effect of cp-Gα$_i$1\2 and cp-Gα$_i$3 peptides exert on left atrial ERPs through specific inhibition of MR$_2$\Gα$_i$ coupling.

Figure 21:
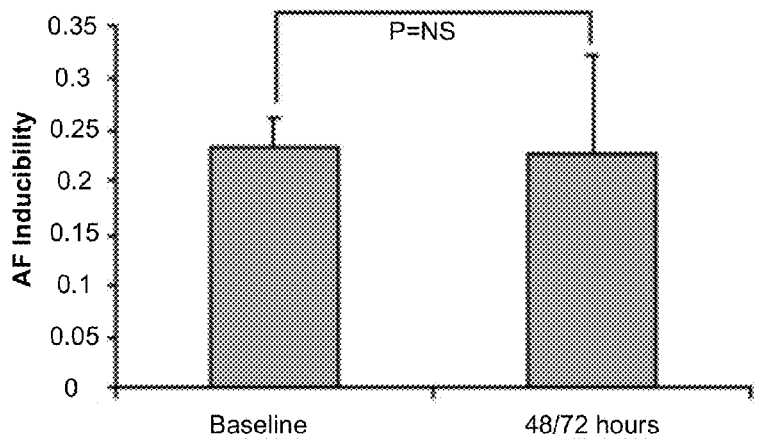
FIG. 21 shows a graph of vagal-induced AF inducibility upon GαR minigene injection.

Interjection of single extrastimuli rarely induced AF at BL (inducibility index=0.03), but frequently did so during VS-40 AF episodes >5 seconds in duration (inducibility index=0.17; i.e., more than five-fold that at BL) (SEE FIG. 21). However, after cp-Gα$_i$ peptide delivery into the PLA, AF inducibility in the presence of VS was significantly decreased—only 10 episodes >5 seconds in duration were induced (inducibility index=0.05, i.e., a 69% reduction in AF inducibility during VS). Sono\electroporation±cp-Gα$_o$R peptide in the PLA did not decrease AF inducibility during VS (SEE FIG. 21), indicating that any non-specific action of the peptides and/or sono/electroporation had no effect in this regard. In the control animals that received systemic beta-blockade, AF inducibility was also significantly decreased (as compared to vagal stimulation at baseline); the decrease in AF inducibility was comparable to that noted with cp-$G\alpha_I$ peptide (67% vs 69% respectively). These results demonstrate the feasibility of a topical, G-protein based approach achieving selective P denervation in the PLA, with a resulting change in vagal responsiveness in the entire left atrium (and a significant decrease in AF inducibility).

3.3.C. Demonstration of Intracellular Peptide Delivery after the Application of G$\alpha$i Peptide to the PLA.77

Left atrium tissue samples were taken from canine subjects after completion of the in vivo electrophysiology (section 3.3.B above) in which FLAG-tagged cp-$G\alpha_i1\backslash2$, cp-$G\alpha_i3$ or cp-$G\alpha_oR$ peptides had been delivered into their PLAs, and from a canine subject that had not been subjected the peptide experiments. Tissue homogenates of the PLAs and LAAs from each of these canine subjects was then evaluated for the presence of FLAG-tagged cp-$G\alpha_i1\backslash2$ peptide using anti-FLAG immunoassays. Anti-FLAG Western blot assay (SEE FIG. 22) indicated an intense band at ~20 kDa only for homogenates of PLA tissue samples taken at or near the site of peptide delivery in the in vivo electrophysiology experiments. PLA1, PLA2, PLA3 and PLA4 are different canine subjects that underwent cp-$G\alpha_i1\backslash2$ injection. No FLAG-tagged peptide was found in the LAA; LAA1, LAA2, LAA3 are 3 different canine subjects that underwent cp-$G\alpha_i1\backslash2$ injection. The incorporation of cp-$G\alpha_i$ peptide in the PLA was further confirmed by positive anti-FLAG immunostaining of epicardium-to-endocardium PLA cross-section tissue samples. Sections were taken from the PLA and LAA as described. Anti-FLAG immunostaining of epicardium-to-endocardium LAA cross-section tissue samples was negative. Positive anti-FLAG immunostaining was seen in autonomic nerve bundles in these PLA tissue sections, thus indicating that cp-$G\alpha_i$ peptides could incorporate and be retained by autonomic nerves innervating the PLA, indicating the cause of ERPs in the LAA and PV regions exhibiting changes after localized delivery of cp-$G\alpha_i$ peptide into the PLA. This remote effect can be explained by the uptake of peptide by the nerve bundles in the PLA. Autonomic nerve tracts to the LAA and PVs originate in, or at least pass through, the PLA, suggesting that the uptake of gene/peptide by the ganglion cell bodies near the site of delivery could therefore have electrophysiologic effects on nerve fibrils that are more 'distal' to the nerve trunks in the PLA.

3.4. Topical Denervation of the PLA with G$\alpha$i Peptide-Expressing Minigene

In canine subjects, high-density epicardial mapping was performed. After baseline mapping, 1 mg of either FLAG-tagged G$\alpha$i1/2 expressing minigene or FLAG-tagged G$\alpha$R (random peptide) expressing minigene (made up to a volume of 2 ml) was injected in the PLA. The PLA was then subjected to electroporation. Epicardial mapping was performed again at the 48 hour, 72 hour and 1 week time intervals after minigene injection. The animal was then euthanized and atrial tissue was frozen. RNA was isolated from frozen heart tissue for PCR and RT-PCR. Western blotting and immunohistochemical staining were performed for FLAG-tagged peptide.

Figure 26:
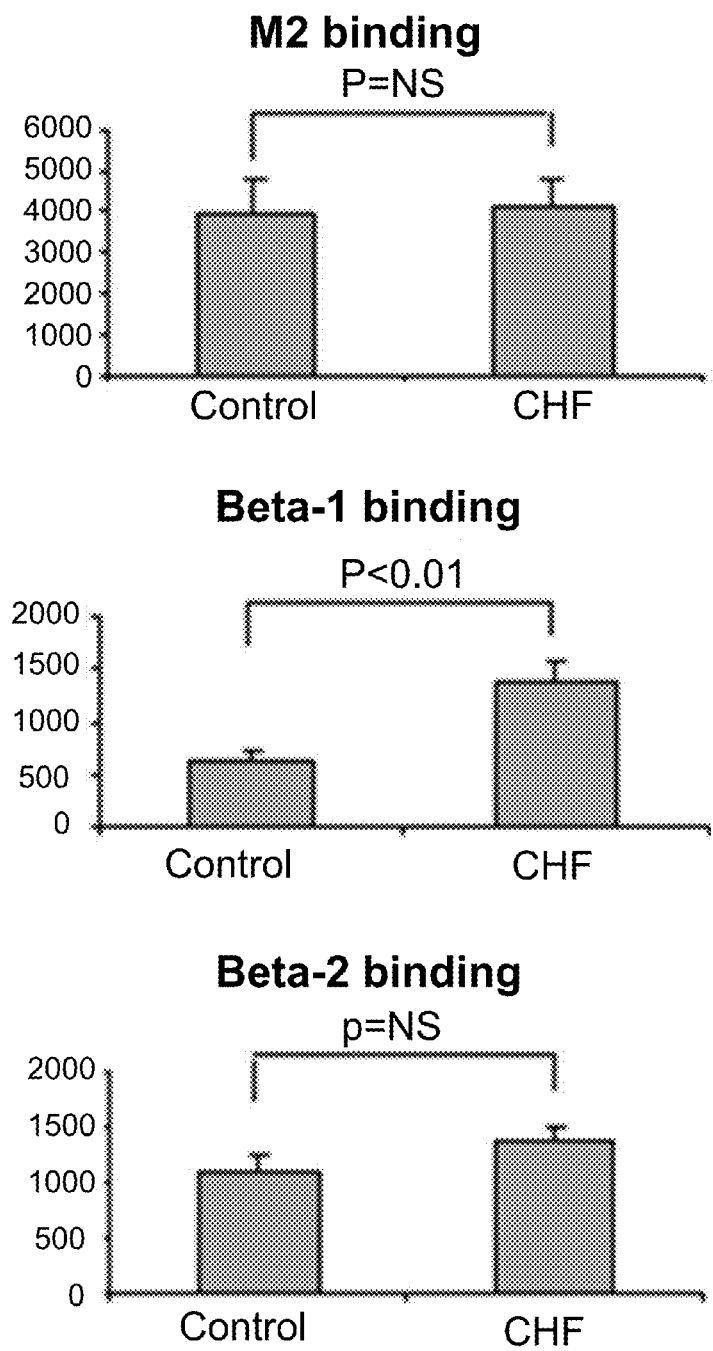
FIG. 26 shows a bar graph of β1, M2, β2 binding in CHF and control canine subjects.

G$\alpha$R minigene affects vagal induced ERP shortening (SEE FIG. 26). Significant VS-induced ERP shortening was noted at baseline in each canine subject. However, VS-induced ERP shortening was markedly attenuated after G$\alpha$i minigene injection (72 sec mean shortening at baseline vs 18 msec mean shortening after application of G$\alpha$i minigene, p<0.01).

Figure 27:
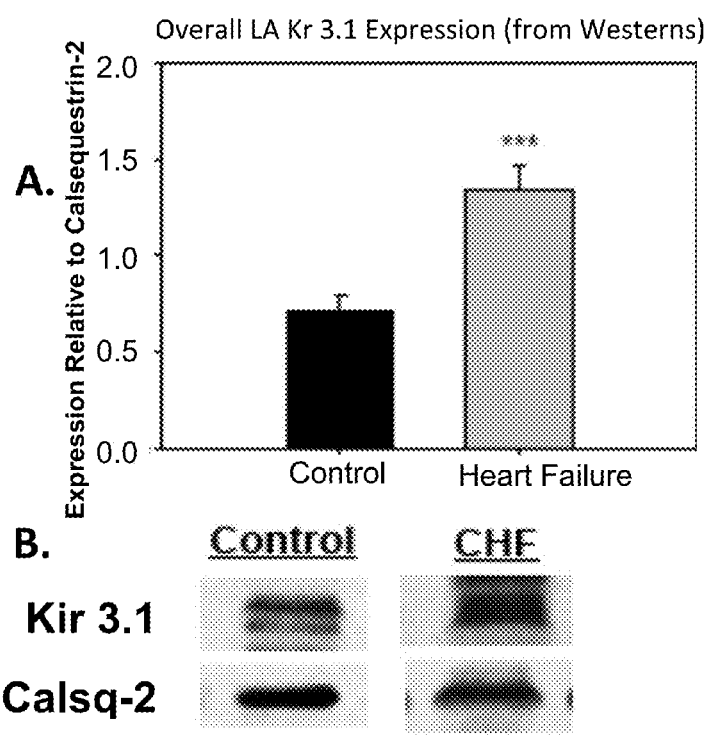
FIG. 27 shows (A) statistical analysis of Kir3.1 expression and (B) a representative western blot in the PLA of a CHF versus a normal canine subject.
Figure 28:
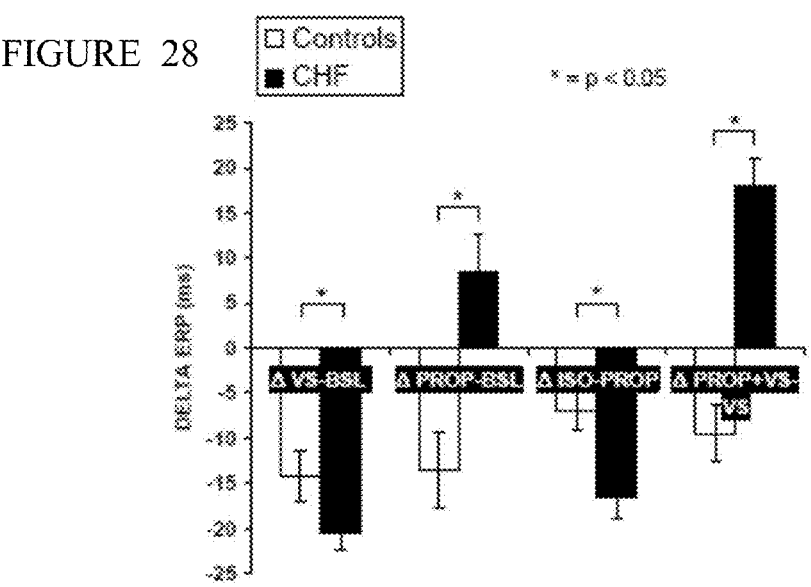
FIG. 28 show a comparison of electrophysiologic responsiveness in Group 1 (4 week pacing group) versus Group 3 (control group).
Figure 29:
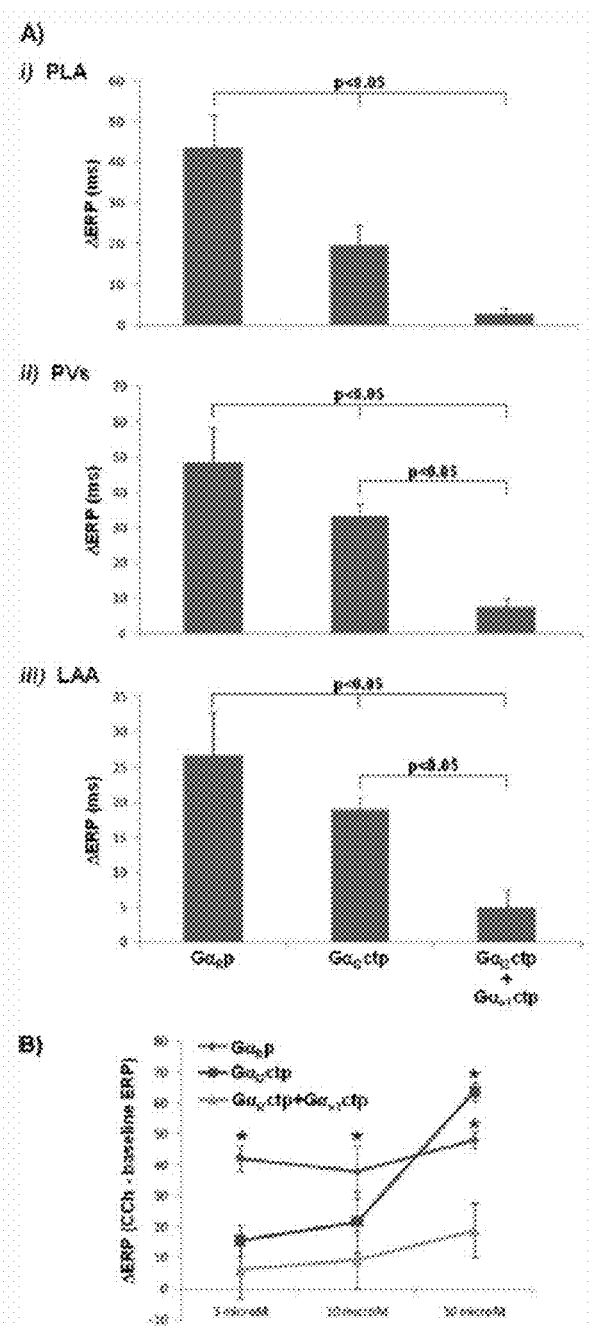
FIG. 29 shows attenuation by minigene-expressing Gαi/octp of VS- and CCh-induced ERP shortening. A. i) Compared to GαRcpt, vagal-induced ERP shortening in the PLA is attenuated in Gαi2ctp dogs and is nearly eliminated in Gαi2ctp+Gαo1ctp dogs. In Gαi2ctp+Gαo1ctp dogs, vagal-induced ERP shortening was also significantly attenuated in the ii) PV and iii) LAA. B. ERP shortening in the PLA in response to CCh. In GαRcpt dogs, significant ERP shortening was noted in response to each CCh concentration (3, 10 and 30 μM). In contrast, in Gαi2ctp dogs, ERP shortening was noted only at 30 μM CCh. In Gαi2ctp+Gαo1ctp dogs, there was no significant ERP shortening at any dose of CCh. * $p<0.05$ compared to baseline ERP at terminal study.
Figure 30:
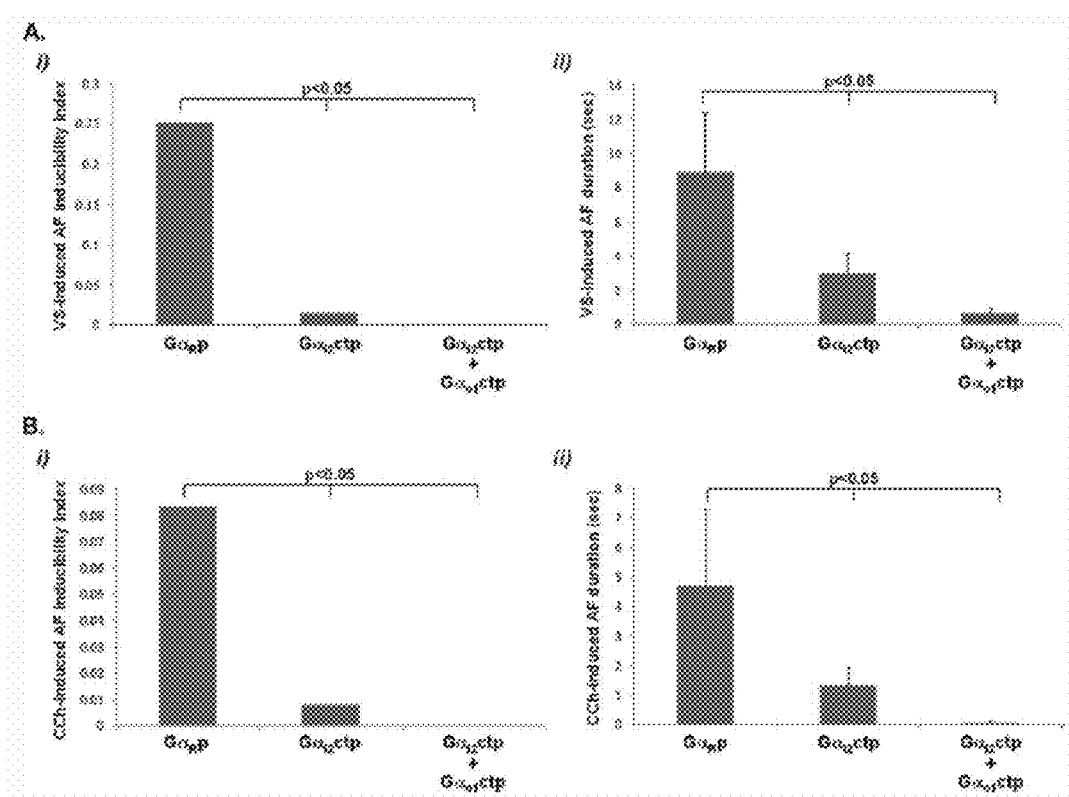
FIG. 30 shows a decrease in VS- and CCh-induced AF by minigene-expressing Gαi/o peptide. A. Decrease in VS-induced AF in Gαi2ctp and Gαi2ctp+Gαo1ctp dogs, as compared to GαRcpt. Both i) the AF inducibility index; and ii) mean AF duration showed a progressive decrease in Gαi2ctp and Gαi2ctp+Gαo1ctp dogs respectively. B. Decrease in CCh-induced AF in Gαi2ctp dogs and in Gαi2ctp+Gαo1ctp dogs, as compared to minigene-expressing GαRcpt. Both i) the AF inducibility index; and ii) mean AF duration showed a progressive decrease in Gαi2ctp and Gαi2ctp+Gαo 1 ctp dogs respectively.

VS-induced ERP shortening was maximally affected in the PLA (the site of injection), but was also affected at sites remote from the PPVs and LAA (SEE FIG. 27). Vagal-induced AF inducibility was significantly diminished after G$\alpha$1/2 minigene injection (SEE FIG. 29). Although some attenuation of VS-induced ERP shortening occurred in control canine subjects receiving G$\alpha$R minigene, the effect was significantly less than in canine subjects receiving G$\alpha$1/2 minigene (SEE FIG. 28). VS-induced AF inducibility was not significantly affected in canine subjects receiving G$\alpha$R minigene (SEE FIG. 30). The lack of effect at one week is consistent with the absence of significant gene expression at this time point (SEE FIG. 18). These results demonstrate the feasibility of a topical, minigene-based approach in achieving G$\alpha$i inhibition in the PLA, with a resulting change in vagal responsiveness in the entire left atrium.

Figure 22:
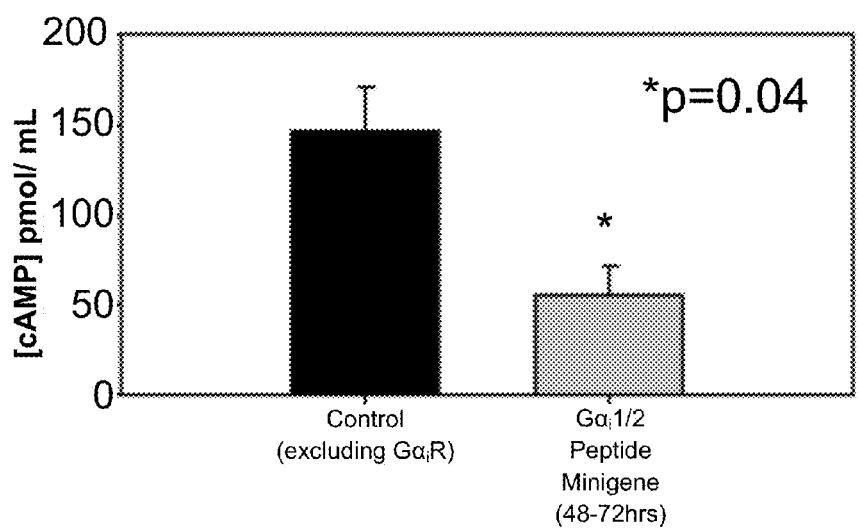
FIG. 22 shows a graph of the effect of minigene injection on cAMP levels.
Figure 23:
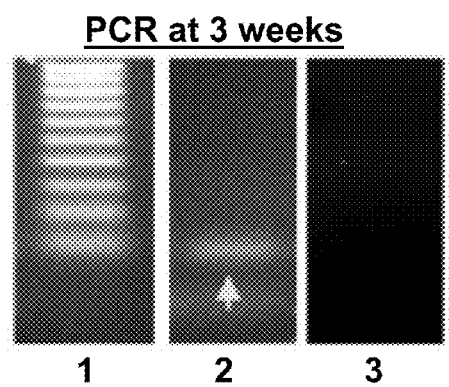
FIG. 23 shows the results of PCR for LacZ mRNA expression; lane 1 is a 50 bp ladder, lane 2 indicates band of interest). In contrast, lane 3 is control animal.
Figure 24:
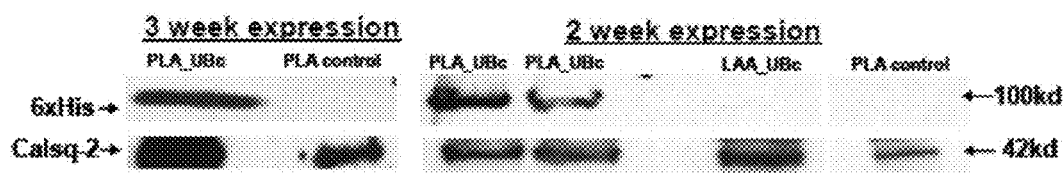
FIG. 24 shows Western blotting at 2 and 3 weeks demonstrating expression of the 6×His epitope in the PLA of animals that had undergone gene injection.
Figure 25:
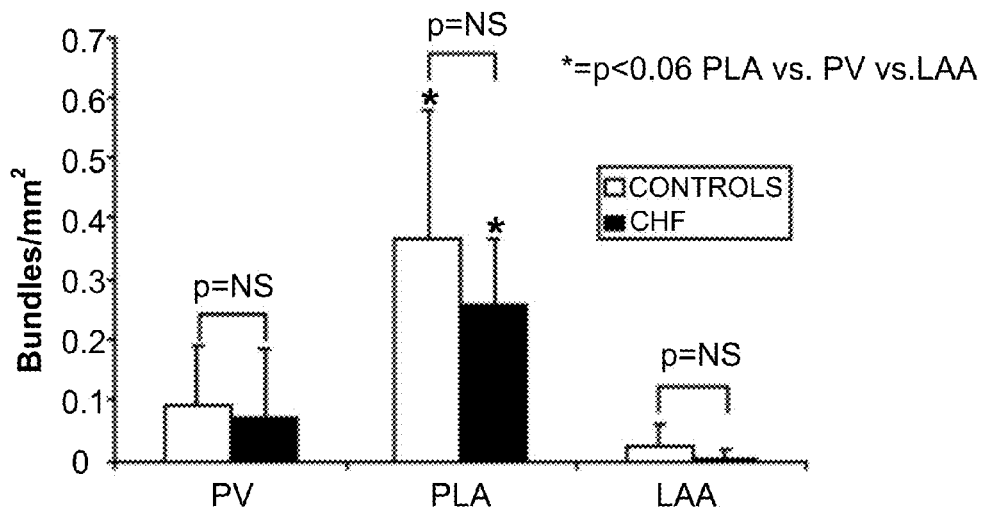
FIG. 25 shows bar graphs representing the results of nerve studies of the left atrium.
Figure 25:
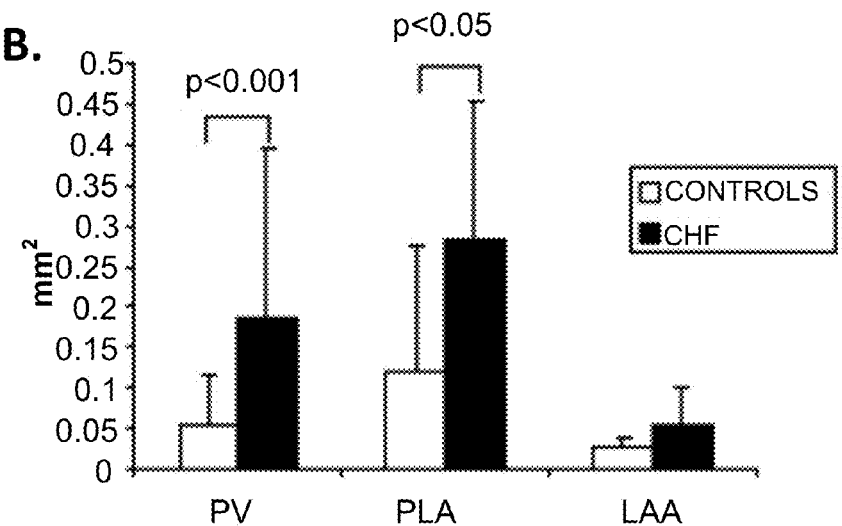
Figure 25:
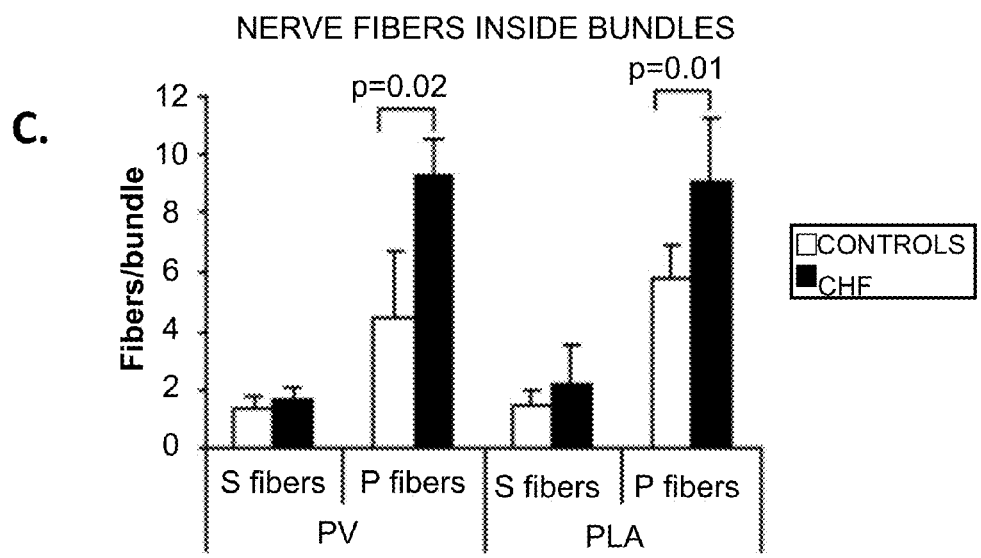
Figure 25:
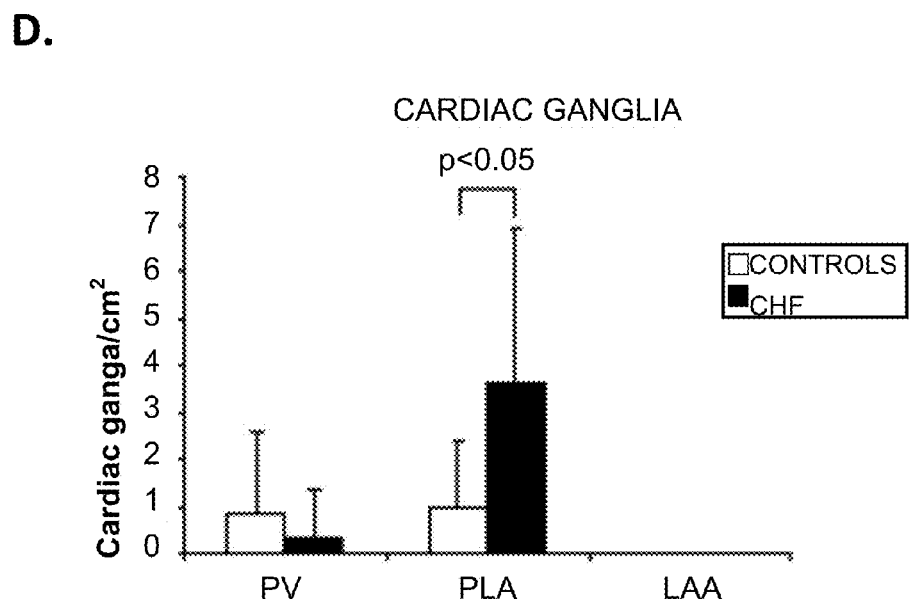

The effects of the minigene on G-proteinactivity were assessed by measuring cAMP levels. cAMP activity was decreased in canine subjects receiving G$\alpha$i1/2 minigene, compared to normal controls (SEE FIG. 22). Acute inhibition of G$\alpha$i results in an increase in cAMP levels. The decrease in cAMP levels 48-72 hours after injection indicates the presence of compensatory responses to sustained G$\alpha$i inhibition.

Figure 32:
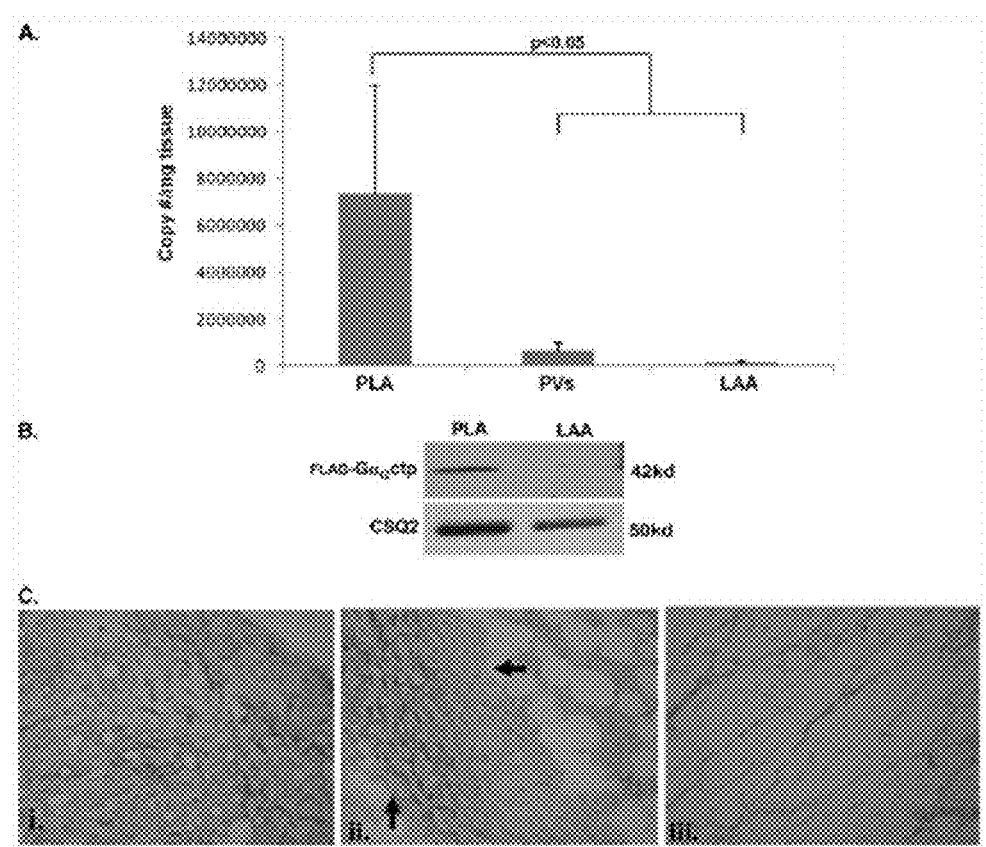
FIG. 32. Verification of $Gα_x$ peptide transgene expression in the left atrium. A. Results of PCR on PLA, PV and LAA tissue. Transgene expression (for both Gαi2ctp and GαRcpt minigenes) was noted in the PLA. There was minimal expression in the adjoining PV, and no expression in the LAA. B. Results of western blotting for FLAG-tagged Gαi2ctp. FLAG-tagged peptide was detected in the PLA, but not in the LAA. Calciquestrin Q is the loading control for each lane. C. An example of immunohistochemistry for FLAG-tagged Gαi2ctp. FLAG-tagged peptide (heavy brown stain) was detected in i) the PLA myocytes; and in ii) nerve bundles in the PLA; but not in iii) the LAA.

3.5. Lone Term Gene Expression in the Posterior Left Atrium Objective:

In canine subjects, 1 mg of pUB6/V5/-His/LacZ plasmid (Invitrogen) (containing V5 and 6xHis epitope tags) in which expression of the lacZ reporter gene is driven by a UbC promoter was delivered into the PLA. The chest was then closed and the animal monitored for 2-3 weeks. At the end of this time interval, a terminal study was performed and the heart removed for further analysis. The PLA were subjected to PCR for the presence of LacZ mRNA (transcribed gene product). Western blotting was performed for the 6xHis epitope (translated gene product). PCR and Western blotting were also performed on the PLA of two control canine subjects (i.e. not subjected to gene injection). At 3 weeks, LacZ was expressed in the PLA of the canine subjects that underwent gene injection (SEE FIG. 32). The 6xHis epitope was expressed in the PLA of animals that had undergone gene injection, but not in control animals (SEE FIG. 33). At both two and three weeks, 6xHis expression is seen in the PLA. In contrast, no 6xHis expression is noted in the LAA, which is remote from the site of injection, nor in the PLA from control canine subjects that had not undergone gene injection. Calciquestrin 2 was used as the loading control for each sample. These results demonstrate that long term gene expression can be obtained in left atrium with a plasmid under the control of a UBc promoter.

3.6. Autonomic remodeling in a canine model of atrial fibrillation10, 11

3.6.A. Molecular Studies:

Rapid RV pacing was performed for 3 weeks in canine subjects. Progressive atrial and ventricular dilatation was noted on weekly echocardiograpy. At the end of this period, animals were euthanized and the PVs and left atrium removed and frozen for further analysis. Tissue from the PLA, PVs and LAA was subjected to immunostaining and western blotting to assess for nerve growth and expression of G$\alpha$i2/3, G$\alpha$ and IKAch. cAMP activity was also assessed in each region. Control tissue was obtained from the same regions from normal control animals.

Immunohistochemistry for Parasympathetic and Sympathetic Nerves.

PVs were harvested from canine subjects with CHF and normal controls. The PVs were taken as the region extending from the antrum to the junction of the left atrial myocardium/

PV smooth muscle. The adjoining PLA (defined as the confluence of the PVs) and the anterior LA (LAA) were also harvested. Regions containing fat were incorporated in the tissue sections taken from the PLA. Control specimens were taken from the cervical vagus nerve and stellate ganglia. The tissue was frozen in liquid nitrogen. Serial circumferential cross-sections (5μ each) were cut (proximal-to-distal) from the PVs. Sections from the posterior and anterior LA, including LAA, were cut parallel to the plane of the mitral annulus so as to include the epicardial and endocardial aspect of the myocardium in each slice.

Sectioning of Tissue from the SVC and RAA

In canine subjects with CHF and control canine subjects, the superior vena cava (SVC) and right atrial appendage (RAA) were harvested. Circumferential SVC sections were taken from myocardium at the junction of the SVC and RA (within 5 mm of the SVC/RA junction). The RAA was section in a manner similar to the LAA.

Nerve Count Estimation

Nerve bundles and individual nerve fibrils were manually counted at 10× magnification for the entire section. Nerve bundles or trunks were defined as large collections of individual nerve fibers/fibrils with a diameter ≧0.025 cm. Nerve fibrils were defined as thin nerve fibers with diameters of <20 μm. (24). Mean densities of nerve fiber bundles, mean densities of nerve bundles containing neuronal cell bodies (cardiac ganglia), and mean sizes of the nerve bundles were quantified under magnification. The means of each region were compared between the two groups. In addition, the number of cholinergic and adrenergic fibers was counted manually within several, randomly selected nerve bundles that demonstrated co-localization of P and S fibers; at least 5 bundles were selected from each region. To account for variation in nerve/nerve bundle size, the ratio of cholinergic to adrenergic nerve fibers (averaged for the randomly selected bundles from each region) was taken as an estimate of the relative distribution of cholinergic vs adrenergic nerve fibers in each region. Quantification was separately performed for the epicardial versus the endocardial half of the section.

β1, β2, M2 Receptor Binding Assays

Receptor binding assays were performed for β1, β2 and M2 receptors.

Western Blotting for Gαi2/3, Gαs, Kir3.1

Western blotting was performed to assess for expression of the G-proteins and IKAch (Kir3.1 subunit).

Figure 34:
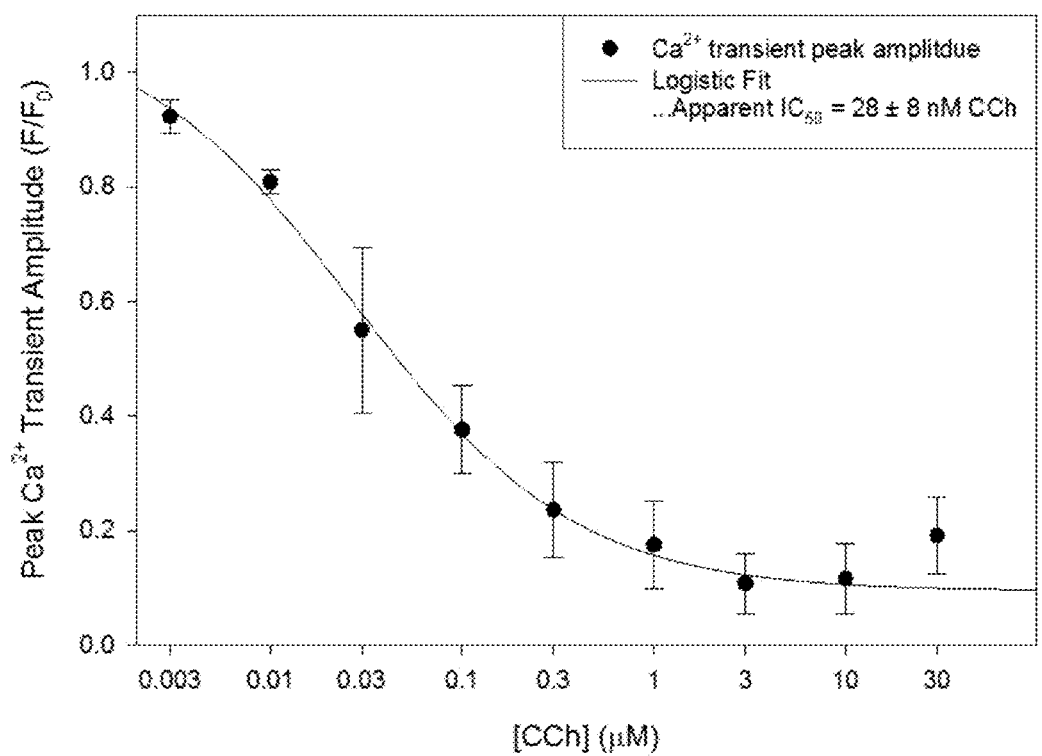
FIG. 34 shows Ca2+ transient Peak Amplitude attenuation vs. CCh concentration in isolated canine atrial myocytes. With increasing concentrations of CCh, there was a progressive attenuation of Ca2+ transient Peak Amplitude in isolated atrial myocytes. Maximal attenuation was obtained at around 3 μM CCh, with further increases in concentration resulting in no additional attenuation.
Figure 35:
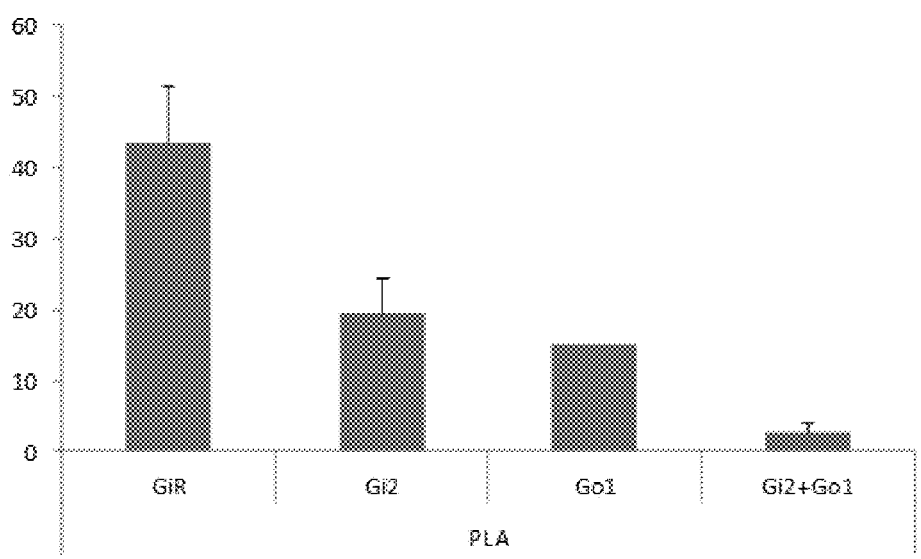
FIG. 35 shows the results from Example 5 where a Gαo1 inhibitor was used to treat induced arrhythmias is a dog.

Nerve bundles predominated in the PLA in both groups (SEE FIG. 34). Nerve bundle size was significantly increased in the CHF group both in the PV and the PLA (SEE FIG. 34). Nerve bundle size was significantly greater in CHF atria versus control. In the CHF group, there was a statistically significant increase in the number of parasympathetic fibers inside the bundles (SEE FIG. 34). Accordingly, the total number of fibers increased both in the PV and the PLA. Cardiac ganglia containing neuronal cell bodies were found only in the PLA and the PV, not in the LAA. Cardiac ganglia were ACE positive (parasympathetic). PLA section from a CHF canine subject; Large ganglion bundles consisting of neuronal cell bodies occurs in a PLA section from a CHF canine subject. A nerve bundle consisting of nerve fibers arose from the ganglion cell bundle on the left. In the CHF group, there was a significant increase in the number of cardiac ganglia in the PLA (SEE FIG. 34). The number of neuronal cell bodies within the cardiac ganglia was significantly increased in the CHF group as compared to the control group. CHF produces neural remodeling in the left atrium, resulting in a marked increase in nerve bundle size, as well as the number of parasympathetic ganglion cells and nerve fibers inside the nerve bundles in the posterior left atrium. Unlike in the left atrium, there was no significant increase in nerve distribution in the SVC and RAA in the setting of CHF. Nerve bundles were found in the SVC, but not in the RAA. There was no significant difference in the density of nerve bundles between normal and CHF canine subjects. In contrast to the left atrium, nerve bundle size was decreased in the setting of CHF (0.74±0.28 mm$^2$ vs 0.40±0.07 mm$^2$). The number of nerve fibers within nerve bundles was similar between normal and CHF (6.6±3.4 vs 5.9±1.9 respectively). In CHF canine subjects, β1 binding was significantly increased in the left atrium (SEE FIG. 35). There was no significant change in left atrial M2 binding and β2 binding in CHF (SEE FIGS. 35). cAMP activity, an index of G-protein activity, was increased in the setting of CHF. In CHF canine subjects, cAMP activity was greatest in the PLA; however, there was no statistically significant increase in expression Gαs or Gαi2/3. Since P effects on atrial refractoriness are primarily driven by IKAch, expression of the IKAch subunit Kir3.1 was assessed in the atria. Kir3.1 expression paralleled the increase in P nerves, being more pronounced in the left atrium in the setting of CHF (SEE FIG. 27).

3.6.B. Functional Studies:

Canine subjects were divided into three groups. In group 1, CHF was induced by rapid ventricular pacing for 4 weeks (i.e. when the animals began to develop clinical heart failure. In group 2, pacing was performed for only 3 weeks. Group three were control canine subjects not subjected to rapid ventricular pacing. At the end of follow up period, high-density epicardial mapping was performed in the PVs, the PLA and the LAA. ERPs were obtained at multiple sites under the following conditions: a) baseline (BSL), b) left cervical vagal stimulation at 20 Hz (VS), c) beta-stimulation with isoproterenol (ISO), d) beta-blockade with propranolol (PROP) and e) beta-blockade+vagal stimulation (P+VS). VS caused significant mean ERP shortening in all three groups. The absolute shortening (delta between BSL and VS) was significantly greater in Group 1 than in the other two groups. PROP caused significant shortening of ERPs in control canine subjects, while it caused the opposite (ERP lengthening) in CHF canine subjects. ISO significantly shortened the mean ERP in both groups compared to PROP, but the magnitude of this difference was higher in the CHF group. PROP increased the VS effect on ERP in normal controls, but produced an attenuation of this effect in the CHF group (SEE FIG. 37). In this CHF model, after 4 weeks of pacing, an increased vagal effect on atrial refractoriness, an increased cumulative sympathetic effect, and a change in the sympatho-vagal interactions of the left atrium were observed. After 3 weeks of pacing, there is pronounced autonomic remodeling, with evidence of P as well S nerve upregulation in the PVs and left atrium. Both P and S upregulation are more pronounced in the PLA (and to a lesser extent in the PVs) than in the rest of the left atrium. While vagal responsiveness in the left atrium is unaltered at 3 weeks of pacing, it increases after 4 weeks of pacing. Sympathetic responsiveness is also increased after 4 weeks of pacing. The data indicate that pacing-induced CHF results in evidence of sympathetic as well as parasympathetic remodeling in the left atrium. The autonomic remodeling becomes more pronounced with increasing duration of pacing. While an overall upregulation of sympathetic and parasympathetic signaling molecules was observed, not all the key signaling molecules in the autonomic cascade were significantly altered. The increase in β1 binding is consistent with the increase in sympathetic innervation. The results indicate an increase in sympathetic as well as parasympathetic activation in the setting of CHF. The P upregulation noted in the left atrium in CHF is a compensatory response to S upregulation that occurs in response to CHF. Recent studies in the ventricle have in fact demonstrated an increase in Gαi in CHF, also thought to be a compensatory response to worsening CHF. However, since normal atria are more densely innervated with vagal fibers (than the ventricle) and also contain a significant amount of IKAch, the compensatory response is likely to be more vigorous in the atrium. The compensatory increase in vagal innervations, and resulting increase in IKAch, may contribute to increased AF substrate.

The robust autonomic profile of the PLA in normal hearts plays a role in AF, thereby making it an attractive target for autonomic manipulation by regional delivery of Gα C-terminal peptides. C-terminal peptides from Gα can be used to selectively block G-protein signaling that is specific to autonomic pathways. Topical application of cp-Gαi peptide to the PLA can successfully modify substrate for vagal AF. Topical injection of Gαi minigene in the PLA results in Gαi peptide production, with successful modification of vagal AF substrate. Long-term gene expression in the PLA with a plasmid/minigene approach is feasible. Pronounced autonomic remodeling is noted in the setting of heart failure-induced AF, with evidence of significant S as well as P nerve growth. This nerve growth is preferentially localized to the PLA and is accompanied by a significant increase in expression of the signaling molecules that mediate S and P effects in the atria. The preferential nerve growth seen in the PLA makes it a suitable target for S and/or P denervation using regionally-directed G-protein inhibition.

Example 4

Arrhythmia Treatment with Gαi and Gαo Inhibitors

This Example describes in vivo treatment of arrhythmias with a Gαi inhibitor and the combination of a Gαi and Gαo inhibitor. In particular, in 8 dogs, plasmid DNA vectors (minigenes) expressing Gα$_i$ C-terminal peptide (Gα$_i$ctp) was injected in the posterior left atrium (PLA) either alone or in combination with minigene expressing Gα$_o$ctp, followed by electroporation. In 5 control dogs, minigene expressing scrambled peptide (Gα$_R$ctp) was injected. Vagal and carbahol (CCh) induced left atrial effective refractory periods (ERPs), AF inducibility and Gα$_{i/o}$ctp expression were assessed 3 days following minigene delivery. Vagal stimulation- and CCh-induced ERP shortening and AF inducibility were significantly attenuated in atria receiving a Gα$_{i2}$ctp-expressing minigene, and were nearly eliminated in atria receiving both Gα$_{i2}$ctp- and Gα$_{o1}$ctp-expressing minigenes.

Methods

Minigene Preparation

Cloning of Gα$_{i2}$ctp, Gα$_{o1}$ctp and Gα$_R$ctp inserts into plasmid backbone The corresponding cDNA sequence of the last C-terminal 11 amino acids of the Gα$_{i2}$ subunit (IKNNLKDCGLF; SEQ ID NO:7), and that for the Gα$_{o1}$ subunit (IANNLRGCGLY; SEQ ID NO:8) and that of random-ordered Gα$_{i2}$ctp (Gα$_R$p), were each separately cloned into a pFLAG CMV6a plasmid expression vector (Sigma-Aldrich) to generate Gα$_{i2}$ctp- Gα$_{o1}$ctp- and Gα$_R$p-expressing plasmid constructs (minigenes).

Transformation and Plasmid Purification

Plasmids were propagated in *Escherichia coli* and purified using Qiagen Mega-prep kits, as described by the manufacturer (Qiagen, Valencia, Calif.). Details of transformation and plasmid purification are given further below.

Gene Injection and In Vivo Electrophysiological Testing

Gene injection and electroporation: A total of 19 dogs (hounds) were used for this Example (12 male, 7 female). Animals were premedicated with acepromazine (0.01-0.02 mg/kg) and were induced with propofol (3-7 mg/kg). A median or lateral sternotomy was then performed under general anesthesia (inhaled) with isoflurane (1-3%). Adequacy of anesthesia was assessed by toe pinch and palpebral reflex.

In a small number of pilot experiments (N=6), 1 mg of Gα$_{i2}$ctp or Gα$_R$p minigene was injected subepicardially in the PLA (also see Results). In the remaining experiments, 15-20 mg of ct-Gα$_{i2}$ctp (N=5), or 7-10 mg of Gα$_{i2}$ctp+7-10 mg of Gα$_{o1}$ctp (N=3), or Gα$_R$p (N=5) minigenes was injected in the PLA. Minigenes were made up to a volume of 4 ml and injected at multiple sites (6-8 equally spaced sites, 0.5-1 cm apart; a volume of approximately 0.5 ml was injected at each site) in the PLA so as to cover the entire area between the PVs. The injected region is anatomically clearly demarcated (the four borders used are: base of the left atrial appendage, base of the left inferior PV, interatrial septum, and atrioventricular groove) and is the one that is removed after gene injection. Immediately after gene injection, electroporation was performed at each site of injection as follows: two gold-plated, needle-style electrodes (10 mm length each) were placed at each gene injection site on the PLA, with an inter-electrode distance of 5 mm; electroporation with performed as previously described in the lung by Dean et al[14], with 8 pulses of is at 120-150V/cm$^2$ (ECM 830, Harvard Bioscience, Holliston, Mass.). After minigene delivery, the chest was closed and the animal allowed to recover. Vagal stimulation and electrophysiological testing were not performed at baseline, in order to minimize damage to the vagus nerve.

Terminal Electrophysiological Study:

Baseline study: Three days after the initial study, the chest was re-opened. High density plaques were applied to the left superior PV (8×5 electrodes; 2.5 mm spacing), PLA (7×3 electrodes, 5 mm spacing) and LAA (7×3 electrodes, 5 mm spacing). The PV plaque was placed circumferentially around the vein while the other two plaques were laid flat on the PLA and LAA epicardium. Effective refractory periods (ERPs) were obtained from 5, 6, and 4 sites on the PV, PLA, and LAA plaque, respectively, at baseline.

Vagal stimulation: For vagal stimulation, the left cervical vagus nerve was isolated, a bipolar stainless steel electrode was attached to the nerve, and stimulation was performed at 20 Hz (15-20V, 2-8 ms) (Grass S44G, Astromed Inc, R1). A vagal response was defined as: 1) sinus node slowing by at least 25% or 2) PR prolongation by more than 25% or 2:1 AV block[13]. ERP testing was performed in the presence and absence of VS.

CCh application: ERP shortening was assessed by direct application of CCh, a non-selective MR agonist, to the PLA. CCh was injected under the subepicardium of the PLA in increasing doses—i.e.: 3, 10 and 30 µM (also see in-vitro CCh dose finding studies below). After each dose, ERP testing was performed in the PLA. Long periods of AF were frequently encountered during atrial pacing at higher concentrations of CCh, and thus precluded ERP testing at these higher doses.

Atrial Fibrillation Inducibility: AF was defined as an atrial arrhythmia that was irregular in at least one of the recording electrodes. Regular atrial arrhythmias—e.g., atrial flutter and atrial tachycardia—were excluded from AF analysis. AF inducibility was measured as the inducibility index and duration of AF episodes after a single extrastimulus[8,15]. As previously described, the inducibility index was defined as the number of AF episodes lasting more than 5 seconds induced by a single atrial extrastimulus divided by the total number of single atrial extrastimuli delivered to measure each ERP (at least 3 for each site)[8]. The inducibility index was compared for each maneuver. Mean AF duration for each intervention was also assessed. All data was acquired by a 128-channel mapping system (Prucka Cardiolab, GE, WI) at a sampling rate of 977 Hz. All AF episodes induced during extrastimulus testing were stored for offline analysis. After all ERPs had been obtained, minigene injection was performed as described below.

Offline Electrogram Analysis. Electrograms recorded during the maximum duration AF episodes obtained during extrastimulus testing were analyzed with dominant frequency (DF) analysis. DF is an estimation of activation rate calculated as the frequency with the most power in the power spectrum. The power spectrum is obtained from the Fast Fourier Transform of an electrogram after rectification and low pass filtering (20 Hz). These analyses were performed offline using Matlab (Mathworks, Natick, Mass.).

Tissue Explant Assays

Upon finishing the in vivo portion of the study, euthanasia was achieved by a high dose of pentobarbital (>20 cc, fully saturated) to achieve a very deep plane of anesthesia and the heart removed and perfused with cold cardioplegia solution. The left atrium and PVs were dissected, snap frozen and subjected to further analysis as detailed as follows.

Transgene Expression mRNA expression: The following primers to detect minigene-expressed mRNA were obtained from IDT (San Diego, Calif.)

$G\alpha_{i2}$ctp:
(SEQ ID NO: 1)
Forward-AGCTCAAGCTTATCAAGAACAACCT, (SEQ ID NO: 2)
Reverse-TACCGGATCCTCAGAAGAGGC $G\alpha_{o1}$tp:
(SEQ ID NO: 3)
Forward-AGCTCAAGCTTATTGCCAACAACC (SEQ ID NO: 4)
Reverse-GGTACCGGATCCTCAGTACAAGCC $G\alpha_R$p:
(SEQ ID NO: 5)
Forward-CAAGCTTAACGGCATCAAGTGC, (SEQ ID NO: 6)
Reverse-GGTACCGGATCCTCACAGCTT Quantitative real-time PCR (qRT-PCR) was performed to assess for expression of $G\alpha_{i2}$ctp, $G\alpha_{o1}$ctp and $G\alpha_R$p expressing minigenes in the PLA following gene injection. GAPDH was used as a reference for sample-normalization.

Western blotting: Anti-FLAG antibodies (Sigma) were used to assess for the presence of FLAG-tagged $G\alpha_{i2}$ctp in PLA tissue. Calsequestrin-2 was used as a loading control.

Immunohistochemistry: Thin sections (5 μm) of the PLA were obtained for H&E staining and for immunohistochemistry (the latter to assess for FLAG-tagged $G\alpha_{i2}$ctp).

CCh Concentration-$Ca^{2+}$ Transient Response Assay in Isolated Canine Atrial Myocytes Myocyte isolation: Canine right atrial myocytes (from same hearts excised as described above) were isolated by collagenase digestion via coronary perfusion modified procedure previously described[8,16]. Dissociated myocytes were stored in normal Tyrode's solution at 4° C. until use in confocal $Ca^{2+}$ transient experiments as described.

$Ca^{2+}$ transients acquisition and CCh administration: As previously described[8], isolated atrial myocytes were incubated with 5-10 μM of the $Ca^{2+}$-fluorescence dye, fluo-4 (Invitrogen). AP-evoked $Ca^{2+}$ transients were acquired as confocal X-t line-scan images of uncalibrated fluo-4 fluorescence at a scan rate of 1.92 ms/line-scan. Laser phototoxicity was minimized by scanning at <10% output transmission. Changes in $Ca^{2+}$ transients in response to serial concentrations of acutely applied CCh (0.01-30 μM) were measured from multiple myocytes per isolation preparation.

Statistical Methods

All data is reported as mean±SE. Comparisons between $G\alpha_{i2}$, $G\alpha_{i2}$+$G\alpha_{o1}$ and $G\alpha_R$ dogs (for ERP, AF inducibility) were assessed for significant differences via ANOVA. Dominant Frequency comparisons between $G\alpha_{i2}$ and $G\alpha_R$ dogs were made using unpaired t-tests. Before and after comparisons made in same animals (e.g., before and after VS or CCh) were assessed for significant differences via paired t-tests. A p value of ≦0.05 was taken as significant.

In Vivo Electrophysiological Mapping

Effective Refractory Periods. For each ERP, the pacing protocol was composed of a drive train (S1) of eight beats with a cycle length of 400 ms followed by an extrastimulus (S2). The S2 was decremented by 10 ms until loss of capture. The longest S2 which did not capture was considered the ERP for that particular site. Pacing was performed at an output current twice the threshold required for consistent capture of the tissue. The mean ERP was used as the representative ERP for each of the three sites as well as the entire left atrium.

Minigene Preparation

Cloning of $G\alpha i2$ and $G\alpha R$ inserts into plasmid backbone: DNA was prepared. Appropriate restriction enzymes were selected. The following were combined in a microfuge tube (30 μL total volume): 2 μg DNA, 1 μL Each Restriction Enzyme, 3 μL 10× Buffer, 3 μL 10×BSA, $H_2O$ (to bring total volume to 30 μL). The tubes were incubated at 37° C. for 1 hour. DNA was purified using Qiagen kit. For ligation, the following were mixed in a microfuge tube (10 μL total volume): 1 μL Vector DNA, 3 μL Insert DNA, 1 μL 10× Ligase Buffer, 1 μL T4 DNA Ligase, 4 μL $H_2O$ (to bring total volume to 10 μL) and incubated at 16° C. overnight.

Transformation and Plasmid purification: A basic heat shock method was used for transformation. 5 ng of stock $G\alpha i2$ plasmid was added to XL10 gold (E. coli competent cells) and placed on ice for 30 minutes. They were then heat shocked at 42° C. for exactly 30 seconds (to allow the uptake of the plasmid) and returned to ice. The cells were then grown in a shaking incubator for 1 hr in sterile LB broth containing 100 ug/ml ampicillin and plated for overnight incubation at 37° C. and 5% CO2. The next day, a colony was selected and grown in 3 ml of the same sterile LB Broth growth media with ampicillin and grown overnight in a 37° C. shaking incubator. One milliliter was used to make a 1:1 solution of glycerol for a bacteria stock. The other two milliliters were used according to manufacturer's instructions with the Sigma GenElute Plasmid Miniprep kit (catalog #PLN-70) and then sent to sequencing.

The plasmid was then purified using manufacturers instructions associated with the Qiagen Plasmid Mega Kit (catalog #12183). A small scraping of the bacterial stock was added to 1 L autoclaved LB broth growth media supplemented with 100 ug/ml of ampicillin and grown overnight. The next day, the bacteria were pelleted in an ultracentrifuge to remove the media. The bacteria were then lysed and centrifuged again to separate the plasmid in the supernatant. For purification, the supernatant containing plasmid was added to the Qiagen Mega Prep Column and subsequently washed and eluted. Two final spin steps were performed with isopropanol to precipitate the plasmid and ethanol to wash the plasmid. The pellet was air dried and then resuspended in TE buffer, pH 8.0.

PCR

Homogenization/RNA isolation: Tissue was processed according to manufacturer's instructions for the RNeasy Fibrous Tissue Mini Kit (Qiagen, #74704). Briefly, frozen tissue was crushed with a mortar and pestle and immediately put in the lysis buffer RLT from the RNeasy kit. The tissue was then homogenized with a rotor-stator homogenizer, treated with proteinase K, and centrifuged to remove debris. The supernatant was mixed with ethanol and centrifuged through silica membrane spin-columns that bind total RNA. Trace DNA (i.e., residual $G\alpha_x$ctp-expressing plasmid) that may copurify with the total RNA is removed by DNAase treatment (15 min of 27 Kunitz DNaseI). DNase and any contaminants are then washed off the spin-columns. The spin column-bound RNA is then elusted with RNase-free water.

Reverse Transcription: Reverse transcription was performed according to manufacturers instructions associated with Quanta Biosciences qScript cDNA SuperMix (#95048-100). In a 0.2 ml tube, 1 ug of RNA from each sample was added to the supermix and put in a thermocycler for the Quanta recommended 40 minute program to make cDNA.

Real-time PCR: The 20 ul cDNA reverse transcription product was diluted 1:5. In each well of a 96 well reaction plate, 4 ul of diluted cDNA was added to 6 ul of a mixture containing Applied Biosystems Fast SYBR Green Master Mix (#4385612) and 0.5 uM primers. After running the plate on the Applied Biosystems 7500 Fast System, results were analyzed by 7000 System SDS Software and quantified using the delta-delta CT method.

Western Blotting

Tissue samples of PLA, PV and LAA obtained from each dog were flash frozen in liquid nitrogen. Subsequently, samples were crushed, then homogenized and solubilized in Laemmli sample buffer and subjected to SDS-PAGE using 4-20% acrylamide gradient gels in a Tris-glycine system (Bio-Rad). Electrophoresed proteins were then transferred to nitrocellulose membranes for immunoblot analysis. Nonspecific protein-binding sites were blocked with PBS containing 5% milk. Membranes were incubated with anti-FLAG antibody (SIGMA), and anti-calsequestrin-2 (CALSQ2) polyclonal antibodies (Santa Cruz Bio) at 1:500-1:1000 dilution. Peroxidase-conjugated secondary antibodies (Pierce), at 1:5000-1:10000 dilution, were used to detect bound primary antibody. Protein bands were visualized via enhanced chemiluminescence (Amersham). Optical density of protein/peptide bands were quantified using ImageJ. Relative $G\alpha_i$ protein expression was normalized to that of CALSQ2.

Atrial Myocyte Isolation

Canine atrial myocytes were isolated from these hearts via a modified procedure previously described[6]. Briefly, after completion of limited in vivo electrophysiology experiments and while dogs were still deeply anesthetized, their hearts were quickly removed and immersed in cold cardioplegia solution containing (mM) NaCl 128, KCl 15, HEPES 10, $MgSO_4$ 1.2, $NaH_2PO_4$ 0.6, $CaCl2$ 1, glucose 10, and heparin (0.001 U/mL); pH 7.4. All solutions were equilibrated with 100% $O_2$. The aorta was cannulated, and the heart was perfused with cold cardioplegia solution until effluent was clear of blood and heart was cold (5-10 min). The ventricles were cut away, the left circumflex coronary artery and/or right coronary artery was cannulated, and the LA or RA was dissected free. The atrium was slowly perfused with cold cardioplegia while leaks from arterial branches were ligated with suture to assure adequate perfusion. The atrium was then perfused with Tyrode's at 37° C. for 5 min to remove cardioplegia solution and assess for viability—i.e., the reestablishment of beating. If viable, the atrium was then perfused at ~12 mL/min with $Ca^{2+}$-free Tyrode's solution for ~20 min, followed by ~40 min of perfusion with the same solution containing ~100 U/mL collagenase (Worthington Biochemical) and 1% BSA; all at 37° C. Thereafter, the atrial tissue was transferred to dish and cut into small pieces (~0.5 $cm^2$). These tissue pieces were then transferred to conical plastic tubes, and fresh enzyme solution (37° C.) was added. The tissue pieces were triturated in the fresh enzyme solution for 5-15 min for 15 min. The triturated tissue suspension was then filtered through nylon mesh (800 µm) to remove connective tissue debris and undigested atrial tissue. The filtered cell\tissue suspension was then briefly centrifuged at ~500 g, then enzyme solution poured off, and cell\tissue suspension resuspended in Tyrode's solution containing 200 µM $Ca^{2+}$ and 0.1% BSA. This resuspension was then and filtered through a nylon mesh (210 µm), briefly centrifuged at <500 g, and again resuspended in Tyrode's solution containing 200 µM $Ca^{2+}$ and 0.1% BSA to isolate dispersed cells. After cells settled for about 30 minutes, the solution was suctioned off and gradually replaced with a HEPES-buffered solution containing (mM) NaCl 137, KCl 5.4, MgCl2 1.0, CaCl2 1.8, HEPES 10, glucose 11, and 0.1% BSA; pH 7.4. Cells were stored in this solution at room temperature (RT) until use.

CCh Concentration-$Ca^{2+}$ Transient Response Assay in Isolated Canine Atrial Myocytes Aliquots of isolated atrial myocytes were incubated for ~20 min with the $Ca^{2+}$-fluorescence dye, fluo-4 (5 µM, Invitrogen) and pluronic acid (Sigma-Aldrich) at a 2:1 fluo-4: pluronic acid ratio (fluo-4 and pluronic acid were from 1 mM stocks dissolved in dimethyl sulfoxide). Fluo-4-loaded myocytes were transferred to a temperature-controlled cell-superfusion/field-stimulation chamber (BT-1-TBSN/STIM-TB system, Cell MicroControls) on the stage of an inverted confocal microscope (Axiovert 110/LSM-510 system, Carl Ziess), superfused with normal HEPES-buffered Tyrode's solution and field-stimulated at 0.5 Hz at 25° C. AP-evoked $Ca^{2+}$ transients were acquired as confocal X-t line-scan images of uncalibrated fluo-4 fluorescence (excitation: 488 nm Argon laser line; collected emission: >505 nm longpass filtered) using the integrated Zeiss LSM Confocal Microscopy Software (V2.5) and either a 25× (NA 0.82, max. spatial resolution is ~0.3 µm at the 517 nm emission maxima for fluo-4) or 40× (NA 1.24, max. spatial resolution is ~0.2 µm at the 517 nm emission maxima for fluo-4) water objective at a typical pixel density of 512 pixels/line and a scan rate of 1.92 msec/line-scan. Laser photobleaching/phototoxicity was minimized by scanning at <10% output transmission. Changes in $Ca^{2+}$ transients in response to CCh (0.01-30 µM) acutely applied for ≦3-10 s depending on CCh concentration—e.g., 10 s for lower concentrations, 3 s for higher concentrations (to avoid CCh-induced acute M2 desensitization)—via focal micro-superfusion with multiline temperature controlled fluid delivery apparatus (MPRE8, Cell MicroControls) were recorded from multiple myocytes per isolation preparation (typically, at least 12 cells/preparation). The time between serial applications of CCh was ≧1-3 min depending on previous dose applied—e.g., ~1 min for lower concentration, ~3 min for higher concentration—to further avoid CCh-induced acute M2 desensitization. $Ca^{2+}$ transient peak amplitude attenuation vs. CCh concentration relationship was constructed from the results obtained and subjected to logistical regression to determine the apparent $IC_{50}$ and maximum for the relationship (SigmaPlot, SysStat).

Figure 33:
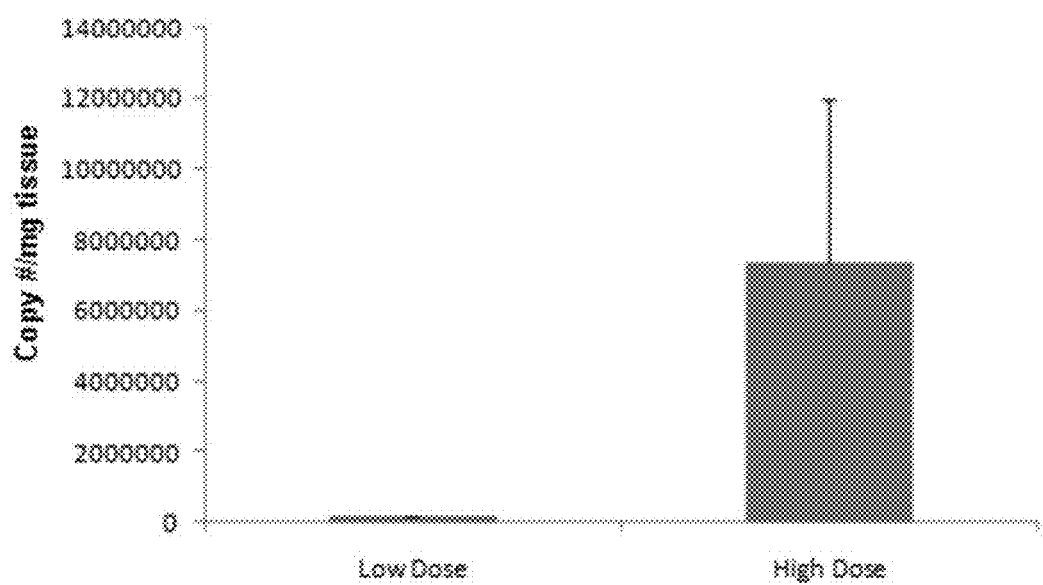
FIG. 33 shows gene expression after injection of low dose vs. high dose of minigene. The figure shows that with a ~10 times higher dose of minigene (15-20 mg), gene expression in the PLA, as assessed by PCR, was significantly greater as compared to low dose of minigene (1-2 mg). The y-axis represents copy number of plasmid/mg of tissue.

Supporting Data
A. Mean PR, QRS and RR intervals with and without vagal stimulation:
Without Vagal Stimulation:
PR=98.4±16.5 msec; QRS=57.4±0.9 msec; and RR=533.6±33.5 msec
With Vagal Stimulation:
PR=162.2±19.2 msec; QRS=58.4±4.3 msec; and RR=774±76.1 msec
B. Blood Pressure Trends at the Time of Terminal Surgery (During Vagal Stimulation Protocol).
BP was measured every 15 minutes; shown below are BP recordings at 30 minute intervals, over the duration of the protocol (i.e. 3 hours):
Dog 1: 82/47, 109/81, 115/82, 81/55, 99/63, 76/51
Dog 2: 89/62, 99/76, 100/60, 94/60, 93/64, 90/37
Dog 3: 109/49, 133/100, 90/37, 104/65, 105/73, 101/47
Dog 4: 112/93, 100/81, 103/64, 94/61, 90/50, 82/50
Dog 5: 87/44, 106/75, 97/62, 109/81, 100/79, 97/72
Results
G$\alpha_x$ Minigene Infection vs. G$\alpha_x$ Minigene Gene Product Expression In pilot experiments (N=6), 1-2 mg G$\alpha_{i2}$ctp minigene was injected into the PLA immediately followed by electroporation. However, this pilot minigene injection dose resulted in low-modest G$\alpha_{i2}$ctp mRNA expression in the PLA (FIG. 33). A ~10× injection dose of minigene (15-20 mg) resulted in significantly greater G$\alpha_{i2}$ctp mRNA expression (FIG. 33), and was used in all subsequent experiments where G$\alpha_{i2}$ctp minigene was tested alone. Assessment of mRNA expression in canine PLAs in which G$\alpha_{i2}$ctp minigene had been delivered (G$\alpha_{i2}$ctp minigene alone experiments) suggested a trend toward increased G$\alpha_{o1}$ mRNA compared control PLAs. Thus, additional experiments were conducted in which G$\alpha_{i2}$ctp minigene was delivered together with G$\alpha_{o1}$ctp minigene, and an injection dose of 7-10 mg of each minigene was used. As described below, clear electrophysiological responses were obtained following these latter injection doses of minigenes.

Effects of G$\alpha_x$ Minigenes on Vagal-Induced ERP Shortening

The effects of PLA-delivery of G$\alpha_{i2}$ctp minigene (N=5) vs. G$\alpha_{i2}$ctp+G$\alpha_{o1}$ctp minigene (N=3) vs. G$\alpha_R$p minigene (N=5) on vagal-induced ERP shortening are shown in FIG. 29A. Vagal-induce ERP shortening was significantly less in the PLA of G$\alpha_{i2}$ctp dogs vs. G$\alpha_R$p dogs—(19.5±5.0 vs. 43.6±7.9 ms, p<0.05). There was no significant difference in vagal-induced ERP shortening between G$\alpha_{i2}$ctp and G$\alpha_R$p dogs in the PV and the LAA. In comparison, in G$\alpha_{i2}$ctp+G$\alpha_{o1}$ctp dogs, vagal-induced ERP shortening was almost entirely eliminated in the PLA (with shortening being significantly less than with G$\alpha_{i2}$ctp alone, i.e. 2.8±1.5 vs. 19.5±5.0 ms, p<0.01), and was also significantly attenuated in the PV and LAA (FIG. 29A).

Effects of G$\alpha_x$ Minigenes on CCh-Induced ERP Shortening

To more specifically assess the action of G$\alpha_x$ minigene delivery on M$_2$R|G$_{i/o}$-protein coupling and resultant ERP shortening, exogenously-applied CCh was used to induce ERP shortening in the PLA in G$\alpha_x$ctp dogs. To arrive at an appropriate CCh dose range for these in vivo experiments, it was first determined the concentration-response relationship for CCh to attenuate Ca$^{2+}$ transient peak amplitude in isolated canine atrial myocytes (FIG. 34). The IC$_{50}$ and maximum for this effect was 28±8 nM and 3 μM CCh, respectively. At CCh>3 μM the effect faded, indicating agonist-induce acute M$_2$R desensitization[17]. Since one goal was to obtain maximum CCh effect in atrial tissue while minimizing agonist-induced M$_2$R desensitization, a small in vivo test range was arrived of 3-30 μM CCh to assess ERP shortening following gene-delivery in vivo (previous experience indicated that in vivo dosage is ~3-10× the in vitro dosage). Moreover, as stated earlier, higher doses of CCh administered in vivo resulted in long periods of AF and therefore precluded ERP testing.

Accordingly, CCh (3-30 μM) was directly injected into the PLA. As expected, increasing doses of CCh caused progressively greater ERP shortening in the PLA, but as shown in FIG. 29B, CCh-induced ERP shortening was significantly less in G$\alpha_{i2}$ctp compared to G$\alpha_R$p dogs at lower CCh concentrations (3 μM, 10 μM). At 30 μM, there was no significant difference in ERP shortening between G$\alpha_{i2}$ctp and G$\alpha_R$p dogs. This indicates that 30 μM CCh stimulates M$_2$Rs sufficiently to overcome G$\alpha_{i2}$ctp inhibition of M$_2$R|G$_{i2}$ signaling (since G$\alpha_{i2}$ctp acts as a competitive inhibitor to endogenous M$_2$R|G$\alpha_{i2}$ interaction). In G$\alpha_{i2}$ctp+G$\alpha_{o1}$ctp dogs, there was no significant CCh-induced ERP shortening at any dose of CCh (including the highest dose of 30 μM), with ERP shortening being significantly less than the other two groups at each dose of CCh (FIG. 29B).

Effects of G$\alpha_x$ Minigenes on Vagal- and CCh-Induced AF

AF inducibility (in response to VS) was significantly less in G$\alpha_{i2}$ctp dogs vs. G$\alpha_R$p dogs and was lowest (zero) in G$\alpha_{i2}$ctp+G$\alpha_{o1}$ctp dogs, with not a single episode of AF>5 seconds being induced in this group (FIG. 30A). Mean AF duration (in response to VS) was also significantly less in G$\alpha_{i2}$ctp dogs vs. G$\alpha_R$p dogs, and was lowest in G$\alpha_{i2}$ctp+G$\alpha_{o1}$ctp dogs (FIG. 30A). Similarly, AF inducibility and AF duration in response to CCh were significantly less in G$\alpha_{i2}$ctp dogs vs. G$\alpha_R$p dogs, but were lowest in G$\alpha_{i2}$ctp+G$\alpha_{o1}$ctp dogs (FIG. 30B).

Effects of G$\alpha$i2 Expressing Minigene on AF Characteristics

Figure 31:
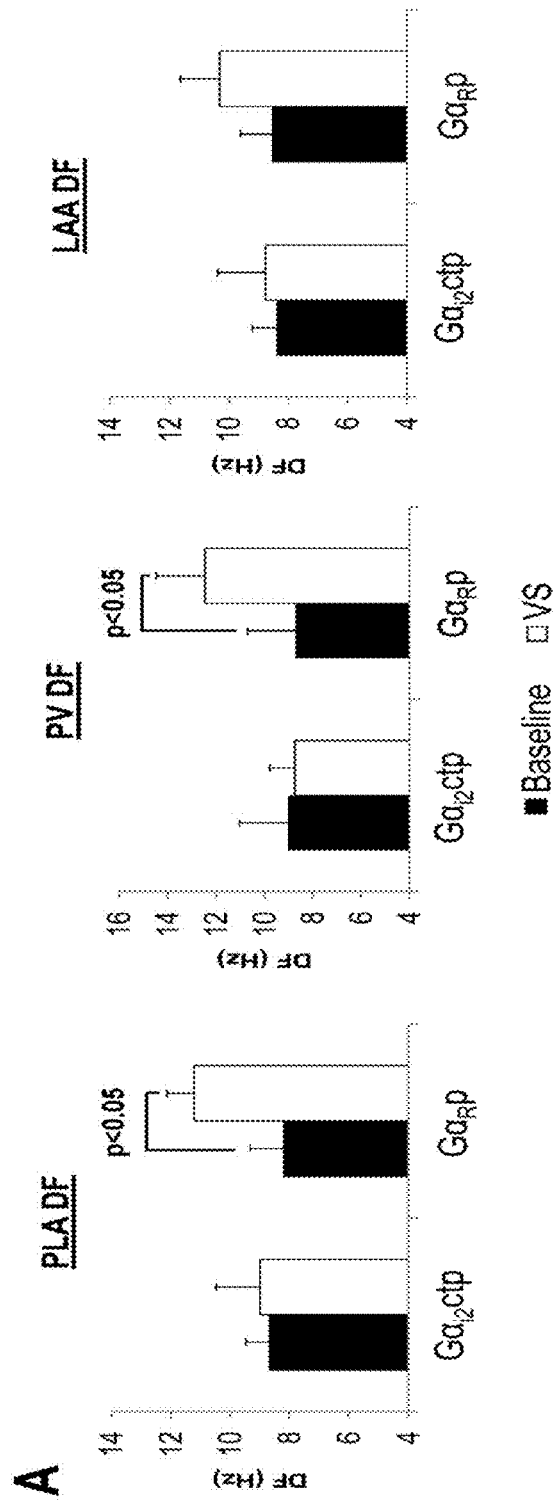
FIG. 31. Attenuation by minigene-expressing Gαi2ctp of VS-induced changes in AF dominant frequency. A. VS lead to a significant increase in AF dominant frequency (DF) in the PLA and PV of GαRcpt, but not in Gαi2ctp. No significant change in DF was noted in the LAA in either Gαi2ctp or GαRcpt dogs. B. Representative examples of AF electrograms recorded from the PV, PLA, and LAA and their corresponding power spectra. Electrograms recorded from the Gαi2atp group show a modest increase in DF with VS when compared to baseline. The GαRp group showed a much larger increase in DF.
Figure 31:
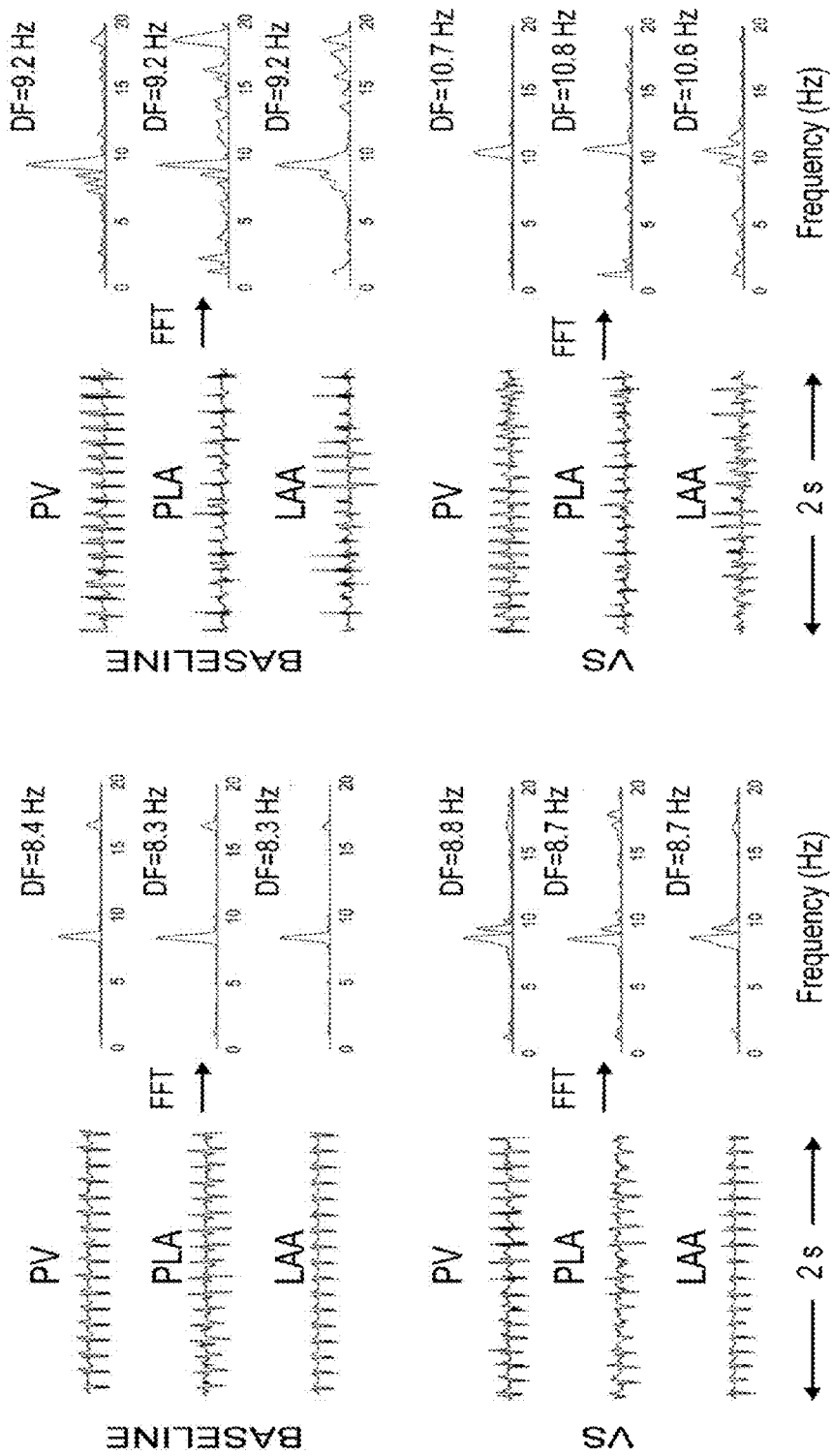

As previously shown, VS increases DF of AF[8]. When AF DF was assessed in G$\alpha_{i2}$ctp and G$\alpha_R$p dogs, the VS-induced increase in DF was significantly less in G$\alpha_{i2}$ctp dogs vs. G$\alpha$R-p dogs (where significant DF was noted in the PLA and PV in response to VS; FIG. 31A). FIG. 31B shows examples of AF electrograms (with and without VS) from G$\alpha_{i2}$ctp vs. G$\alpha_R$p dogs. AF DF could not be assessed in dogs receiving G$\alpha_{i2}$ctp+G$\alpha_{o1}$ctp dogs due to the very small number of AF episodes in these dogs and the very short duration of these episodes.

G$\alpha_x$ Transgene Expression in the Left Atrium and Pulmonary Veins

FIG. 32A shows relative G$\alpha_x$ctp mRNA expression in the PLA, PV and LAA after minigene delivery into the PLA. Robust expression for G$\alpha_{i2}$ctp, G$\alpha_{o1}$ctp and G$\alpha_R$p minigenes was found in the PLA, with minimal expression in the PV (which was adjacent to the area of injection), and with no expression in the LAA (remote from the site of injection). Anti-FLAG Western blot analysis (FIG. 32B) indicated G$\alpha_{i2}$ctp (FLAG-tagged) expression in the PLA, but not in the LAA. Immunohistochemistry showed evidence of FLAG staining in both myocytes (FIG. 32C, subpanel i) and nerve bundles (FIG. 32C, subpanel ii) in the PLA. In contrast, no FLAG was detected in the LAA (FIG. 32C, subpanel iii). Thus, G$\alpha_x$ctp minigene injection resulted in adequate G$\alpha_x$ctp translation at the site of minigene delivery.

Discussion

In this Example, the feasibility and efficacy of a targeted non-viral gene therapy approach to AF was demonstrated. Using minigene constructs that were delivered to the PLA by direct injection+electroporation, it was demonstrated that 3 days following gene injection: a) vagal responsiveness in the normal PLA was attenuated by a G$\alpha_{i2}$ctp expressed in situ by a plasmid expression vector and b) vagal responsiveness was almost entirely eliminated in the PLA and significantly attenuated elsewhere in the left atrium by a combination of minigenes expressing $G\alpha_{i2}$ctp and $G\alpha_{o1}$ctp, with a resulting, dramatic decrease in vagal-induced AF.

Gene Therapy in AF—Prior Experience in Modification of Autonomic Signaling Via G-Protein Related Pathways In an innovative approach, Donahue et al[18,19] used an adenoviral vector overexpressing $G\alpha_i$ to suppress AV conduction and thereby slow heart rate during AF. The approach in this Example differs from Donahue et al. in that instead of increasing $G\alpha_i$ activity in the AV node to decrease ventricular rates during AF, this Example inhibited $M_2R|G\alpha_{i/o}$ interactions in the left atrium with non-viral minigene-expressing $G\alpha_{i/o}$ctps, with the intent of modifying the autonomic substrate in a region of the heart (PLA) that is considered critical to the genesis of AF. Indeed, disruption of $M_2R|G\alpha_1$ coupling caused decreased ERP responsiveness and AF inducibility, which became much more apparent upon the additional disruption of $M_2R|G\alpha_o$ coupling. Moreover, disruption of $M_2R|G\alpha_1$ coupling caused significant attenuation of vagal-induced increase in DF (of the AF that was induced).

Redundancy of G-Protein Coupling to $M_2$Rs in the Atrium

It is well established that $M_2R$ signaling in the atria is transduced by pertussis toxin-sensitive $G_{i/o}$-proteins. But as there are six GTP-binding $G\alpha$ subunit isoforms known ($G\alpha_{i1,2\&3}$; $G\alpha_{o1,2\&3}$), the specific identity of the $G\alpha_{i/o}$ isoform(s) that couple to atrial $M_2$Rs has not been unequivocally established[11, 12, 20, 21]. Indeed, $G\alpha_o$ has been found to be co-localized with $G\alpha_i$ in the porcine atrium in a 1:1 ratio[22], and can activate $I_{K-ACh}$ as efficiently as $G\alpha_i$[23]. To our knowledge, this is the first time disruption of $M_2R|G\alpha_o$ coupling has been attempted and shown to significantly contribute to a decrease in vagal-induced AF in the large animal heart.

Gene Delivery in the Atrium—Viral Versus Non-Viral Approaches

Both viral and non-viral delivery methods have relative advantages for use in myocardial gene delivery[24,25]. Importantly, a non-viral approach results in a reduced inflammatory and immune response in vivo[26], and therefore has a more favorable safety profile. Recent improvements in physical delivery methods such as sonoporation and electroporation have allowed increasing levels of gene transfer and expression with naked DNA, nearing that of viral vectors[26]. In this Example, it was demonstrated that $G\alpha_{i/o}$ctps constitutively expressed via non-viral DNA vectors delivered into the PLA followed by electroporation results in attenuated vagal/$M_2$R-induced ERP shortening and AF.

Example 5

$G\alpha o1$ Inhibition for Treating Arrhythmias

This Example describes the use of a $G\alpha o1$ inhibitor to treat arrhythmia is a subject. In one animal, the following was performed:

Day 1: Open-chest mapping was performed via a left lateral thoracotomy. 10 mg of minigene expressing $G\alpha o1$ peptide was then injected in the PLA, followed by electroporation.

Day 3: A left lateral thoracotomy was performed again. The left vagus nerve was isolated. ERPs were measured in the PLA, PV and LAA in the absence and presence of vagal stimulation. Data from the above animal was compared with other dogs that received other minigenes (i.e. $G\alpha i2$, $G\alpha i2+G\alpha o1$ and $G\alpha R$ (see Aistrup et al, Heart Rhythm 2011)

In response to the $G\alpha o1$ minigene, there was a significant reduction in vagal and CCh induced ERP shortening as compared to dogs receiving control gene (expressing $G\alpha R$). Vagal induced ERP shortening was significantly less than in $G\alpha R$ dogs, but was significantly greater than in the dogs that received $G\alpha i2+G\alpha o1$ (see FIG. 35). This Example demonstrates that minigene expressing $G\alpha o1$ inhibitory peptide decreases vagal induced ERP shortening.

References

1. Benjamin E J, Levy D, Vaziri S M, D'Agostino R B, Belanger A J, Wolf P A. Independent risk factors for atrial fibrillation in a population-based cohort. The Framingham Heart Study. JAMA 1994; 271:840-4.
2. Dobrev D, Nattel S, New antiarrhythmic drugs for treatment of atrial fibrillation. Lancet 2010; 375:1212-23.
3. Sturrock A, Cahill B, Norman K, et al. Transforming growth factor-β1 induces Nox4 NAD(P)H oxidase and reactive oxygen species-dependent proliferation in human pulmonary artery smooth muscle cells. American Journal of Physiology—Lung Cellular and Molecular Physiology 2006; 290:L661-L73.
4. Ng J, Villuendas R, Cokic I, et al. Autonomic Remodeling in the Left Atrium and Pulmonary Veins in Heart Failure—Creation of a Dynamic Substrate for Atrial Fibrillation. Circulation: Arrhythmia and Electrophysiology.
5. Sharifov O F, Fedorov V V, Beloshapko G G, Glukhov A V, Yushmanova A V, Rosenshtraukh L V. Roles of adrenergic and cholinergic stimulation in spontaneous atrial fibrillation in dogs. J Am Coll Cardiol 2004; 43:483-90.
6. Oliveira M, da Silva M N, Geraldes V, et al. Acute vagal modulation of electrophysiology of the atrial and pulmonary veins increases vulnerability to atrial fibrillation. Exp Physiol 2011; 96:125-33.
7. Dobrev D, Graf E, Wettwer E, et al. Molecular Basis of Downregulation of G-Protein-Coupled Inward Rectifying K+ Current (IK,ACh) in Chronic Human Atrial Fibrillation: Decrease in GIRK4 mRNA Correlates With Reduced IK,ACh and Muscarinic Receptor-Mediated Shortening of Action Potentials. Circulation 2001; 104:2551-7.
8. Aistrup G L, Villuendas R, Ng J, et al. Targeted G-protein inhibition as a novel approach to decrease vagal atrial fibrillation by selective parasympathetic attenuation. Cardiovasc Res 2009; 83:481-92.
9. Arora R, Ng J, Ulphani J, et al. Unique autonomic profile of the pulmonary veins and posterior left atrium. J Am Coll Cardiol 2007; 49:1340-8.
10. Patterson E, Po S S, Scherlag B J, Lazzara R. Triggered firing in pulmonary veins initiated by in vitro autonomic nerve stimulation. [see comment]. Heart Rhythm 2005; 2:624-31.
11. Ye C, Sowell M O, Vassilev P M, Milstone D S, Mortensen R M. G [alpha]i2, G [alpha]i3 and G [alpha]oare all Required for Normal Muscarinic Inhibition of the Cardiac Calcium Channels in Nodal/Atrial-like Cultured Cardiocytes. J Mol Cell Cardiol 1999; 31:1771-81.
12. Boknik P, Grote-Wessels S, Barteska G, et al. Genetic disruption of G proteins, Gi2α or Goα, does not abolish inotropic and chronotropic effects of stimulating muscarinic cholinoceptors in atrium. Br J Pharmacol 2009; 158: 1557-64.
13. Gilchrist A, Li A, Hamm H E. Design and use of C-terminal minigene vectors for studying role of heterotrimeric G proteins. Methods in Enzymology 2002; 344:58-69.
14. Dean D A, Machado-Aranda D, Blair-Parks K, Yeldandi A V, Young J L. Electroporation as a method for high-level nonviral gene transfer to the lung. Gene Ther 2003; 10:1608-15.
15. Arora R, Ulphani J S, Villuendas R, et al. Neural substrate for atrial fibrillation: implications for targeted parasympathetic blockade in the posterior left atrium. Am J Physiol Heart Circ Physiol 2008; 294:H134-44.
16. Yue L, Feng J, Li G R, Nattel S. Transient outward and delayed rectifier currents in canine atrium: properties and role of isolation methods. Am J Physiol Heart Circ Physiol 1996; 270:H2157-68.
17. Nilius B. Desensitization of the muscarinic receptor in the mammalian atrial myocardium. Biomed Biochim Acta 1983; 42:519-26.
18. Bauer A, McDonald A D, Nasir K, et al. Inhibitory G protein overexpression provides physiologically relevant heart rate control in persistent atrial fibrillation. Circulation 2004; 110:3115-20.
19. Donahue J K, Heldman A W, Fraser H, et al. Focal modification of electrical conduction in the heart by viral gene transfer. Nature Medicine 2000; 6:1395-8.
20. Rudolph U, Spicher K, Birnbaumer L. Adenylyl cyclase inhibition and altered G protein subunit expression and ADP-ribosylation patterns in tissues and cells from Gi2 alpha–/–mice. Proc Natl Acad Sci USA 1996; 93:3209-14.
21. Li D, Melnyk P, Feng J, et al. Effects of Experimental Heart Failure on Atrial Cellular and Ionic Electrophysiology. Circulation 2000; 101:2631-8.
22. Ma A W, Pawagi A B, Wells J W. Heterooligomers of the muscarinic receptor and G proteins purified from porcine atria. Biochem Biophys Res Commun 2008; 374:128-33.
23. Zhang Q, Pacheco M A, Doupnik C A. Gating properties of GIRK channels activated by Galpha(o)- and Galpha(i)-coupled muscarinic m2 receptors in *Xenopus* oocytes: the role of receptor precoupling in RGS modulation. J Physiol 2002; 545:355-73.
24. Amit G, Kikuchi K, Greener I D, Yang L, Novack V, Donahue J K. Selective molecular potassium channel blockade prevents atrial fibrillation. Circulation 2010; 121: 2263-70.
25. Lyon A R, Sato M, Hajjar R J, Samulski R J, Harding S E. Gene therapy: targeting the myocardium. Heart 2008; 94:89-99.
26. Dean D A. Nonviral gene transfer to skeletal, smooth, and cardiac muscle in living animals. Am J Physiol Cell Physiol 2005; 289:C233-45.
27. Cokic I A G, Arapi D, Ng J, Gordon D, Benefield B, Wasserstrom J A, Goldberger J, Kadish A, Arora R. A Novel Minigene-based Approach to Achieve Long Term Vagal Inhibition in the Left Atrium. Heart Rhythm 2010; 7:594.
28. Giordano F J. Oxygen, oxidative stress, hypoxia, and heart failure. The Journal of Clinical Investigation 2005; 115:500-8.
29. Dröge W. Free Radicals in the Physiological Control of Cell Function. Physiol Rev 2002; 82:47-95.
30. Song Y, Shryock J C, Belardinelli L. An increase of late sodium current induces delayed after depolarizations and sustained triggered activity in atrial myocytes. American Journal of Physiology—Heart and Circulatory Physiology 2008; 294:H2031-H9.
31. Burashnikov A, Antzelevitch C. Reinduction of atrial fibrillation immediately after termination of the arrhythmia is mediated by late phase 3 early afterdepolarization-induced triggered activity. Circulation 2003; 107:2355-60.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for treating a subject having atrial or ventricular arrhythmias, comprising administering said subject an effective amount of a G-protein inhibitor, wherein said G-protein inhibitor comprises a Gαo1 inhibitor, and wherein said administering is under conditions such that symptoms of said atrial or ventricular arrhythmias are reduced or eliminated.

2. The method of claim 1, wherein said arrhythmia comprises atrial fibrillation.

3. The method of claim 1, wherein exposing said subject to said G-protein inhibitor disrupts one or more autonomic pathways.

4. The method of claim 3, wherein said autonomic pathways comprise sympathetic or parasympathetic pathways.

5. The method of claim 1, wherein said exposing comprises local administration.

6. The method of claim 5, further comprising electroporation of the site of said local administration.

7. The method of claim 1, wherein said G-protein inhibitor comprises a G-protein inhibitory peptide.

8. The method of claim 1, further comprising administering a Gαi2 inhibitor to said subject.

9. The method of claim 7, wherein said G-protein inhibitory peptide blocks receptor/G protein interaction.

10. The method of claim 1, wherein said G-protein inhibitor comprises a nucleic acid molecule encoding a G-protein inhibitory peptide.

11. The method of claim 1, wherein said exposing comprises topical administration.

12. The method of claim 1, wherein said subject is undergoing open-heart surgery.

13. The method of claim 1, wherein said subject has a clinical history of a vagal or adrenergic system role associated with said atrial arrhythmias.

14. The method of claim 1, wherein said subject has a paroxysmal or chronic history of atrial fibrillation.

15. The method of claim 1, wherein said exposing comprises treatment of autonomic pathways: a) within the left or right atrium of the heart; b) adjacent to the atria, or c) at one or more sites distant from the atria but that innervate the atria.

16. The method of claim 1, wherein said exposing comprises treatment of autonomic pathways in ventricular arrhythmias.

17. A method for treating a subject having atrial fibrillation comprising locally administering a G-protein inhibitor to the heart of said subject, and electroporating the site of administration, wherein said G-protein inhibitor comprises a Gαo inhibitor.

18. The method of claim 17, wherein said G-protein inhibitor is applied topically using a catheter or injection apparatus.

19. The method of claim 17, wherein said G-protein inhibitor comprises an inhibitory peptide or nucleic acid.

20. The method of claim 17, wherein said administering is under conditions such that symptoms of said atrial or ventricular arrhythmias are reduced.

\* \* \* \* \*

UNITED STATES PATENT AND TRADEMARK OFFICE
CERTIFICATE OF CORRECTION

| | | |
|---|---|---|
| PATENT NO. | : 8,518,884 B2 | |
| APPLICATION NO. | : 13/476412 | |
| DATED | : August 27, 2013 | |
| INVENTOR(S) | : Rishi Arora and Gary L. Aistrup | |

It is certified that error appears in the above-identified patent and that said Letters Patent is hereby corrected as shown below:

In the Specification

In Column 1, Line 16, please correct the government funding statement to read:
--This invention was made with government support under grant number R01 HL093490 and R21 HL088304 awarded by the National Institutes of Health. The government has certain rights in the invention.--

Signed and Sealed this
Twenty-eighth Day of November, 2023

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 25
<212> TYPE: DNA
<213> ORGANISM: Artificial sequence
<220> FEATURE:
<223> OTHER INFORMATION: Synthetic

<400> SEQUENCE: 1
agctcaagct tatcaagaac aacct                                          25

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
taccggatcc tcagaagagg c                                              21

<210> SEQ ID NO 3
<211> LENGTH: 24
<212> TYPE: DNA
<213> ORGANISM: Artificial sequence
<220> FEATURE:
```

```
<223> OTHER INFORMATION: Synthetic

<400> SEQUENCE: 3
agctcaagct tattgccaac aacc                                          24

<210> SEQ ID NO 4
<211> LENGTH: 24
<212> TYPE: DNA
<213> ORGANISM: Artificial sequence
<220> FEATURE:
<223> OTHER INFORMATION: Synthetic

<400> SEQUENCE: 4
ggtaccggat cctcagtaca agcc                                          24

<210> SEQ ID NO 5
<211> LENGTH: 22
<212> TYPE: DNA
<213> ORGANISM: Artificial sequence
<220> FEATURE:
<223> OTHER INFORMATION: Synthetic

<400> SEQUENCE: 5
caagcttaac ggcatcaagt gc                                            22

<210> SEQ ID NO 6
<211> LENGTH: 21
<212> TYPE: DNA
<213> ORGANISM: Artificial sequence
<220> FEATURE:
<223> OTHER INFORMATION: Synthetic

<400> SEQUENCE: 6
ggtaccggat cctcacagct t                                             21

<210> SEQ ID NO 7
<211> LENGTH: 11
<212> TYPE: PRT
<213> ORGANISM: Artificial sequence
<220> FEATURE:
<223> OTHER INFORMATION: Synthetic

<400> SEQUENCE: 7

Ile Lys Asn Asn Leu Lys Asp Cys Gly Leu Phe
1               5                   10
```